United States Patent
Li et al.

(10) Patent No.: US 11,739,122 B2
(45) Date of Patent: Aug. 29, 2023

(54) GLYCOPEPTIDE ANTIBIOTIC COMPOUNDS, METHODS FOR PRODUCING THE SAME, AND USES THEREOF

(71) Applicant: Academia Sinica, Taipei (TW)

(72) Inventors: Tsung-Lin Li, Taipei (TW); Chun-Man Huang, Taipei (TW); Kuan-Hung Lin, Taipei (TW)

(73) Assignee: Academia Sinica, Taipei (TW)

( * ) Notice: Subject to any disclaimer, the term of this patent is extended or adjusted under 35 U.S.C. 154(b) by 431 days.

(21) Appl. No.: 16/731,084

(22) Filed: Dec. 31, 2019

(65) Prior Publication Data

US 2020/0291071 A1    Sep. 17, 2020

Related U.S. Application Data

(60) Provisional application No. 62/818,173, filed on Mar. 14, 2019.

(51) Int. Cl.
*C07K 9/00* (2006.01)
*A61P 31/04* (2006.01)

(52) U.S. Cl.
CPC .............. *C07K 9/008* (2013.01); *A61P 31/04* (2018.01)

(58) Field of Classification Search
None
See application file for complete search history.

(56) References Cited

FOREIGN PATENT DOCUMENTS

| EP | 0276740 | * | 1/1988 | ............... C07K 9/00 |
| TW | 201540729 A | | 11/2015 | |

OTHER PUBLICATIONS

Malabarba, A., et al. J. Antibiot. (1990), 9; 1107-1121.*
Bernareggi, A., et al. Antimicrob. Agents Chemother. (1992), 36(11); 1744-1749.*
Huang et al., "Teicoplanin Reprogrammed with the N-Acyl-Glucosamine Pharmacophore at the Penultimate Residue of Aglycone Acquires Broad-Spectrum Antimicrobial Activities Effectively Killing Gram-Positive and -Negative Pathogens", ACS Infect, 2019,5, 430-442.

* cited by examiner

Primary Examiner — Kevin S Orwig

(57) ABSTRACT

A teicoplanin derivative useful for treating an infectious disease, having the structure of formula (I):

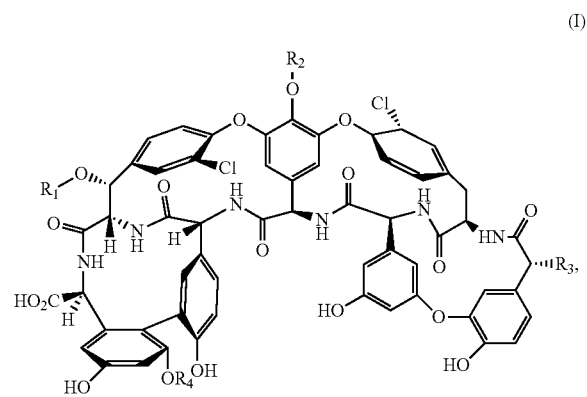

or the pharmaceutically acceptable salt, solvate, stereoisomer, derivative or prodrug thereof. In an exemplary compound of formula (I), $R_1$ is

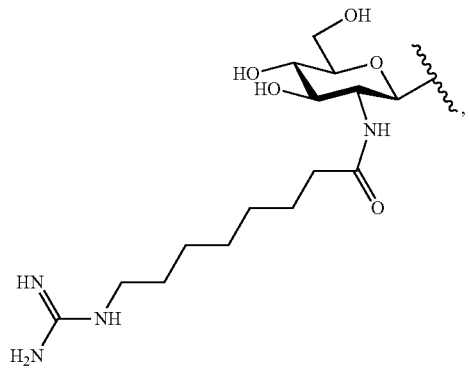

$R_2$ is H, $R_3$ is $-N(CH_3)_2$, and $R_4$ is H.

13 Claims, 22 Drawing Sheets

Specification includes a Sequence Listing.

SEQUENCE LISTING

<160> NUMBER OF SEQ ID NOS: 14

<210> SEQ ID NO 1
<211> LENGTH: 428

<212> TYPE: PRT
<213> ORGANISM: Artificial Sequence
<220> FEATURE:
<223> OTHER INFORMATION: synthesized_glycosyltransferase encoded by orf10

<400> SEQUENCE: 1

```
Met Gly Ser Ser His His His His His Ser Ser Gly Leu Val Pro
1               5                   10                  15

Arg Gly Ser His Met Arg Val Leu Leu Ser Thr Thr Gly Gly Arg Gly
            20                  25                  30

Asp Val Glu Pro Leu Val Ala Leu Ala Val Arg Phe Arg Glu Leu Gly
        35                  40                  45

Val Asp Ala Arg Val Cys Ala Pro Asp Cys Ala Asp Arg Leu Ala
50                  55                  60

Gly Val Gly Val Pro Leu Val Glu Val Gly Ser Val Arg Ala Met
65                  70                  75                  80

Met His Gly Gly Lys Arg Pro Ser Pro Glu Asp Ala Pro Arg Leu Asp
                85                  90                  95

Ala Glu Ala Ile Ala Thr Gln Phe Asp Lys Val Pro Ala Ala Ala Glu
            100                 105                 110

Gly Cys Ala Ala Val Val Thr Thr Gly Leu Leu Ser Ala Ala Val Ala
        115                 120                 125

Val Arg Ser Val Ala Glu Lys Leu Arg Ile Pro Tyr Val Tyr Ala Ala
130                 135                 140

Tyr Cys Pro Ile Tyr Leu Pro Ser Pro Tyr Tyr Pro Pro Pro Ala
145                 150                 155                 160

Leu Gly Gly Pro Pro Val Pro Glu Leu Thr Asp Asn Arg Ala Gln Trp
                165                 170                 175

Asn Arg His Ser Gln Gly Ala Tyr Arg Arg Phe Gly Ala Ala Leu Asn
            180                 185                 190

Ser His Arg Ala Ala Ile Gly Leu Pro Pro Val Glu Asn Ile Tyr Asp
        195                 200                 205

Tyr Ala Phe Ser Asp His Pro Trp Leu Ala Ala Asp Pro Val Leu Ala
210                 215                 220

Pro Leu Gln Pro Thr Asp Leu Asp Val Val Gln Thr Gly Ala Trp Ile
225                 230                 235                 240

Leu Pro Asp Gln Arg Pro Leu Ser Ala Glu Leu Glu Gly Phe Leu Arg
                245                 250                 255

Ala Gly Ser Pro Pro Val Tyr Val Gly Phe Gly Ser Gly Pro Ala Pro
            260                 265                 270

Ala Glu Ala Ala Arg Val Ala Ile Glu Ala Val Arg Ala Gln Gly Arg
        275                 280                 285

Arg Val Val Leu Ser Ser Gly Trp Ala Gly Leu Gly Arg Ile Asp Glu
290                 295                 300

Gly Asp Asp Cys Leu Val Val Gly Glu Val Asn His Gln Val Leu Phe
305                 310                 315                 320

Gly Arg Val Ala Ala Val Val His Ala Gly Ser Ala Gly Thr Thr Thr
                325                 330                 335

Ala Val Thr Arg Ala Gly Ala Pro Gln Val Val Pro Gln Met Thr
            340                 345                 350

Asp Gln Pro Tyr Tyr Ala Gly Arg Val Ala Asp Leu Gly Val Gly Val
        355                 360                 365

Ala His Asp Gly Pro Thr Pro Val Glu Ser Leu Ser Ala Ala Leu
370                 375                 380
```

```
Ala Thr Ala Leu Thr Pro Gly Ile Arg Ala Arg Ala Ala Val Ala
385                 390                 395                 400

Gly Thr Ile Arg Thr Asp Gly Thr Val Ala Ala Lys Leu Leu Leu
            405                 410                 415

Glu Ala Ile Ser Arg Gln Arg Ser Ser Val Ser Ala
            420                 425

<210> SEQ ID NO 2
<211> LENGTH: 273
<212> TYPE: PRT
<213> ORGANISM: Artificial Sequence
<220> FEATURE:
<223> OTHER INFORMATION: synthesized_deacylase encoded by orf2

<400> SEQUENCE: 2

Met Pro His Asp Pro Gly Ala Thr Arg Leu Leu Ala Ile Ser Pro His
1               5                   10                  15

Leu Asp Asp Ala Val Leu Ser Phe Gly Ala Gly Leu Ala Gln Ala Ala
            20                  25                  30

Gln Asp Gly Ala Asn Val Leu Val Tyr Thr Val Phe Ala Gly Ala Ala
        35                  40                  45

Gln Pro Pro Tyr Ser Pro Ala Ala Gln Arg Met His Thr Ile Trp Gly
    50                  55                  60

Leu Ala Pro Asp Asp Ala Val Leu Tyr Arg Arg Lys Glu Asp Ile
65                  70                  75                  80

Ala Ala Leu Asp His Leu Arg Val Ala His Arg His Gly Arg Phe Leu
                85                  90                  95

Asp Ser Ile Tyr Arg Lys Leu Pro Asp Gly Arg Trp Leu Thr Ala His
            100                 105                 110

Val Glu Gly Arg Gln Lys Leu Ala Val Asn Asp His Ser Pro Asp Ser
        115                 120                 125

Asp His Asp Leu Val Gly Glu Val Ala Asp Ile Arg Ser Ile Ile
    130                 135                 140

Asp Glu Phe Asp Pro Thr Leu Val Val Thr Cys Ala Ala Ile Gly Glu
145                 150                 155                 160

His Pro Asp His Glu Ala Thr Arg Asp Ala Ala Leu Phe Ala Thr His
                165                 170                 175

Glu Lys Asn Val Pro Val Arg Leu Trp Glu Asp Leu Pro Tyr Ala Val
            180                 185                 190

Phe Lys Ser Gly Ala Val Glu Leu Pro Gln Gly Phe Arg Leu Gly Ser
        195                 200                 205

Ala Asp Val Ser Ser Val Lys Pro Glu Met Arg Ser Gln Lys Phe Gln
    210                 215                 220

Ala Val Glu Arg Tyr Ser Ser Gln Met Val Leu Asn Gly Ser Glu
225                 230                 235                 240

Asn Asn Leu Phe Asp Arg Leu Asp Glu His Ala Arg Gln Asn Ala Pro
                245                 250                 255

His Gly Gly Tyr Gly Glu Thr Thr Trp Pro Val Val Arg Ser Asp Asp
            260                 265                 270

Ser

<210> SEQ ID NO 3
<211> LENGTH: 323
<212> TYPE: PRT
<213> ORGANISM: Artificial Sequence
<220> FEATURE:
```

<223> OTHER INFORMATION: synthesized_acyltransferase encoded by orf11

<400> SEQUENCE: 3

```
Met Asp Pro Glu Thr Val Arg Ile Ala Leu Gly Leu Glu Glu Arg Thr
1               5                   10                  15

Ala Ala Trp Leu Thr Glu Leu Asp Glu Leu Gly Pro Pro Ala Glu Pro
            20                  25                  30

Val Arg Leu Pro Arg Gly Glu Ala Arg Asp Leu Leu Arg Arg Leu
        35                  40                  45

Glu Val Pro Glu Leu Asp Ala Glu Ile Val Ala Ala Pro Asp
    50                  55                  60

Pro Asp Arg Asp Pro Ala Leu Trp Trp Leu Glu Arg Thr His His
65                  70                  75                  80

Ala Ile Val Arg His Met Gly Asp His Arg Ala Lys Pro Arg Gly Gly
                85                  90                  95

Pro Pro Leu Pro Tyr Glu Gly Gly Ala Ala Arg Tyr Phe His Val
            100                 105                 110

Tyr Val Phe Leu Ala Thr Val Pro Ala Val Arg Arg Phe His Ala Glu
            115                 120                 125

Arg Gly Ile Pro Asp Glu Val Gly Trp Glu Thr Leu Thr Gln Leu Gly
    130                 135                 140

Glu Leu Val Ala Ile His Arg Arg Lys Tyr Gly Gln Gly Gly Met Asn
145                 150                 155                 160

Met Gln Trp Trp Thr Thr Tyr His Leu Arg Gly Ile Leu Tyr Arg Leu
                165                 170                 175

Gly Arg Leu Gln Phe Ser Leu Ala Thr Gly Lys Asp Gly Thr Pro His
            180                 185                 190

Leu Gly Leu His Val Pro Glu Trp Gly Gly Pro Leu Leu Pro Lys Ala
        195                 200                 205

Tyr Asp Glu Ser Leu His Arg Ala Arg Pro Phe Phe Asp Arg His Phe
    210                 215                 220

Pro Glu His Gly Ala Arg Val Ala Trp Gly Ser Ser Trp Met Leu Asp
225                 230                 235                 240

Pro Gln Leu Glu Glu Tyr Leu Thr Glu Asp Ser Asn Ile Ile Gln Leu
                245                 250                 255

Ala Arg Phe Trp Thr Leu Thr Asp Ser Ala Pro Glu Pro Gly Asn Ala
            260                 265                 270

Asp Gly Asp Ser Ser Ile Leu Glu Phe Val Phe Arg Tyr Asn Gly Gln
        275                 280                 285

Pro Leu Asp Glu Leu Pro Gln Arg Ser Ser Leu Glu Arg Ala Val Ile
    290                 295                 300

Ala His Leu Lys Ala Gly Arg His Trp His Met Arg Thr Gly Phe Val
305                 310                 315                 320

Lys Leu Pro
```

<210> SEQ ID NO 4
<211> LENGTH: 297
<212> TYPE: PRT
<213> ORGANISM: Artificial Sequence
<220> FEATURE:
<223> OTHER INFORMATION: synthesized_methyltransferase encoded by dbv27

<400> SEQUENCE: 4

```
Met Gly Ser Ser His His His His His His Ser Ser Gly Leu Val Pro
1               5                   10                  15
```

```
Arg Gly Ser His Met Ile Ser Lys Ala Met His Gly Pro Ile Arg Pro
             20                  25                  30

Ala Arg Ala Asp Thr Leu Leu Ala Ser Val Gly Glu Arg Gly Ile Leu
         35                  40                  45

Cys Asp Phe Tyr Asp Glu Asn Ala Ser Glu Ile Phe Arg Asp Leu Glu
     50                  55                  60

Ala Asp Ala Gly Gly Thr Glu Glu Ala His Gly Phe Ala Ala Leu Val
 65                  70                  75                  80

Arg Pro Glu Ser Gly Ala Ile Leu Glu Leu Gly Ala Gly Thr Gly Arg
                 85                  90                  95

Leu Thr Ile Pro Leu Leu Glu Leu Gly Trp Glu Val Thr Ala Leu Glu
            100                 105                 110

Leu Ser Thr Ala Met Leu Thr Thr Leu Arg Thr Arg Leu Ala Asp Ala
        115                 120                 125

Pro Ala Asp Leu Arg Asp Arg Cys Thr Leu Val His Ala Asp Met Thr
    130                 135                 140

Ala Phe Lys Leu Gly Glu Arg Phe Gly Thr Ala Ile Leu Ser Pro Ser
145                 150                 155                 160

Thr Ile Asp Leu Leu Asp Asp Ala Asp Arg Pro Gly Leu Tyr Ser Ser
                165                 170                 175

Val Arg Glu His Leu Arg Pro Gly Gly Arg Phe Leu Leu Gly Met Ala
            180                 185                 190

Asn Pro Asp Ala Ser Gly Arg Gln Glu Pro Leu Glu Arg Thr Gln Glu
        195                 200                 205

Phe Thr Gly Arg Ser Gly Arg Arg Tyr Val Leu His Ala Lys Val Tyr
    210                 215                 220

Pro Ser Glu Glu Ile Arg Asp Val Thr Ile His Pro Ala Asp Glu Ser
225                 230                 235                 240

Ala Asp Pro Phe Val Ile Cys Val Asn Arg Phe Arg Val Ile Thr Pro
                245                 250                 255

Asp Gln Ile Ala Arg Glu Leu Glu Gln Ala Gly Phe Asp Val Val Ala
            260                 265                 270

Arg Thr Pro Leu Pro Gly Val Arg Asn His Glu Leu Val Leu Glu Ala
        275                 280                 285

Gln Trp Gly Ser Val Glu Asp Ala His
    290                 295

<210> SEQ ID NO 5
<211> LENGTH: 413
<212> TYPE: PRT
<213> ORGANISM: Artificial Sequence
<220> FEATURE:
<223> OTHER INFORMATION: synthesized_glycosyltransferase encoded by orf1

<400> SEQUENCE: 5

Met Gly Ser Ser His His His His His His Ser Ser Gly Leu Val Pro
  1               5                  10                  15

Arg Gly Ser His Met Arg Val Leu Phe Ser Ser Tyr Gly Thr Arg Gly
                 20                  25                  30

Asp Val Glu Pro Leu Val Ala Leu Ala Val Arg Leu Arg Glu Leu Gly
             35                  40                  45

Ala Glu Val Arg Met Cys Ala Ser Pro Asp Tyr Val Glu Arg Leu Ala
         50                  55                  60

Glu Val Glu Val Pro Met Val Pro Ile Gly Gln Pro Val Arg Ala Gly
 65                  70                  75                  80
```

```
Ala Arg Lys Gly Ala Ala Pro Pro Gly Ala Pro Glu Ala Val Ala Glu
                85                  90                  95

Val Ile Ala Glu Gln Phe Asp Arg Val Pro Pro Phe Ala Glu Gly Cys
            100                 105                 110

Asp Ala Val Val Ala Ser Gly Leu Val Ser Thr Ala Val Ala Val Arg
        115                 120                 125

Ser Val Ala Glu Lys Leu Gly Ile His His Tyr Ala Tyr Ala Val Leu
    130                 135                 140

Ser Pro Ser Phe Leu Arg Ala Pro Gly Val Thr Asp Ser Arg Asp Leu
145                 150                 155                 160

Arg Ala Arg Ala Asn Gln Gly Ala Tyr Arg Gln Phe Gly Gly Pro Leu
                165                 170                 175

Asn Ser His Arg Ala Ala Val Gly Leu Pro Pro Val Glu Lys Val Ile
            180                 185                 190

Asp Tyr Ala Phe Thr Glu Arg Pro Trp Leu Ala Ala Asp Pro Val Leu
        195                 200                 205

Asp Pro Leu Arg Pro Thr Asp Pro Asp Val Val Gln Thr Gly Ala Trp
    210                 215                 220

Ile Leu Pro Asp Gln Arg Pro Leu Ser Ala Glu Leu Glu Gly Phe Leu
225                 230                 235                 240

Arg Ala Gly Ser Pro Pro Val Tyr Val Gly Phe Gly Ser Gly Pro Ala
                245                 250                 255

Pro Ala Glu Ala Ala Arg Val Ala Ile Glu Ala Val Arg Ala Gln Gly
            260                 265                 270

Arg Arg Val Val Leu Ser Ser Gly Trp Ala Gly Leu Gly Arg Ile Asp
        275                 280                 285

Glu Gly Asp Asp Cys Leu Val Val Gly Glu Val Asn His Gln Val Leu
    290                 295                 300

Phe Gly Arg Val Ala Ala Val His His Gly Gly Ala Gly Thr Thr Thr
305                 310                 315                 320

Thr Ala Val Thr Arg Ala Gly Ala Pro Gln Val Val Pro Gln Lys
                325                 330                 335

Ala Asp Gln Pro Tyr Tyr Ala Gly Arg Val Ala Asp Leu Gly Val Gly
            340                 345                 350

Val Ala His Asp Gly Pro Thr Pro Thr Val Glu Ser Leu Ser Ala Ala
        355                 360                 365

Leu Ala Thr Ala Leu Thr Pro Gly Ile Arg Ala Arg Ala Ala Ala Val
    370                 375                 380

Ala Gly Thr Ile Arg Thr Asp Gly Thr Thr Val Ala Ala Lys Leu Leu
385                 390                 395                 400

Leu Glu Ala Ile Ser Arg Gln Arg Ser Ser Val Pro Ala
                405                 410

<210> SEQ ID NO 6
<211> LENGTH: 293
<212> TYPE: PRT
<213> ORGANISM: Artificial Sequence
<220> FEATURE:
<223> OTHER INFORMATION: synthesized_deacylase encoded by orf2T

<400> SEQUENCE: 6

Met Gly Ser Ser His His His His His His Ser Ser Gly Leu Val Pro
1               5                   10                  15

Arg Gly Ser His Met Pro His Asp Pro Gly Ala Thr Arg Leu Leu Ala
            20                  25                  30
```

```
Ile Ser Pro His Leu Asp Asp Ala Val Leu Ser Phe Gly Ala Gly Leu
         35                  40                  45

Ala Gln Ala Ala Gln Asp Gly Ala Asn Val Leu Val Tyr Thr Val Phe
 50                  55                  60

Ala Gly Ala Ala Gln Pro Pro Tyr Ser Pro Ala Ala Gln Arg Met His
 65                  70                  75                  80

Thr Ile Trp Gly Leu Ala Pro Asp Asp Ala Val Leu Tyr Arg Arg
             85                  90                  95

Lys Glu Asp Ile Ala Ala Leu Asp His Leu Arg Val Ala His Arg His
             100                 105                 110

Gly Arg Phe Leu Asp Ala Ile Tyr Arg Lys Leu Pro Asp Gly Arg Trp
         115                 120                 125

Leu Thr Ala His Val Glu Gly Arg Gln Lys Leu Ala Ala Asn Asp His
130                 135                 140

Ser Pro Asp Ser Asp His Asp Leu Val Gly Glu Val Ala Asp Asp Ile
145                 150                 155                 160

Arg Ser Ile Ile Asp Glu Phe Asp Pro Thr Leu Val Val Thr Cys Ala
                 165                 170                 175

Ala Ile Gly Glu His Pro Asp His Glu Ala Thr Arg Asp Ala Ala Leu
             180                 185                 190

Phe Ala Thr His Glu Lys Asn Val Pro Val Arg Leu Trp Glu Asp Leu
         195                 200                 205

Pro Tyr Ala Val Tyr Lys Ser Gly Ala Val Glu Leu Pro Gln Gly Phe
     210                 215                 220

Arg Leu Gly Ser Ala Asp Val Ser Ser Val Lys Pro Glu Met Arg Ser
225                 230                 235                 240

Gln Lys Phe Gln Ala Val Glu Arg Tyr Ser Ser Gln Met Val Leu Leu
                 245                 250                 255

Asn Gly Ser Glu Asn Asn Leu Phe Asp Arg Leu Asp Glu His Ala Arg
             260                 265                 270

Gln Asn Ala Pro His Gly Gly Tyr Gly Glu Thr Thr Trp Pro Val Val
         275                 280                 285

Arg Ser Asp Asp Ser
     290
```

```
<210> SEQ ID NO 7
<211> LENGTH: 345
<212> TYPE: PRT
<213> ORGANISM: Artificial Sequence
<220> FEATURE:
<223> OTHER INFORMATION: synthesized_acyltransferase encoded by orf11S

<400> SEQUENCE: 7
```

```
Met Gly Ser Ser His His His His His His Ser Ser Gly Leu Val Pro
1               5                   10                  15

Arg Gly Ser His Met Met Met Asp Pro Glu Thr Val Arg Ile Ala Leu
             20                  25                  30

Gly Leu Glu Glu Arg Thr Ala Ala Trp Leu Thr Glu Leu Asp Glu Leu
         35                  40                  45

Gly Pro Pro Ala Glu Pro Val Arg Leu Pro Arg Gly Glu Glu Ala Arg
 50                  55                  60

Asp Leu Leu Arg Arg Leu Glu Val Pro Glu Leu Asp Ala Glu Glu Ile
 65                  70                  75                  80

Val Ala Ala Ala Pro Asp Pro Asp Arg Asp Pro Ala Leu Trp Trp Leu
             85                  90                  95
```

-continued

```
Leu Glu Arg Thr His His Ala Ile Val Arg His Met Gly Asp His Arg
            100                 105                 110

Ala Lys Pro Arg Gly Pro Pro Leu Pro Tyr Glu Gly Gly Ala Ala
        115                 120                 125

Ala Arg Tyr Phe His Val Tyr Val Phe Leu Ala Thr Val Pro Ala Val
130                 135                 140

Arg Arg Phe His Ala Glu Arg Gly Ile Pro Asp Glu Val Gly Trp Glu
145                 150                 155                 160

Thr Leu Thr Gln Leu Gly Glu Leu Val Ala Ile His Arg Arg Lys Tyr
                165                 170                 175

Gly Gln Gly Gly Met Asn Met Gln Ala Trp Thr Thr Tyr His Leu Arg
            180                 185                 190

Gly Ile Leu Tyr Arg Leu Gly Arg Leu Gln Phe Ser Leu Ala Thr Gly
        195                 200                 205

Lys Asp Gly Thr Pro His Leu Gly Leu His Val Pro Glu Trp Gly Gly
210                 215                 220

Pro Leu Leu Pro Lys Ala Tyr Asp Glu Ser Leu His Arg Ala Arg Pro
225                 230                 235                 240

Phe Phe Asp Arg His Phe Pro Glu His Gly Ala Arg Val Ala Trp Gly
                245                 250                 255

Ser Ser Trp Met Leu Asp Pro Gln Leu Glu Glu Tyr Leu Thr Glu Asp
            260                 265                 270

Ser Asn Ile Ile Gln Leu Ala Arg Phe Trp Thr Leu Thr Asp Ser Ala
        275                 280                 285

Pro Glu Pro Gly Asn Ala Asp Gly Asp Ser Ser Ile Leu Glu Phe Val
290                 295                 300

Phe Arg Tyr Asn Gly Gln Pro Leu Asp Glu Leu Pro Gln Arg Ser Ser
305                 310                 315                 320

Leu Glu Arg Ala Val Ile Ala His Leu Lys Ala Gly Arg His Trp His
                325                 330                 335

Met Arg Thr Gly Phe Val Lys Leu Pro
            340                 345

<210> SEQ ID NO 8
<211> LENGTH: 28
<212> TYPE: DNA
<213> ORGANISM: Artificial Sequence
<220> FEATURE:
<223> OTHER INFORMATION: Synthesized_S98A primer

<400> SEQUENCE: 8
ccggttcctc gacgccatct accgtaag                                              28

<210> SEQ ID NO 9
<211> LENGTH: 27
<212> TYPE: DNA
<213> ORGANISM: Artificial Sequence
<220> FEATURE:
<223> OTHER INFORMATION: Synthesized_F193Y primer

<400> SEQUENCE: 9
ccgtatgcgg tctacaaatc aggtgcg                                               27

<210> SEQ ID NO 10
<211> LENGTH: 30
<212> TYPE: DNA
<213> ORGANISM: Artificial Sequence
<220> FEATURE:
<223> OTHER INFORMATION: Synthesized_V121A primer
```

```
<400> SEQUENCE: 10
ggcagaagct ggccgccaac gatcactcgc                              30

<210> SEQ ID NO 11
<211> LENGTH: 35
<212> TYPE: DNA
<213> ORGANISM: Artificial Sequence
<220> FEATURE:
<223> OTHER INFORMATION: Synthesized_W163A primer

<400> SEQUENCE: 11
cggcatgaac atgcaggcct ggaccaccta ccacc                        35

<210> SEQ ID NO 12
<211> LENGTH: 35
<212> TYPE: DNA
<213> ORGANISM: Artificial Sequence
<220> FEATURE:
<223> OTHER INFORMATION: Synthesized_S182R primer

<400> SEQUENCE: 12
cggccgcctg caattcagac tggccaccgg aaagg                        35

<210> SEQ ID NO 13
<211> LENGTH: 35
<212> TYPE: DNA
<213> ORGANISM: Artificial Sequence
<220> FEATURE:
<223> OTHER INFORMATION: Synthesized_A184R primer

<400> SEQUENCE: 13
cctgcaattc agtctgcgca ccggaaagga cggca                        35

<210> SEQ ID NO 14
<211> LENGTH: 35
<212> TYPE: DNA
<213> ORGANISM: Artificial Sequence
<220> FEATURE:
<223> OTHER INFORMATION: Synthesized_G194R primer

<400> SEQUENCE: 14
cggcacgccg cacctccgcc tgcacgttcc cgagt                        35
```

GLYCOPEPTIDE ANTIBIOTIC COMPOUNDS, METHODS FOR PRODUCING THE SAME, AND USES THEREOF

CROSS-REFERENCE TO RELATED APPLICATIONS

This application relates to and claims the benefit of U.S. Provisional Application No. 62/818,173, filed Mar. 14, 2019; the content of the application is incorporated herein by reference in its entirety.

STATEMENT REGARDING PRIOR DISCLOSURES BY THE INVENTOR OR A JOINT INVENTOR UNDER 37 C.F.R. 1.77(B)(6)

Most of the subject matter of the invention described in the present application was published by the inventors, Tsung-Lin Li, Chun-Man Huang, and Kuan-Hung Lin in an article titled "Teicoplanin reprogrammed with the N-acyl-Glc pharmacophore at the penultimate residue of aglycone acquires broad-spectrum antimicrobial activities effectively killing Gram-(+/−) pathogens." The article was published on Jan. 1, 2019 on ACS Infectious Diseases 2019, 5: 430-422. The publication was made by and/or originated from all member of the inventive entity of the present invention less than one year before the filing date of the present application. A copy of the article is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure in general relates to the field of disease treatment. More particularly, the present disclosure relates to novel glycopeptide compounds, and uses thereof in the prophylaxis and/or treatment of infectious diseases.

2. Description of Related Art

Emergence of antibiotic-resistant pathogens, such as methicillin-resistant *Staphylococcus aureus* (MRSA), vancomycin-resistant enterococci (VRE) and *Acinetobacter baumannii* (AB), has cast a serious public health threat of global concern. The glycopeptide antibiotics (GPAs), teicoplanin (Tei) and vancomycin (Van), are two drugs for treating severe Gram-(+) infections. This type of compounds binds specifically to the D-Ala-D-Ala terminus of the pentapeptide branch of Lipid II disrupting cell-wall integrity of pathogens. Since lipid II is a chemical entity rather than a mutable protein, it takes a longer time for pathogens to morph into GPAs resistance (i.e., through modifications of the D-Ala-D-Ala terminus of a lipid II precursor to D-Ala-D-Lac or D-Ala-D-Ser). The genes that remodel cell wall polymers conferring VRE immune to vancomycin have horizontally passed to MRSA on several occasions, staging an even gloomy public health threat because of an augmented virulence of the pathogens. Increasing incidences of infections caused by VRE, VISA (vancomycin-intermediate *S. aureus*) and VRSA (vancomycin-resistant *S. aureus*) have heralded an urgent need for new antibiotics that are able to shunt the drug resistance or eradicate the pathogens.

In view of the forgoing, there exists in the related art a need for novel GPAs for efficiently inhibiting the replication, activity and/or function of bacteria, especially antibiotic-resistant bacteria, thereby treating various infectious diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The first aspect of the present disclosure is directed to a novel glycopeptide compound of formula (I),

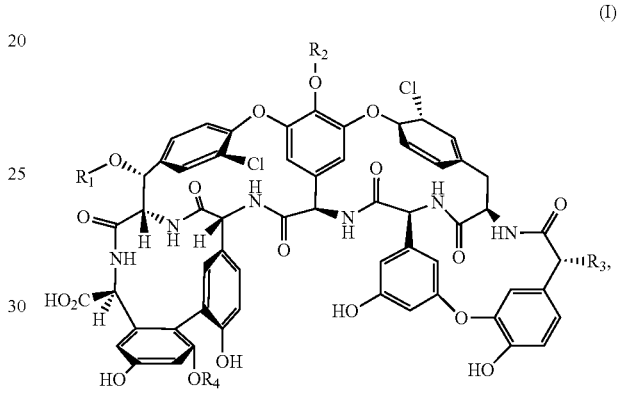

(I)

or its pharmaceutically acceptable salt, solvate, stereoisomer, derivative or prodrug,
wherein,
each $R_1$ and $R_2$ is independently H,

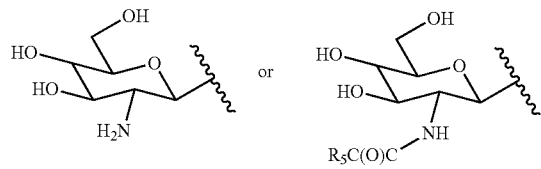

wherein $R_5$ is selected from the group consisting of H, alkyl, alkenyl, alkynyl, and aryl;
$R_3$ is —N($R_a$)($R_b$), wherein each $R_a$ and $R_b$ is independently H or alkyl;
$R_4$ is H or

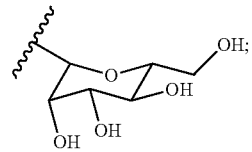 [SMILES: *C1OC(CO)C(O)C(O)C1O]

and
each alkyl, alkenyl, alkynyl and aryl is optionally substituted by halogen, alkoxy, $C_{1-6}$ alkyl, $C_{1-6}$ alkenyl, $C_{1-6}$ alkynyl, cycloalkyl, aryl, heteroaryl, —OH, —$NH_3^+$, —$NHR_c$ or

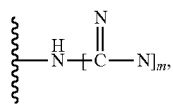

wherein $R_c$ is hydrogen or $C_{1-10}$ alkyl, and m is an integer from 1 to 5.

According to certain embodiments of the present disclosure, $R_5$ is C—C≡C, or $C_1$-$C_{12}$ alkyl optionally substituted by —OH, —$NH_2$, —$NH_3^+$, aryl, aryl halogen, or

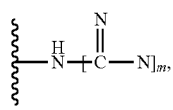

wherein m is an integer from 1 to 5.

According to some embodiments of the present disclosure, each $R_a$ and $R_b$ is independently H or methyl.

According to certain embodiments, in the formula (I), $R_1$ is H;

$R_2$ is

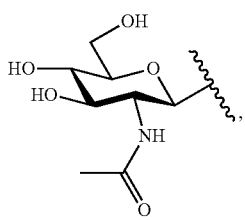

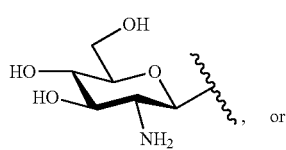

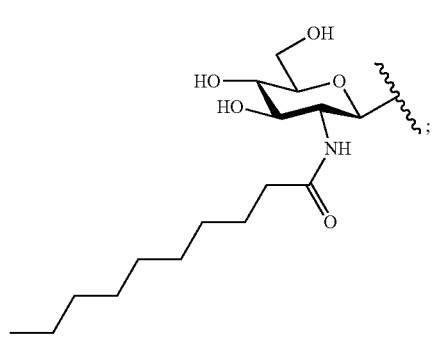

$R_3$ is —$NH_2$; and $R_4$ is H.

According to one preferred embodiment, in the formula (I), $R_1$ is H;

$R_2$ is

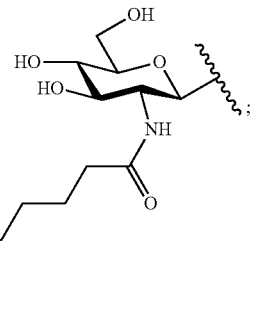

$R_3$ is —$NH(CH_3)$; and $R_4$ is H.

According to certain embodiments, in the formula (I), $R_1$ is H,

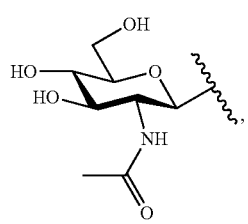

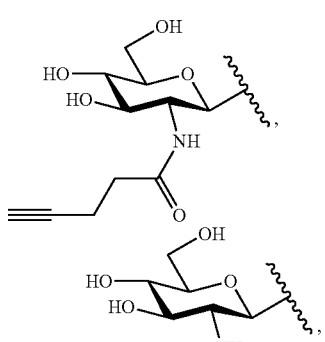

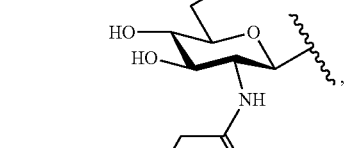

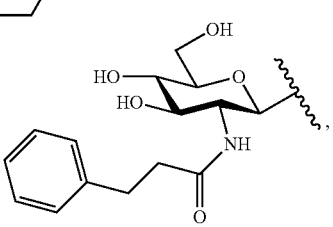

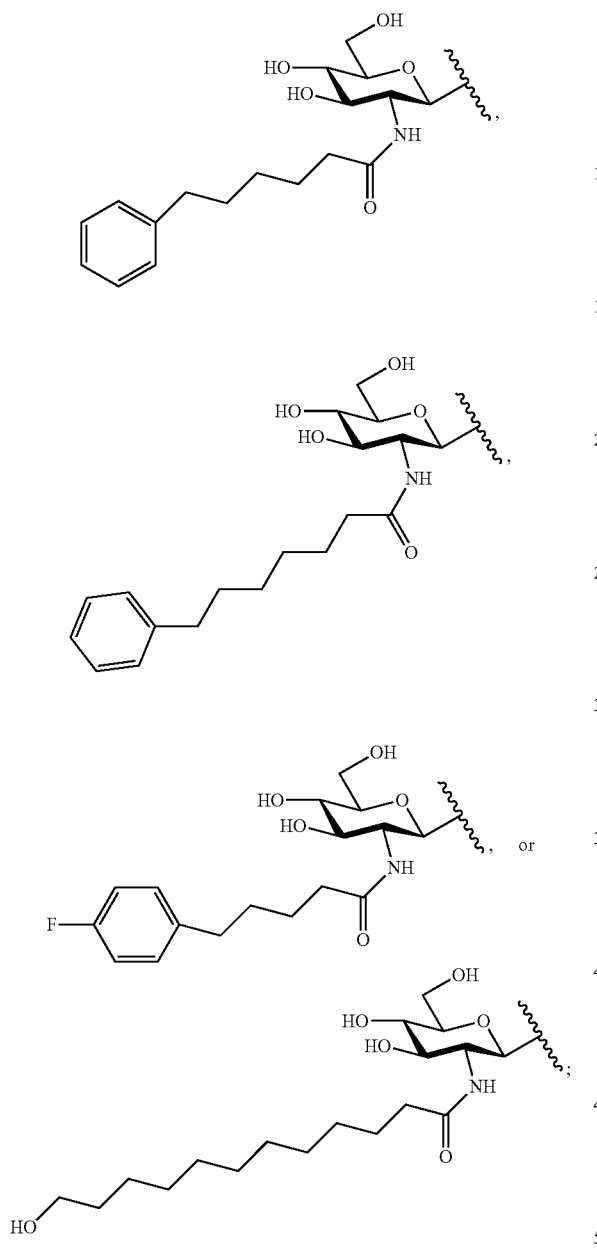
$R_2$ is H;
$R_3$ is —$NH_2$; and
$R_4$ is H.
According to certain embodiments, in the formula (I), $R_1$ is,
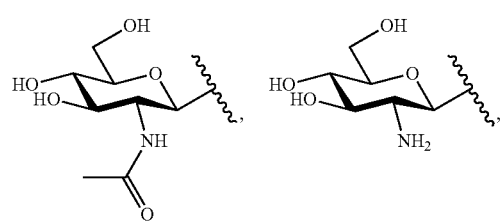
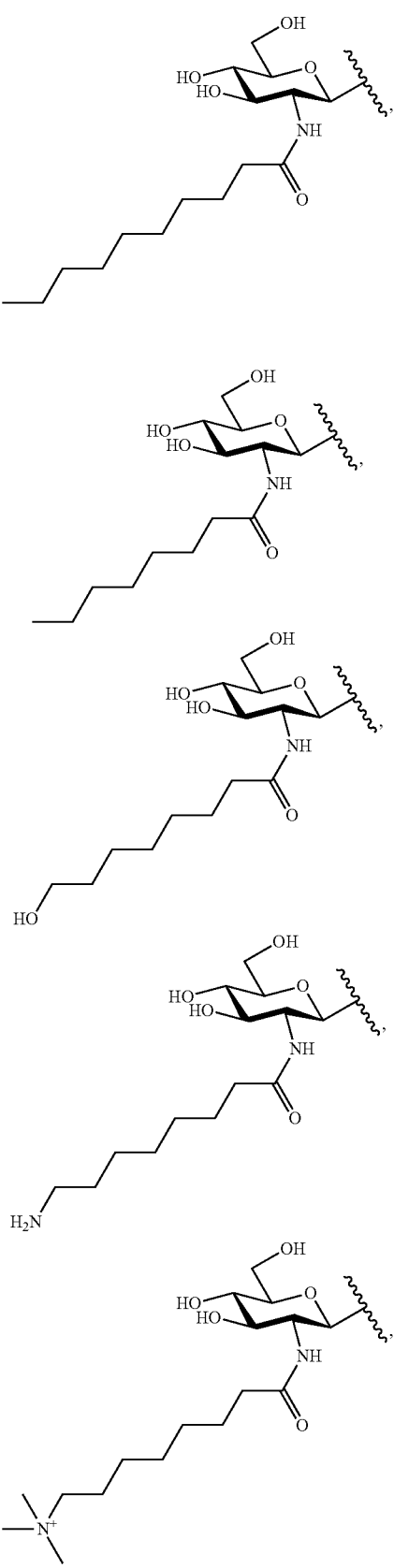

-continued

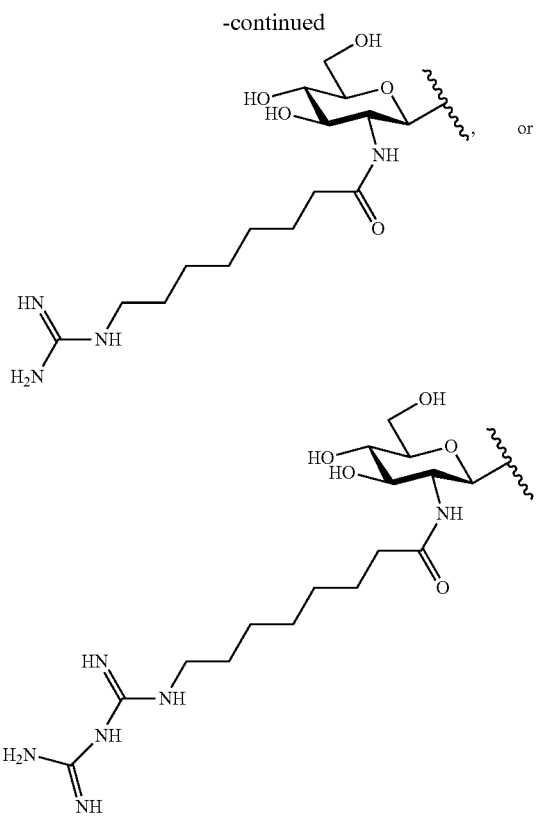

$R_2$ is H;
$R_3$ is —N(CH$_3$)$_2$; and
$R_4$ is H.

According to one preferred embodiment, in the formula (I),
$R_1$ is

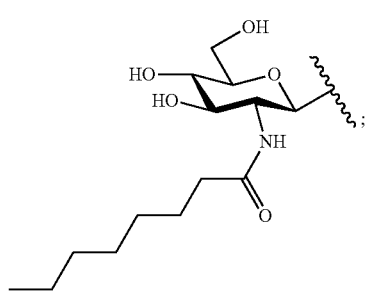

$R_2$ is H;
$R_3$ is —NH$_2$; and
$R_4$ is

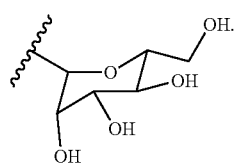 [SMILES: *C1OC(CO)C(O)C(O)C1O]

According to another embodiment, in the formula (I),
$R_1$ is

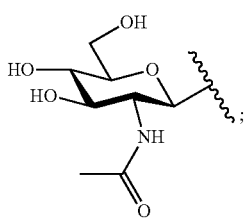

$R_2$ is

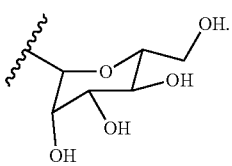 [SMILES: *C1OC(CO)C(O)C(O)C1O]

$R_3$ is —N(CH$_3$)$_2$; and
$R_4$ is

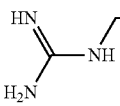

Another aspect of the present invention relates to a pharmaceutical composition or medicament for treating infectious diseases. The present pharmaceutical composition or medicament comprises one or more compounds described above, or the pharmaceutically acceptable salt, solvate, stereoisomer, derivative or prodrug thereof, and a pharmaceutically acceptable excipient.

Also disclosed herein are methods for treating infectious diseases by use of the compound, pharmaceutical composition or medicament of the present disclosure. The method comprises administering to a subject in need thereof an effective amount of the present compound, pharmaceutical composition or medicament.

In general, the infectious disease may be caused by/associated with a gram-positive (e.g., *Staphylococcus aureus* or Enterococci) or a gram-negative bacterium (e.g., *Acinetobacter baumannii*), in which the bacterium may be an antibiotic-sensitive or an antibiotic-resistant bacterium.

In a further aspect, the present disclosure pertains to methods of producing the present compound. The method comprises, (a) glycosylating a compound of formula (Ia) with the aid of a glycosyltransferase in the presence of an acylated glycan,

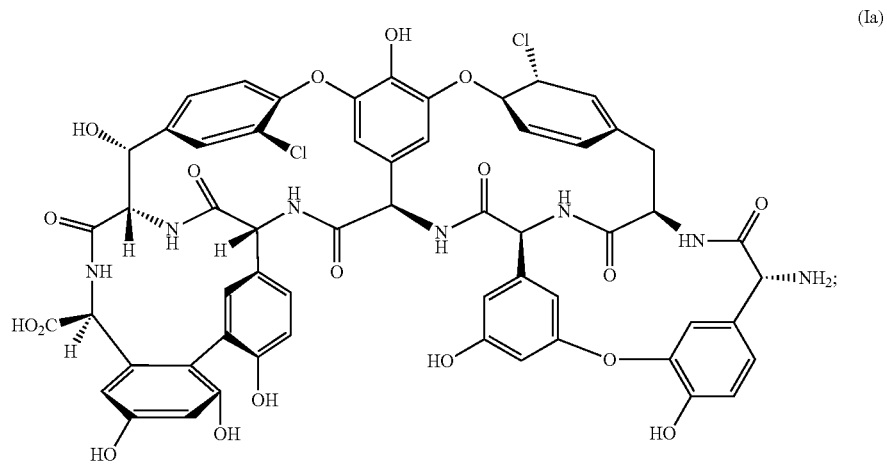

(Ia)

(b) deacylating the product of the step (a) with the aid of a deacylase; and
(c) acylating the product of the step (b) with the aid of an acyltransferase in the presence of an acyl donor thereby producing the compound of formula (I), wherein the acyl donor comprises a functional group of —C(O)CR$_5$, in which R$_5$ is C—C≡C, or C$_1$-C$_{12}$ alkyl optionally substituted by —OH, —NH$_2$, —NH$_3^+$, aryl, aryl halogen, or

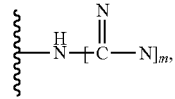

and m is an integer from 1 to 5.

According to some embodiments of the present disclosure, the acylated glycan is uridine diphosphate N-acetylglucosamine (UDP-GlcNAc).

According to certain embodiments, the glycosyltransferase comprises the amino acid sequence of SEQ ID NO: 1; the deacylase comprises the amino acid sequence of SEQ ID NO: 2; and the acyltransferase comprises the amino acid sequence of SEQ ID NO: 3. Optionally, the present method further comprises a step of reacting the product of the step (c) with a methyltransferase. Preferably, the methyltransferase comprises the amino acid sequence of SEQ ID NO: 4.

According to some embodiments, the glycosyltransferase comprises the amino acid sequence of SEQ ID NO: 5; the deacylase as illustrated in FIG. 1C) comprises the amino acid sequence of SEQ ID NO: 6; and the acyltransferase comprises the amino acid sequence of SEQ ID NO: 7. Optionally, the present method further comprises a step of reacting the product of the step (a) with a methyltransferase prior to the step (b). Preferably, the methyltransferase comprises the amino acid sequence of SEQ ID NO: 4.

According to one preferred embodiment, the acyl donor comprises a functional group of —C(O)CR$_5$, wherein R$_5$ is —NH$_2$. In this example, the present method further comprises a step of guanylating the product of the step (c).

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1A: compound 9; FIG. 1U: compound 31.

FIG. 2A: LC traces of enzymatic reactions for the N-acyl-Glc pharmacophore at r4 of Tei-pseudoaglycone, in which (line a) represents the reaction substrate Tei-aglycone 4; (line b) represents the product r4,GlcNAc Tei-pseudoaglycone 5 in the enzymatic reaction catalyzed by Orf10*; (line c) represents the product r4,Glm Tei-pseudoaglycone 6 in the enzymatic reaction catalyzed by Orf2*; (line d) represents the product r4,N-acyl-Glc Tei-pseudoaglycone 6 in the enzymatic reaction catalyzed by Orf11*; (lien e) represents the product r1,Me-r4,N-acyl-Glc Tei-pseudoaglycone 7 in the enzymatic reaction catalyzed by Dbv27; (line f) represents the product r6,GlcNAc Tei-pseudoaglycone 9 in the enzymeatic reaction catalyzed by Orf1; (line g) represents the product r1,Me$_2$-6,GlcNAc Tei-pseudoaglycone 10 in the enzymatic reaction catalyzed by Dbv27; (line h) represents the product r1,Me$_2$-r6,Glm Tei-pseudoaglycone 11 in the enzymatic reaction catalyzed by Orf2*T; (line i) represents the product r1,Me$_2$-r6,N-acyl-Glc Tei-pseudoaglycone 3 in the enzymatic reaction catalyzed by Orf11*S. FIGS. 2B and 2C: Binding affinity of Orf2*T vs. r4,GlcNAc Tei-pseudoaglycone 6 (FIG. 2B) or r6,GlcNAc Tei-pseudoaglycone 9 (FIG. 2C). FIGS. 2D and 2E: Binding affinity of Dbv27 vs. S-adenosylmethionine SAM ($K_d$=10 µM) (FIG. 2D) or r6,Glm-Tei-pseudoaglycone ($K_d$=5 µM) (FIG. 2E).

FIG. 3A: The morphological changes of MRSA (ATCC 700787) upon: a. no treatment, b. treated with compound 2, c. treated with compound 1, d. treated with compound 14, e. treated with compound 28. FIG. 3B: The morphological changes of VRE (ATCC 700221) upon: a. no treatment, b. treated with compound 2, c. treated with compound 1, d. treated with compound 14, e. treated with compound 28. FIG. 3C: The morphological changes of AB (ATCC 19606) upon: a. no treatment, b. treated with compound 24, c. treated with kanamycin, d. treated with kanamycin+compound 24, e. treated with colistin. IM: inner membrane; OM: outer membrane; CW: cell wall.

FIG. 4A: the cytotoxicity of compounds 1, 14, 18, 24 and daptomycin was examined against a human embryonic kidney cells (HEK293T) cell line at specified time points. FIG. 4B: The drug-induced hemolysis examination. FIG. 4C: The permeabilization capability of specified compounds on the cytoplasmic membrane of MRSA ATCC 700787 was examined using the propidium iodide (PI) dye assay. FIG. 4D: The permeabilization capability of specified compounds on the cytoplasmic membrane of AB was examined using the propidium iodide (PI) dye assay. FIG. 4E: The permeabilization capability of specified compounds on the outer membrane of MRSA (without inherent outer membrane) was examined using the 1-N-phenylnaphthylamine (NPN) permeabilization assay. FIG. 4F: The permeabilization capability of specified compounds on the outer membrane of AB (with intrinsic outer membrane) was examined using the 1-N-phenylnaphthylamine (NPN) permeabilization assay.

DETAILED DESCRIPTION OF THE INVENTION

Figure 1A:
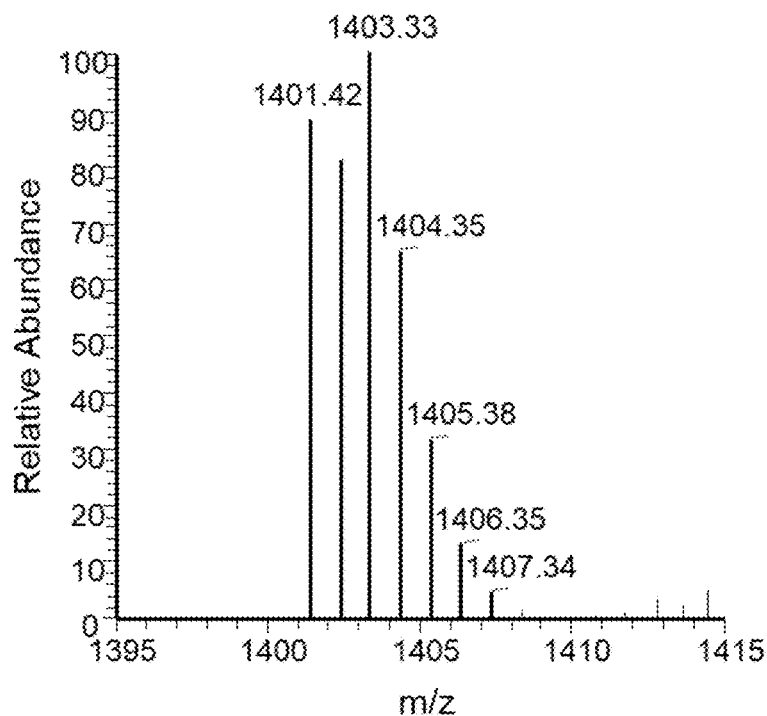
FIGS. 1A-1U are data of electrospray ionization mass spectrometry (ESI/MS) of specified compounds.
Figure 1B:
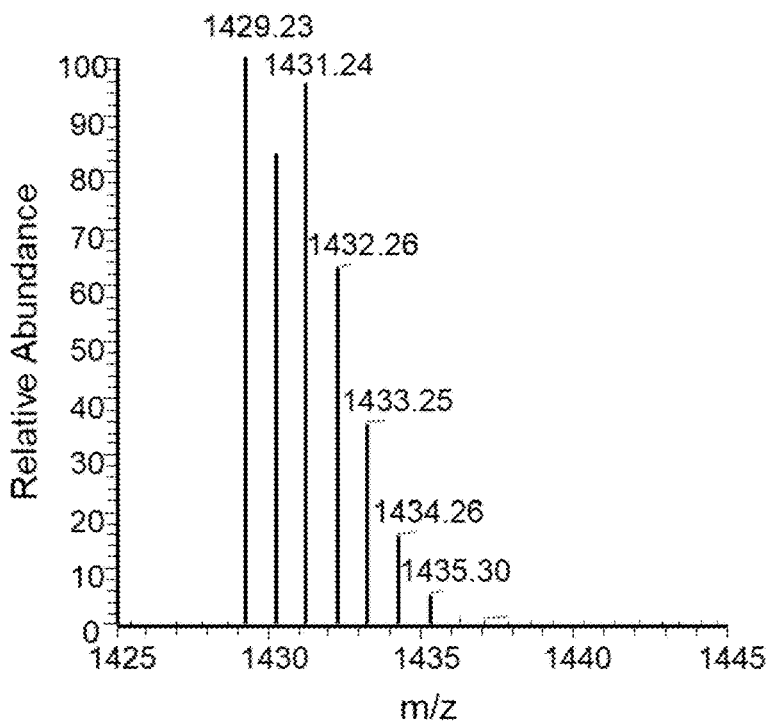
FIG. 1B: compound 10.
Figure 1C:
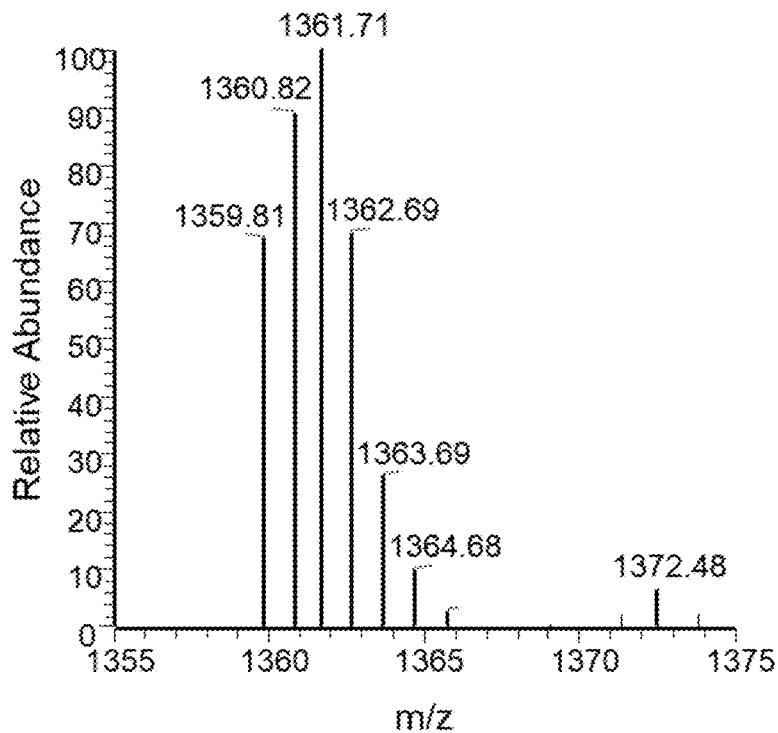
FIG. 1C: compound 12.
Figure 1D:
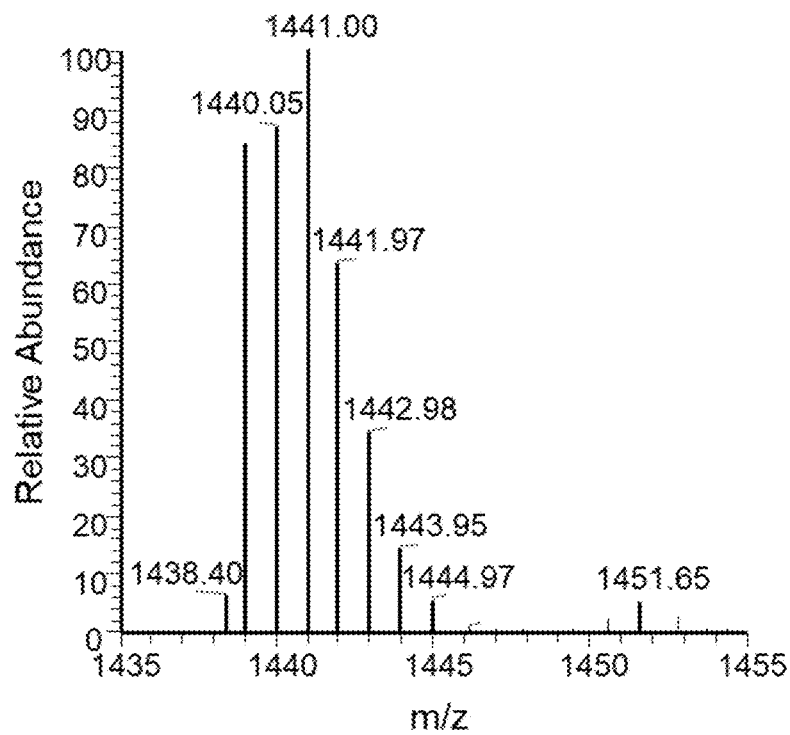
FIG. 1D: compound 13.
Figure 1E:
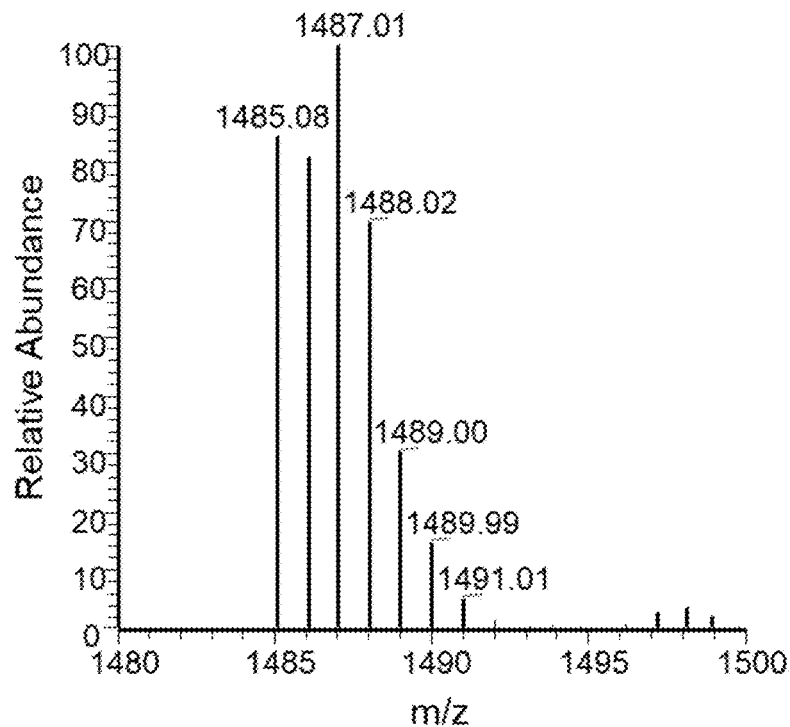
FIG. 1E: compound 14.
Figure 1F:
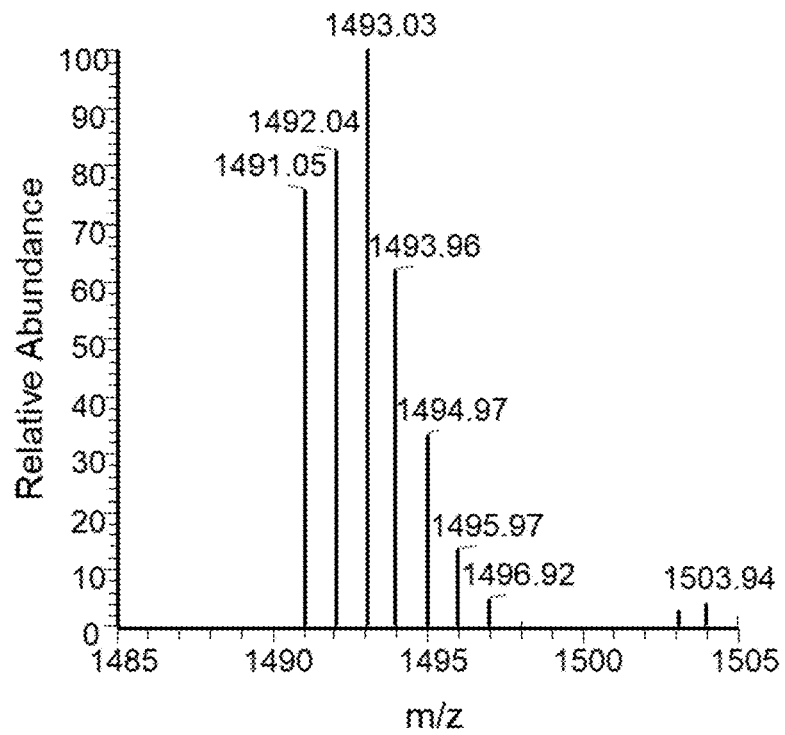
FIG. 1F: compound 15.
Figure 1G:
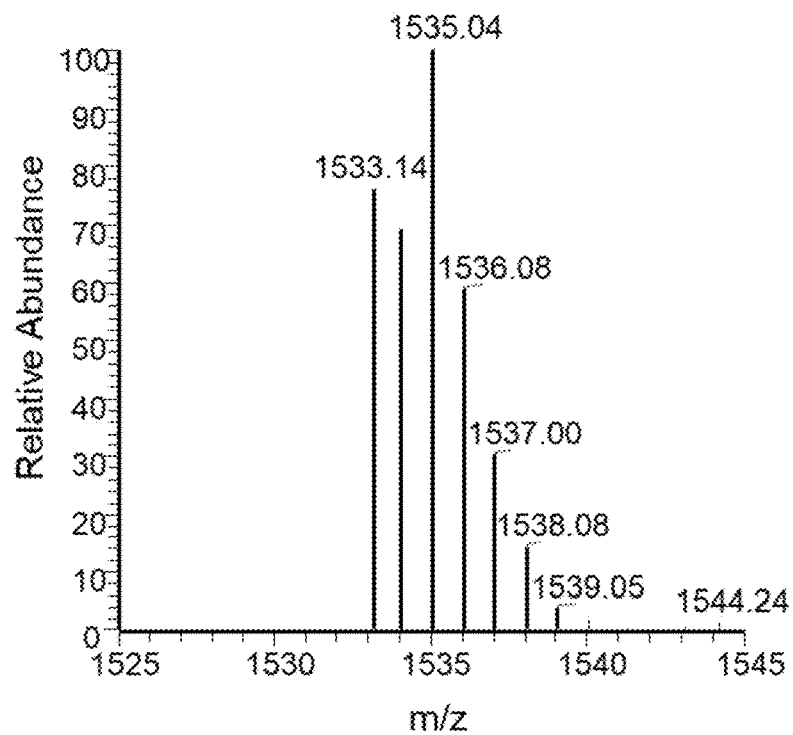
FIG. 1G: compound 16.
Figure 1H:
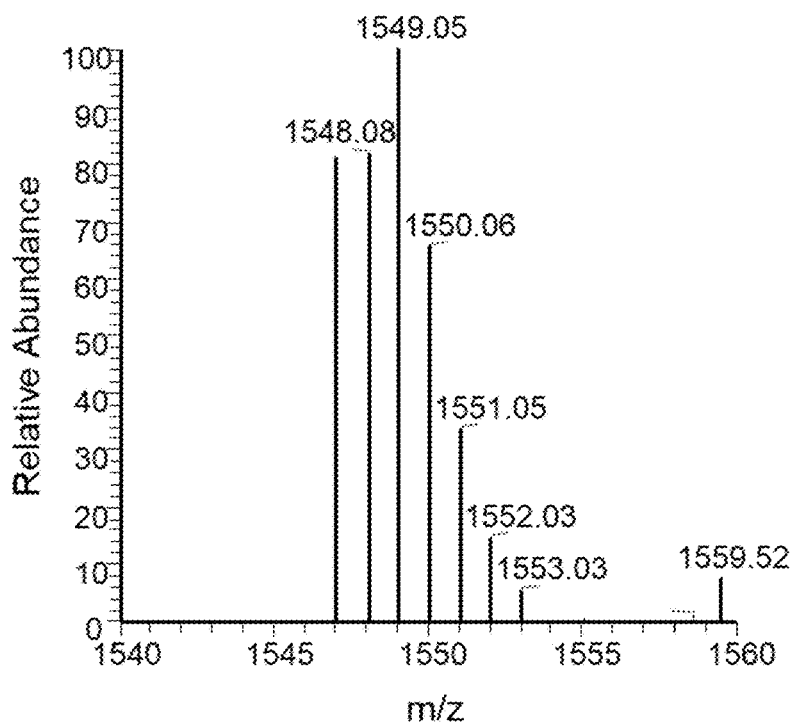
FIG. 1H: compound 17.
Figure 1I:
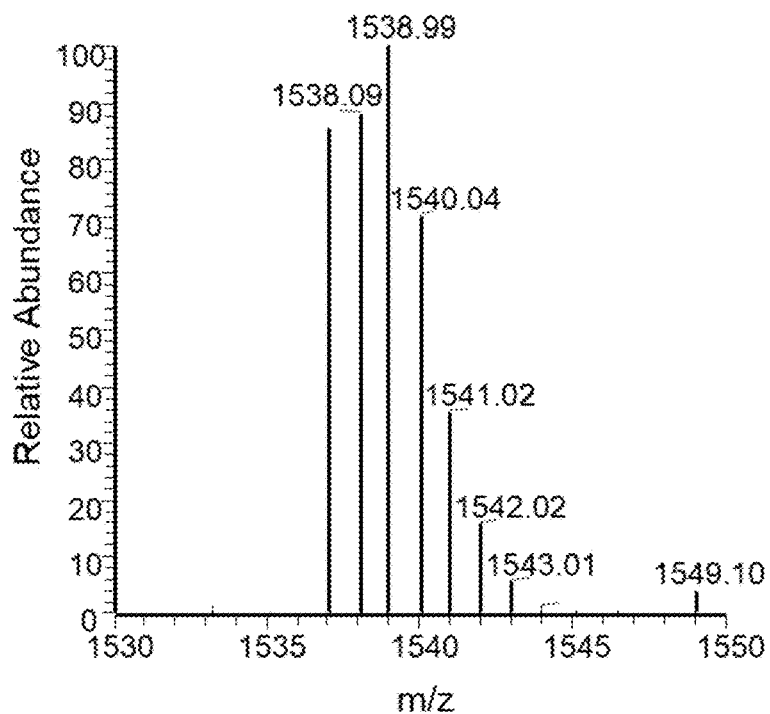
FIG. 1I: compound 18.
Figure 1J:
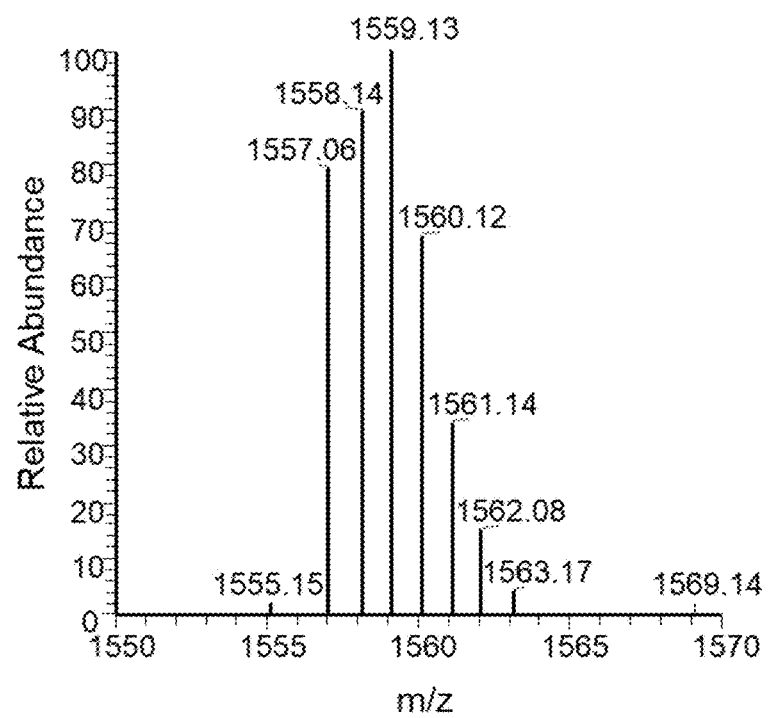
FIG. 1J: compound 19.
Figure 1K:
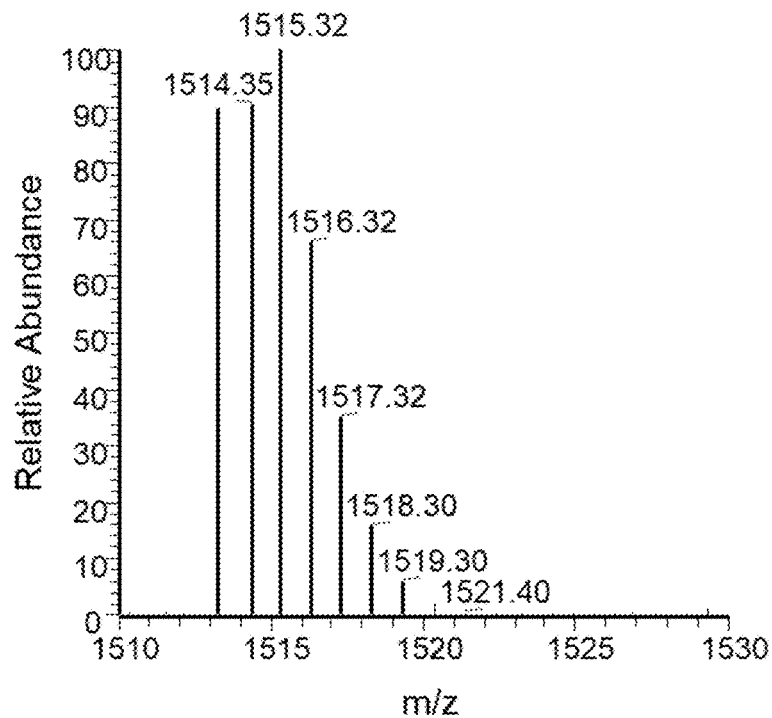
FIG. 1K: compound 20.
Figure 1L:
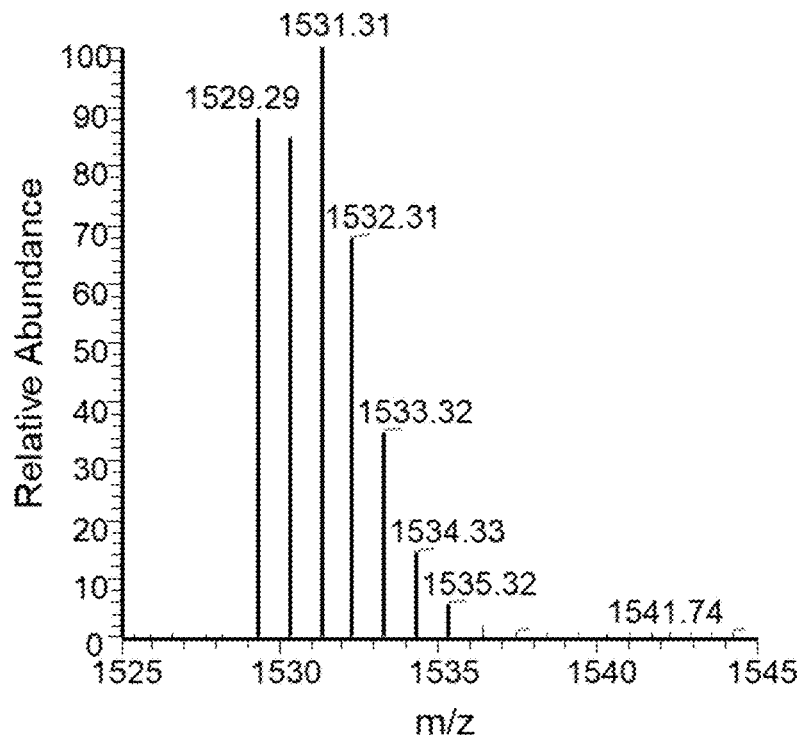
FIG. 1L: compound 21.
Figure 1M:
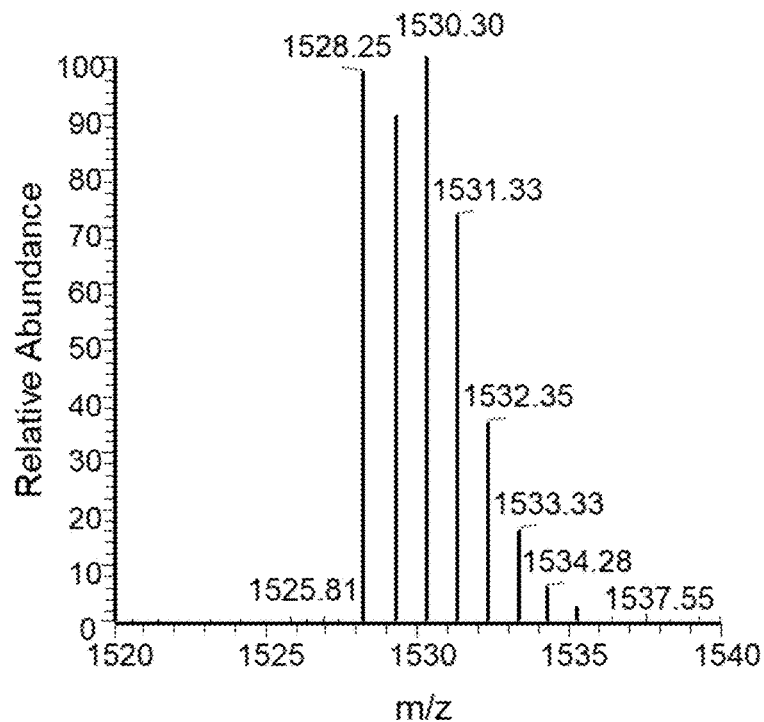
FIG. 1M: compound 22.
Figure 1N:
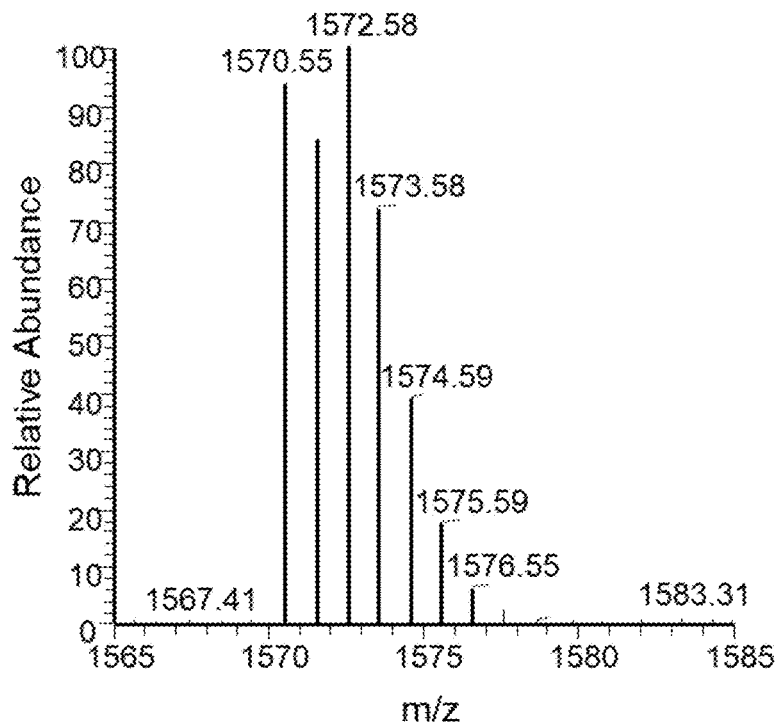
FIG. 1N: compound 23.
Figure 1O:
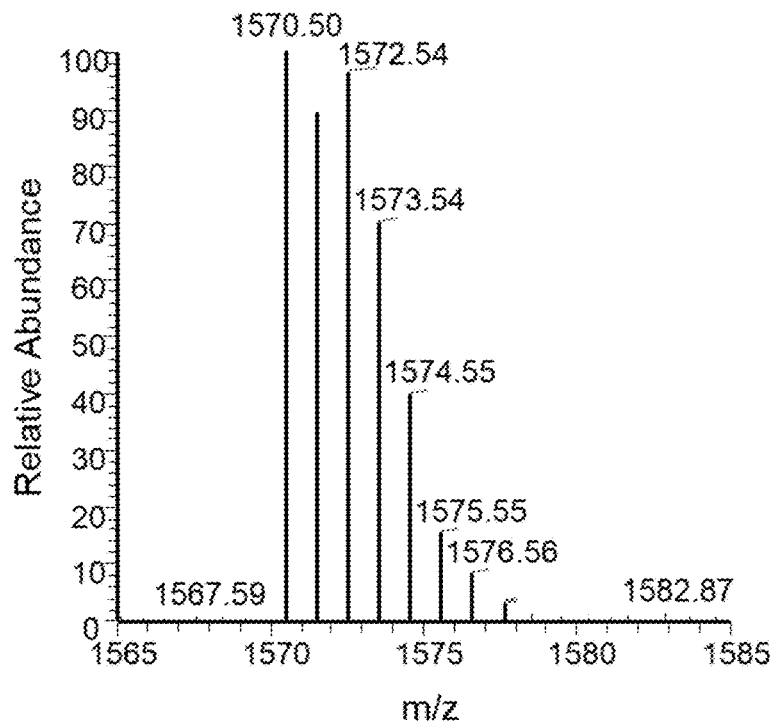
FIG. 1O: compound 24.
Figure 1P:
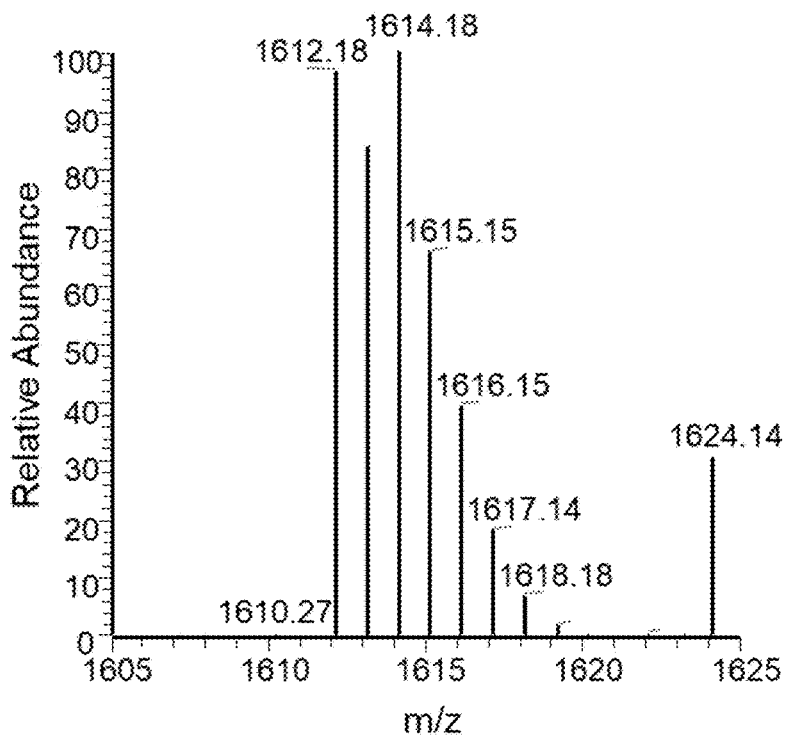
FIG. 1P: compound 25.
Figure 1Q:
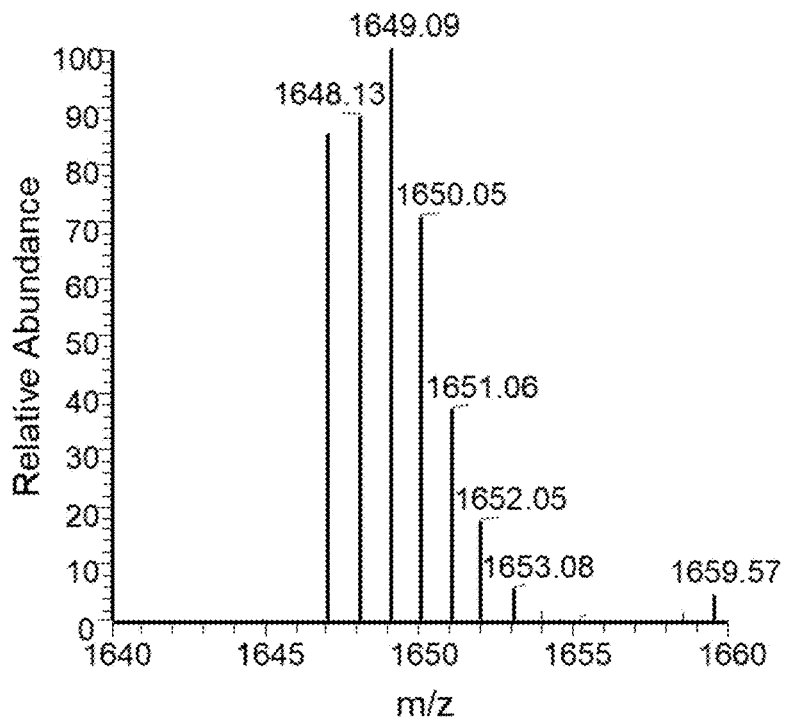
FIG. 1Q: compound 26.
Figure 1R:
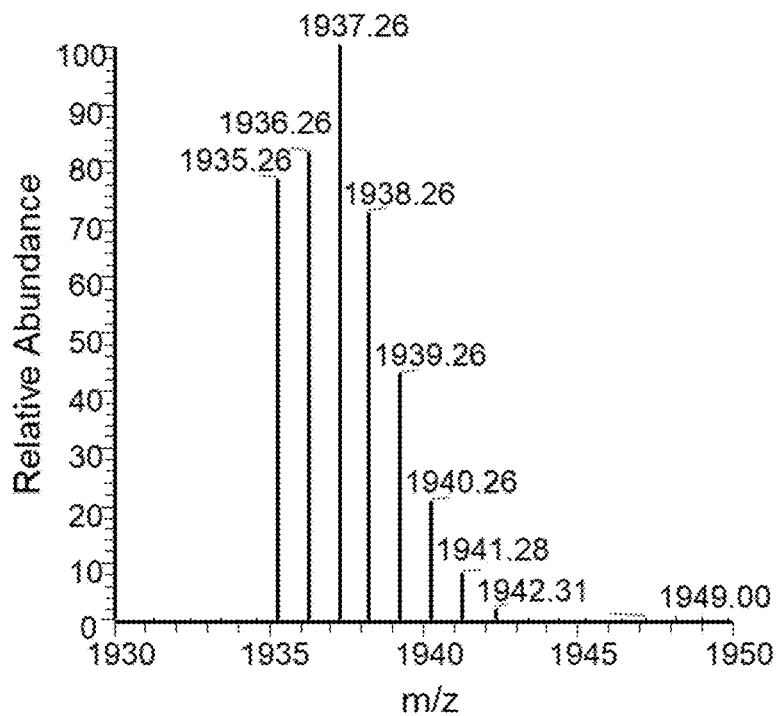
FIG. 1R: compound 27.
Figure 1S:
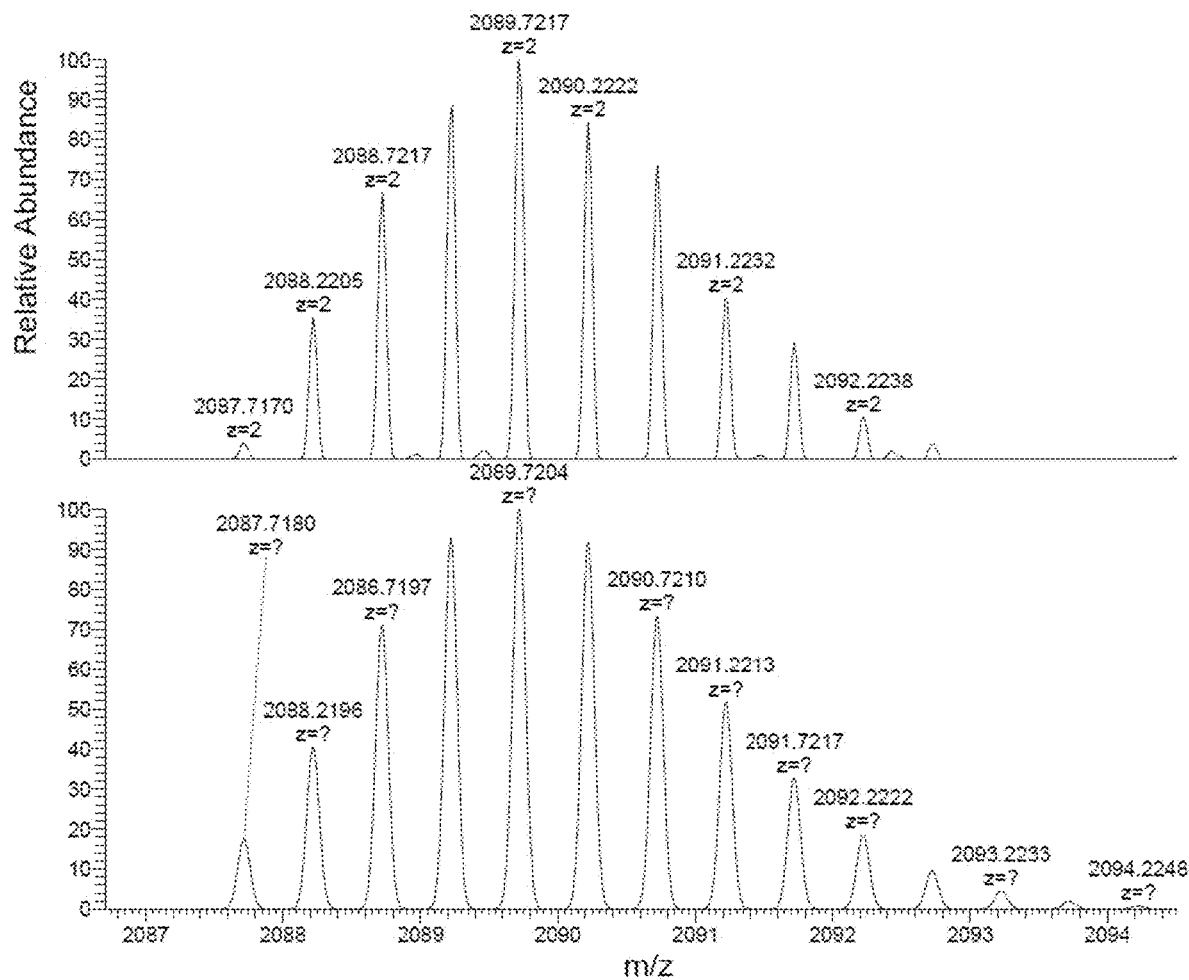
FIG. 1S: compound 29.
Figure 1T:
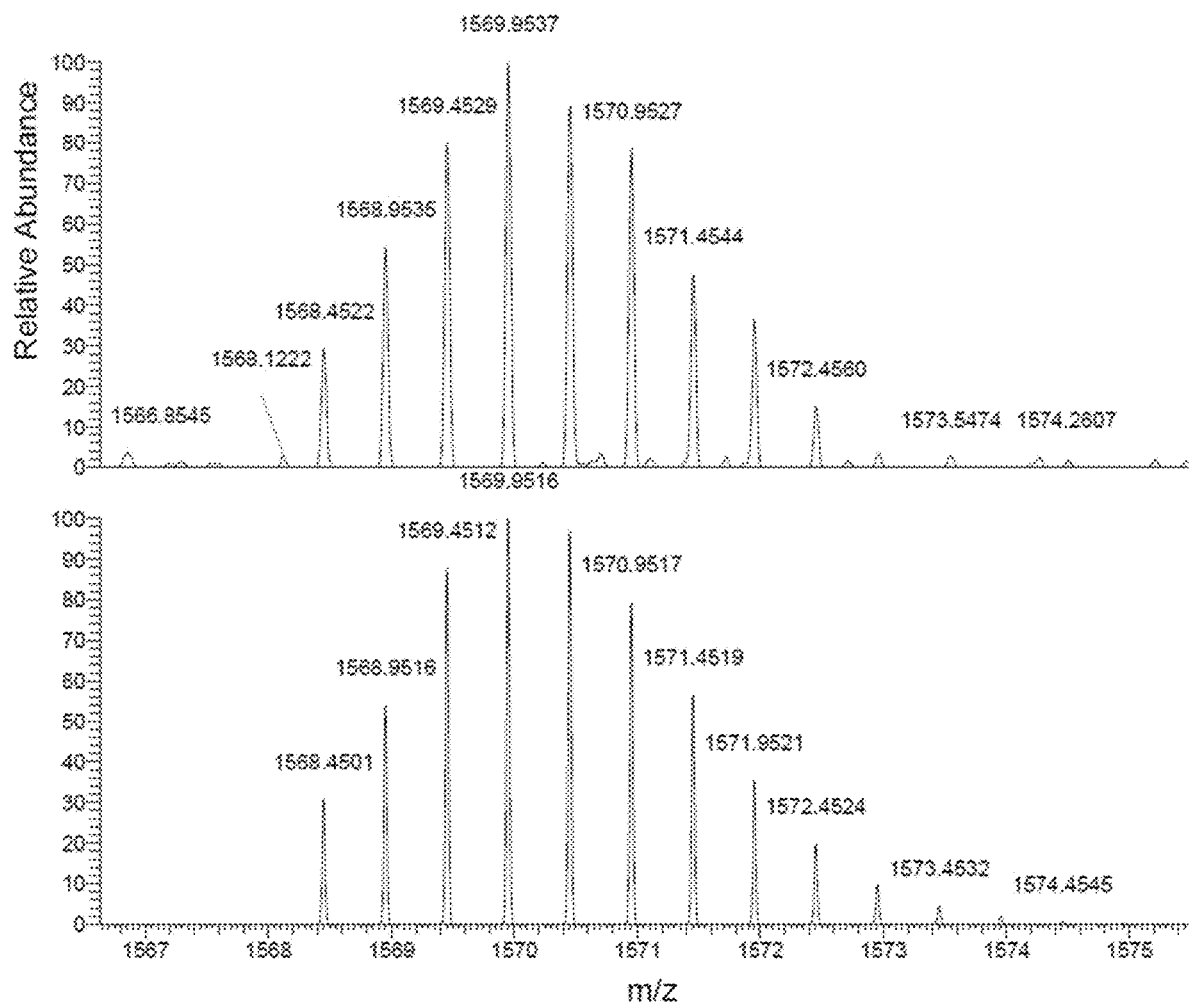
FIG. 1T: compound 30.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

Unless otherwise indicated, the term "alkyl" means a straight chain, branched and/or cyclic ("cycloalkyl") hydrocarbon having from 1 to 20 (e.g., 1 to 10, 1 to 9, 1 to 8, 1 to 7, 1 to 6, 1 to 5, 1 to 4, 1 to 3, 1 to 2, or 1) carbon atoms. Alkyl moieties having from 1 to 4 carbons ($C_{1-4}$ alkyl) are referred to as "lower alkyl." Examples of alkyl groups include methyl, ethyl, propyl, isopropyl, n-butyl, t-butyl, isobutyl, 2-isopropyl-3-methyl butyl, pentyl, pentan-2-yl, hexyl, isohexyl, heptyl, heptan-2-yl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, and cyclohexyl. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is substituted $C_{1-6}$ alkyl. In some embodiments, cycloalkyl is a monocyclic, saturated carbocyclyl group having from 3 to 6 ring carbon atoms ("$C_{3-6}$ cycloalkyl"). In some embodiments, a cycloalkyl group has 5 to 6 ring carbon atoms ("$C_{5-6}$ cycloalkyl"). Examples of $C_{5-6}$ cycloalkyl groups include cyclopentyl ($C_5$) and cyclohexyl ($C_6$). Unless otherwise specified, each instance of a cycloalkyl group is independently unsubstituted (an "unsubstituted cycloalkyl") or substituted (a "substituted cycloalkyl") with one or more substituents.

As used herein, the term "cycloalkyl" refers to a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydronaphthalinyl (i.e., tetralinyl), indenyl, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

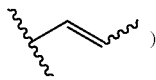

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

Unless otherwise indicated, the term "aryl" means an aromatic ring or a partially aromatic ring system composed of carbon and hydrogen atoms. An aryl moiety may comprise multiple rings bound or fused together. Examples of aryl moieties include phenyl, naphthyl, pyrenyl, anthryl, and phenanthryl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is a substituted phenyl (e.g., benzyl).

Unless otherwise indicated, the term "heteroaryl" means an aryl moiety wherein at least one of its carbon atoms has been replaced with a heteroatom (e.g., N, O or S). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 10-membered heteroaryl groups containing two heteroatoms include, without limitation, quinazolinyl.

Unless otherwise indicated, the terms "halogen" and "halo" encompass fluorine (fluoro, —F), chlorine (chloro, —Cl), bromine (bromo, —Br), and iodine (iodo, —I).

Unless otherwise indicated, the term "alkoxy" means an —O-alkyl group. Examples of alkoxy group include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl), such as —OCH$_3$ and —OCH$_2$CH$_3$.

As used herein, the term "acyl donor" refers to a molecule that has one or more acyl groups and may donate said acyl group(s) to a substrate (i.e., acyl acceptor) in an acyltransferase reaction. Each acyl group is independently unsubstituted (an "unsubstituted acyl") or substituted (a "substituted acyl") with one or more substituents.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, —OH, —CHO, —NH$_2$, —NH$_3^+$ alkoxy, alkanoyloxy (e.g., —OAc), alkenyl, alkynyl, alkyl (e.g., methyl, ethyl, propyl, t-butyl), cycloalkyl, aryl, heteroaryl, aryloxy, halo, and haloalkyl (e.g., —CCl$_3$, —CF$_3$, —C(CF$_3$)$_3$). According to some embodiments of the present disclosure, the substituent is halogen, alkoxy, C$_{1-6}$ alkyl, C$_{1-6}$ alkenyl, C$_{1-6}$ alkynyl, cycloalkyl, aryl, heteroaryl, —OH, —NH$_3^+$, —NHR$_c$ or

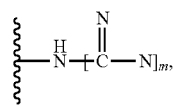

wherein R$_c$ is hydrogen or C$_{1-10}$ alkyl, and m is an integer from 1 to 5. The present disclosure is not intended to be limited in any manner by the above exemplary listing of substituents.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrate, ethanolate, and methanolate.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

As used herein, the term "derivative" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

For purpose of this invention, heteroatoms such as nitrogen may have hydrogen substituents and/or any suitable substituents as described herein which satisfy the valences of the heteroatoms and result in the formation of a stable moiety.

The term "treating" encompasses partially or completely ameliorating, mitigating and/or managing a symptom, a secondary disorder or a condition associated with bacterial infection. The term "treating" as used herein refers to application or administration of one or more compounds of the present disclosure to a subject, who has a symptom, a secondary disorder or a condition associated with bacterial infection, with the purpose to partially or completely alleviate, ameliorate, relieve, delay onset of, inhibit progression of, reduce severity of, and/or reduce incidence of one or more symptoms, secondary disorders or features associated with bacterial infection. Symptoms, secondary disorders, and/or conditions associated with bacterial infection include, but are not limited to, redness, swollen, pain, fever, chills, abscess, cellulitis, impetigo, toxic shock syndrome, malaise, fatigue, headache, rash, coughing, sneezing, inflammation, nausea, vomiting, diarrhea, fatigue, and cramping. Treatment may be administered to a subject who exhibits only early signs of such symptoms, disorder, and/or condition for the purpose of decreasing the risk of developing the symptoms, secondary disorders, and/or conditions associated with bacterial infection. Treatment is generally "effective" if one or more symptoms or clinical markers are reduced as that term is defined herein. Alternatively, a treatment is "effective" if the progression of a symptom, disorder or condition is reduced or halted.

The term "effective amount" as used herein refers to the quantity of a component or medicament which is sufficient to yield a desired "effective treatment" as defined hereinabove. The specific therapeutically effective amount will vary with factors such as the particular condition being treated, the physical condition of the patient (e.g., the patient's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects. Effective amount may be expressed, for example, as the total mass of the medicament (e.g., in grams, milligrams or micrograms) or a ratio of mass of the medicament to body mass, e.g., as milligrams per kilogram (mg/kg). Persons having ordinary skills could calculate the human equivalent dose (HED) for the medicament (such as the compounds of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to an animal including the human species that is treatable with the compounds of the present disclosure. The term "subject" is intended to refer to both the male and female gender unless one gender is specifically indicated, and may be any age, e.g., a child or adult.

II. Description of the Invention

II-(1) Novel Compounds

The subject invention provides compounds of formula (I), compositions or medicaments comprising one or more compounds of formula (I), and therapeutic uses thereof in preventing and/or treating infectious diseases:

(I)

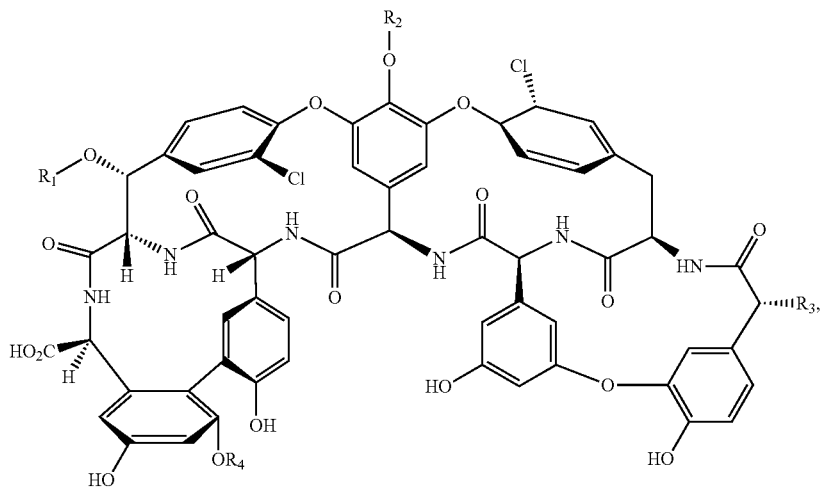

wherein, each $R_1$ and $R_2$ is independently H,

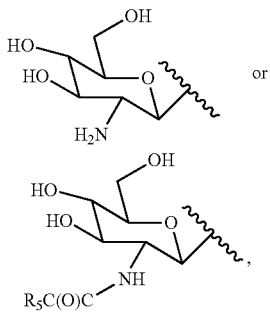

wherein $R_5$ is selected from the group consisting of, H, alkyl, alkenyl, alkynyl, and aryl;

$R_3$ is —$N(R_a)(R_b)$, wherein each $R_a$ and $R_b$ is independently H or alkyl;

$R_4$ is H or

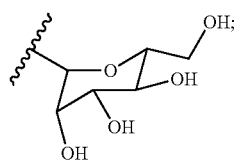 [SMILES: *C1OC(CO)C(O)C(O)C1O]

and each alkyl, alkenyl, alkynyl and aryl is optionally substituted by halogen, alkoxy, $C_{1-6}$ alkyl, $C_{1-6}$ alkenyl, $C_{1-6}$ alkynyl, cycloalkyl, aryl, heteroaryl, —OH, —$NH_3^+$, —$NHR_c$ or

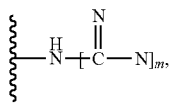

wherein $R_c$ is hydrogen or $C_{1-10}$ alkyl, and m is an integer from 1 to 5.

Additionally, salts, solvates, derivatives and prodrugs of the compounds of formula (I) also are included in the present disclosure and can be used in the composition and/or methods disclosed herein. The present disclosure further includes all possible stereoisomers and geometric isomers of the compounds of formula (I). The present invention includes both racemic compounds and optically active isomers. When a compound of formula (I) is desired as a single enantiomer, it can be obtained either by resolution of the final product or by stereospecific synthesis from either isomerically pure starting material or use of a chiral auxiliary reagent. Resolution of the final product, an intermediate, or a starting material can be achieved by any suitable method known in the art. Additionally, in situations where tautomers of the compounds of formula (I) are possible, the present disclosure is intended to include all tautomeric forms of the compounds. Prodrugs of compounds of formula (I) also are included in the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound. Suitable prodrugs include, for example, acid derivatives, such as amides and esters.

In certain embodiments, $R_1$ and $R_2$ are independently H,

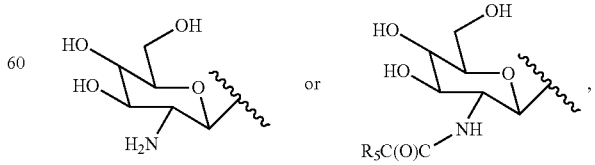

wherein $R_5$ is C—C≡C, or $C_1$-$C_{12}$ alkyl optionally substituted by —OH, —$NH_2$, —$NH_3^+$, aryl, aryl halogen, or

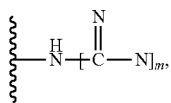

and m is an integer from 1 to 5;

R₃ is —N(Rₐ)(Rᵦ), wherein each Rₐ and Rᵦ is independently H or alkyl; and

R₄ is H or

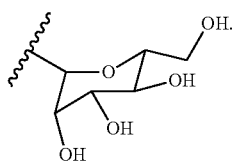 [SMILES: *C1OC(CO)C(O)C(O)C1O]

According to some embodiments,

R₁ is H;

R₂ is

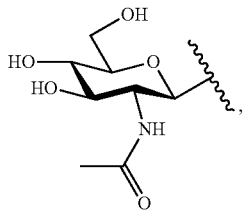

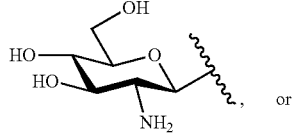, or

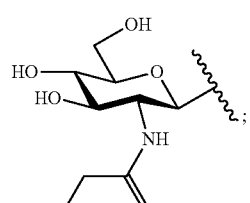

R₃ is —N(Rₐ)(Rᵦ), wherein Rₐ and Rᵦ are independently H or methyl; and

R₄ is H or

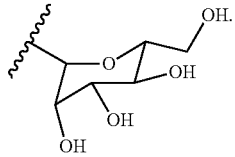 [SMILES: *C1OC(CO)C(O)C(O)C1O]

According to some embodiments,

R₁ is H,

 or 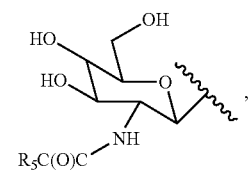, wherein R₅ is C—C≡C, or C₁-C₁₂ alkyl optionally substituted by —OH, —NH₂, —NH₃⁺, aryl, aryl halogen, or

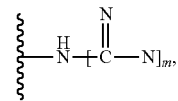

and m is an integer from 1 to 5;

R₂ is H;

R₃ is —N(Rₐ)(Rᵦ), wherein Rₐ and Rᵦ are independently H or methyl; and

R₄ is H or

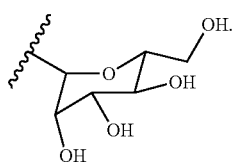 [SMILES: *C1OC(CO)C(O)C(O)C1O]

Exemplary compounds of formula (I) include, but are not limited to, the following,
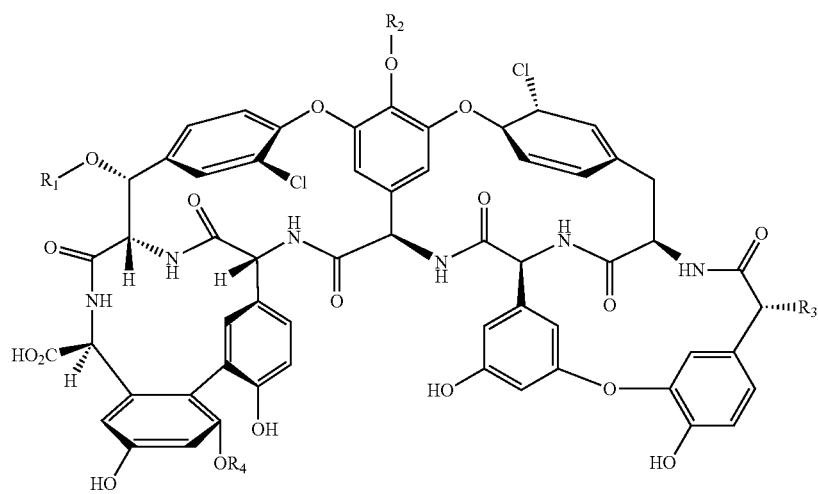
| Compound No. | R¹ | R² | R³ | R⁴ |
|---|---|---|---|---|
| 3 | (amino sugar with N-decanoyl acyl chain) | H | —N(CH$_3$)$_2$ | H |
| 4 | H | H | —NH$_2$ | H |
| 5 | H | (N-acetyl glucosamine sugar) | —NH$_2$ | H |
| 6 | H | H | —NH$_2$ | (glucosamine sugar) |

-continued
| Compound No. | R¹ | R² | R³ | R⁴ |
|---|---|---|---|---|
| 7 | H | 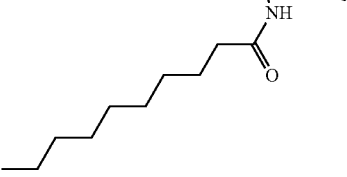 | —NH₂ | H |
| 8 | H | 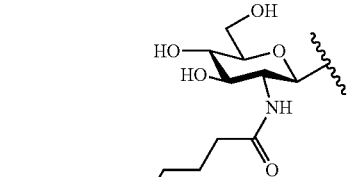 | —NH(CH₃) | H |
| 9 | 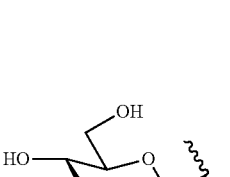 | H | —NH₂ | H |
| 10 | 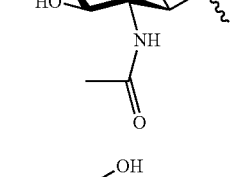 | H | —N(CH₃)₂ | H |
| 11 | 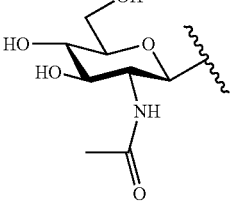 | H | —N(CH₃)₂ | H |
| 12 | 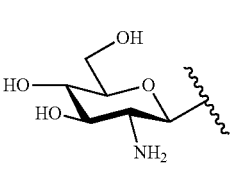 | H | —NH₂ | H |
| 13 | 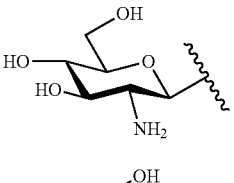 | H | —NH₂ | H |

-continued
| Compound No. | R¹ | R² | R³ | R⁴ |
|---|---|---|---|---|
| 14 | 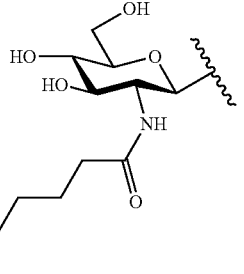 | H | —NH₂ | H |
| 15 | 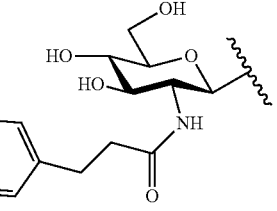 | H | —NH₂ | H |
| 16 | 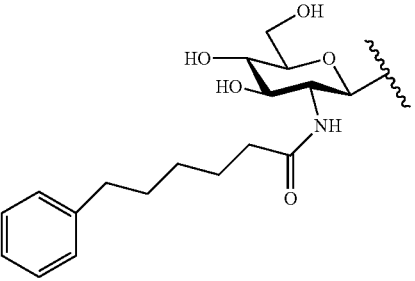 | H | —NH₂ | H |
| 17 | 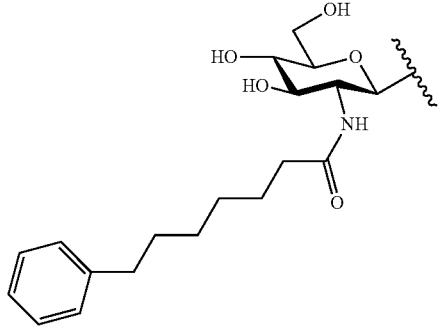 | H | —NH₂ | H |
| 18 | 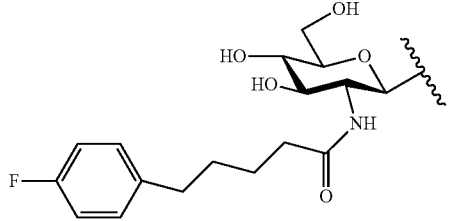 | H | —NH₂ | H |

-continued

| Compound No. | R¹ | R² | R³ | R⁴ |
|---|---|---|---|---|
| 19 | sugar with N-linked acyl chain terminating in -OH (hydroxyl on C10 chain) | H | —NH₂ | H |
| 20 | sugar with N-linked octanoyl chain | H | —N(CH₃)₂ | H |
| 21 | sugar with N-linked acyl chain terminating in -OH | H | —N(CH₃)₂ | H |
| 22 | sugar with N-linked acyl chain terminating in -NH₂ | H | —N(CH₃)₂ | H |
| 23 | sugar with N-linked acyl chain terminating in -N⁺(CH₃)₃ | H | —N(CH₃)₂ | H |

-continued

| Compound No. | R¹ | R² | R³ | R⁴ |
|---|---|---|---|---|
| 24 | | H | —N(CH₃)₂ | H |
| 25 | | H | —N(CH₃)₂ | H |
| 26 | | H | —NH₂ | |
| 27 | | | —N(CH₃)₂ | |

II-(2) Methods of Preparing Compounds of the Instant Invention

The following synthetic schemes are representative of the reactions suitable for synthesizing the compound of formula (I). Modifications and alternate schemes to prepare compounds of the present disclosure are readily within the capabilities of persons skilled in the art.

Compounds 7 and 8

According to certain embodiments, compounds 7 and 8 are prepared in accordance with Scheme 1.

Scheme 1 Synthesis of compounds 7 and 8
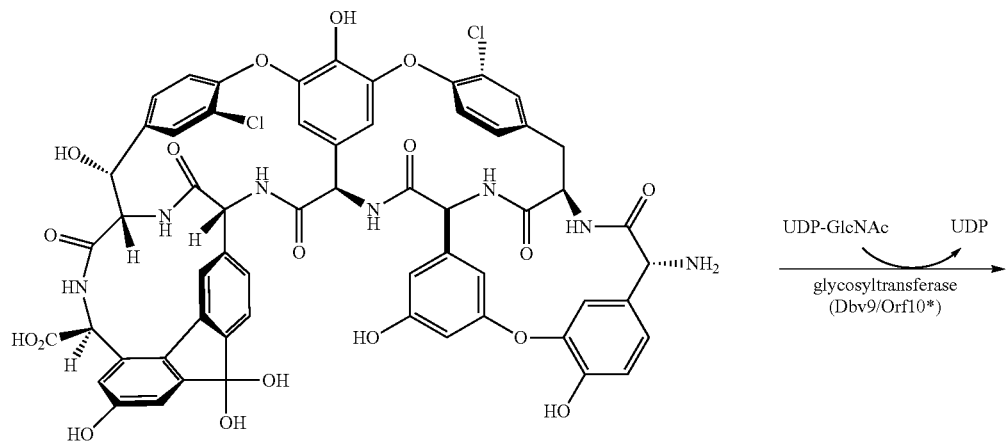
4
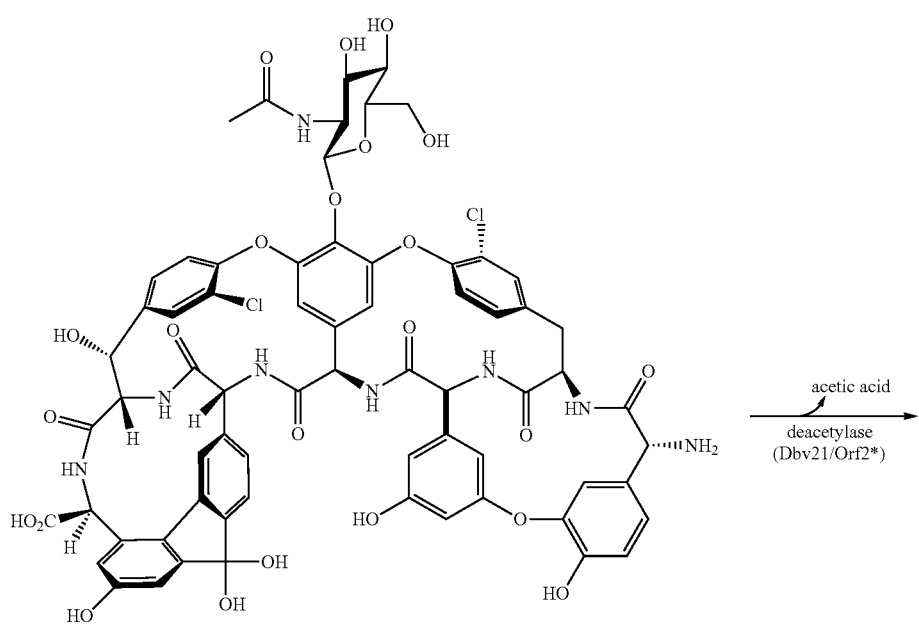
5

-continued
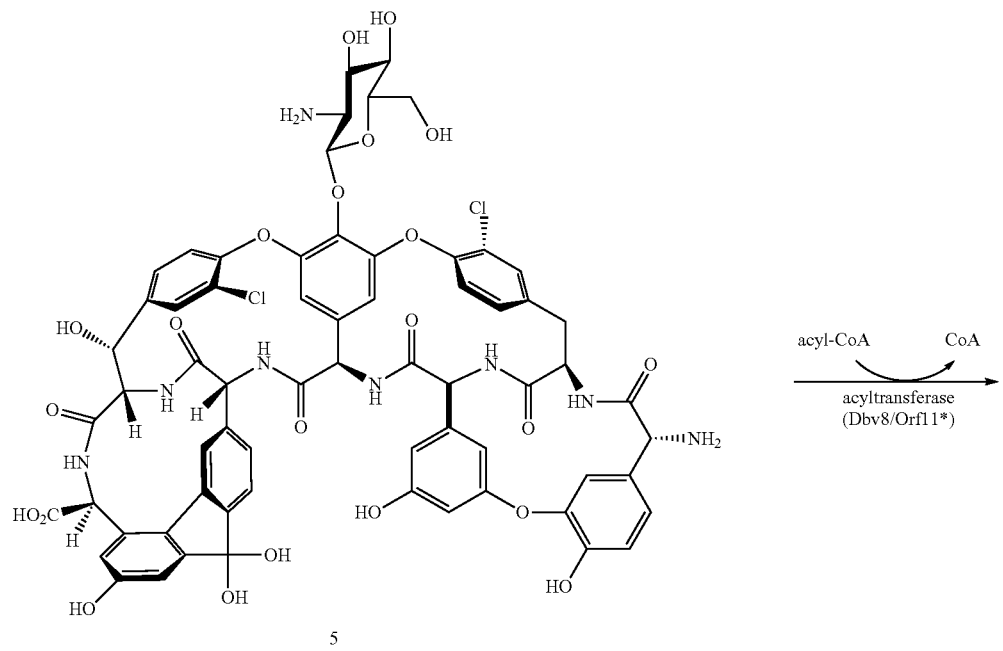
5
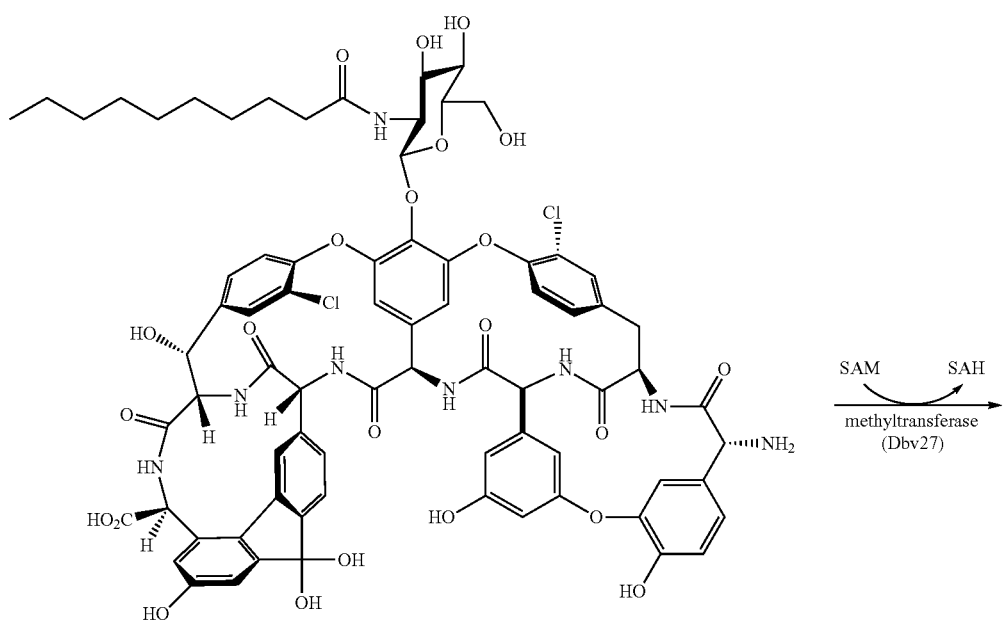
7

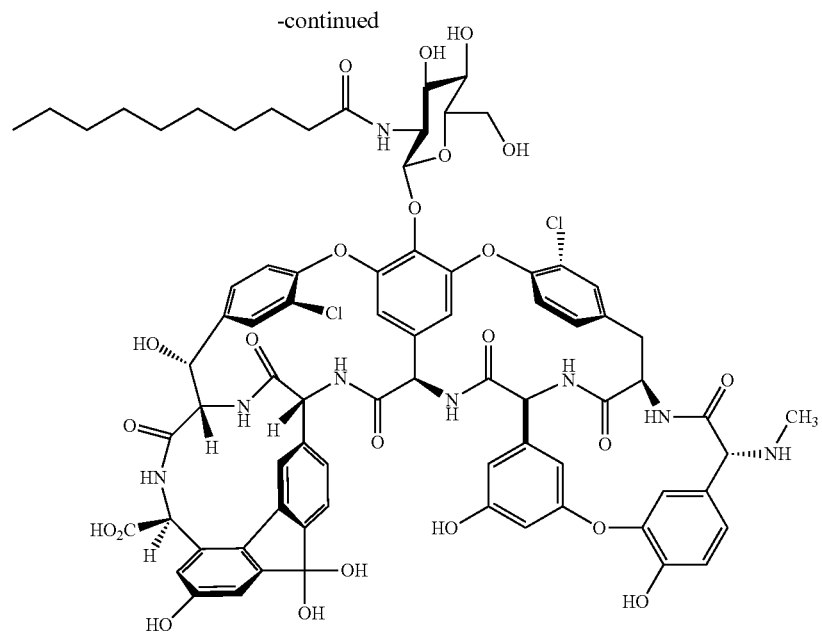

8

Specifically, the method depicted in scheme 1 includes the steps of,
- (a-1) glycosylating compound 4 with the aid of a glycosyltransferase in the presence of an acylated glycan to produce compound 5;
- (a-2) deacylating compound 5 with the aid of a deacylase to produce compound 6; and
- (a-3) acylating compound 6 with the aid of an acyltransferase in the presence of an acyl donor thereby producing compound 7.

In the step (a-1), compound 4 is glycosylated via mixing with a glycosyltransferase in the presence of an acylated glycan. The acylated glycan is a glycan having one or more acyl groups, in which the glycan may optionally be conjugated/linked with a nucleotide diphosphate (NDP). According to one working embodiment, the acylated glycan is conjugated/linked with uridine (i.e., as a form of uridine diphosphate N-acetylglucosamine (UDP-GlcNAc)). Regarding the glycosyltransferase, it may be any enzyme exhibiting a catalyzing activity on the formation of glycosidic linkage; exemplary glycosyltransferases include, but are not limited to, CalB, CalE, CalN, CalU, Gra orf14, Gra orf5, LanGT1, LanGT2, LanGT3, LanGT4, MtmGI, MtmGII, MtmGTIII, MtmGTIV, NovM, RhlB, Rif orf 7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gpl-1, Gpl-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD, and the homolog/variant/derivative thereof. According to some preferred embodiments, the glycosyltransferase comprises the amino acid sequence of SEQ ID NO: 1, which catalyzes the transfer of acylated glycosyl group (e.g., GlcNAc) from the acylated glycan (e.g., UDP-GlcNAc) to residue 4 (r4) position of compound 4. The thus-obtained product is designated as compound 5.

Next, in the step (a-2), compound 5 is deacylated by use of a deacylase, in which the acyl group from the r4 position is removed and thereby gives rise to a deacylated compound 6. Any deacylase exhibiting a deacylation activity may be employed in the present method. Preferably, the deacylase suitable for the step (a-2) comprises the amino acid sequence of SEQ ID NO: 2.

In the step (a-3), compound 6 is subjected to the treatment of an acyltransferase in the presence of an acyl donor. The acyltransferase is characterized in possessing acyl-transferring activity that catalyzes the transfer of an acyl group from an acyl donor to an acyl acceptor. Examples of acyltransferase suitable for use in the present disclosure include, but are not limited to, lysophosphatidic acid acyltransferase (LPAT), phospholipid diacyl glycerol acyl transferase acyltransferase (PDAT), diacylglycerol acyltransferase (DGAT), acyl-CoA:1-acyl lysophosphatidylcholine acyltransferase (LPCAT), glycerol-3-phosphate acyltransferase (GPAT), lysophosphatidic acid acyltransferase (LPAAT), and the homolog/variant/derivative thereof. Depending on desired purposes, the acyl donor may be any natural or synthetic molecule, which donates an acyl group to a chemical substrate (i.e., acyl acceptor). Exemplary acyl donors commonly used in the art include, acetyl coenzyme A (acetyl-CoA), acyl-CoA, butyrlyl-CoA, benzoyl-CoA, acetoacetyl CoA, β-hydroxybutyryl-CoA, malonyl-CoA and palmitoyal-CoA. Alternatively, the acyl donor may be a compound comprising a group of formula —C(O)CR$_5$, wherein R$_5$ is as defined above. According to some preferred embodiments of the present disclosure, the acyltransferase comprises the amino acid sequence of SEQ ID NO: 3, which catalyzes the transfer of acyl group from the acyl donor (e.g., acyl-CoA) to the acyl acceptor (e.g., compound 6) thereby producing compound 7.

Optionally, the present method further comprises a step of reacting the product of step (a-4) (i.e., compound 7) with a methyltransferase so as to produce compound 8. The methyltransferase is an enzyme catalyzing the transfer of a methyl group from a methyl donor to a methyl acceptor. In general, the methyltransferase includes class I methyltransferase (i.e., a methyltransferase containing a Rossman fold for binding S-Adenosyl methionine (SAM)), class II methyltransferase (i.e., a methyltransferase containing a SET domain), and class III methyltransferase (i.e., a membrane associated methyltransferase). According to some embodiments of the present disclosure, the methyltransferase employed in the present method is class I methyltransferase. In one preferred embodiment, the methyltransferase comprises the amino acid sequence of SEQ ID NO: 4, which catalyzes the transfer of a methyl group from the methyl donor (e.g., SAM) to the methyl acceptor (e.g., compound 7).

Compounds 3 and 20-25

According to certain embodiments, compounds 3 is prepared in accordance with the method depicted in Scheme 2.

Scheme 2 Synthesis of compound 3

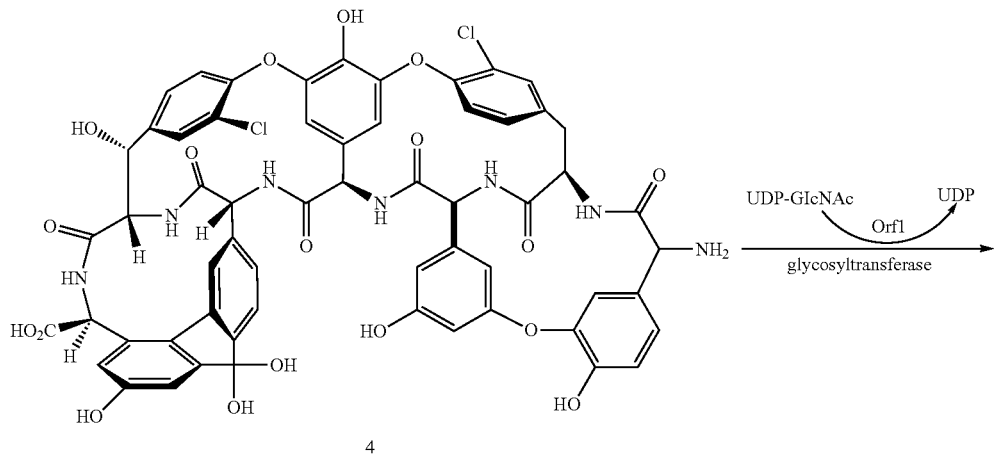

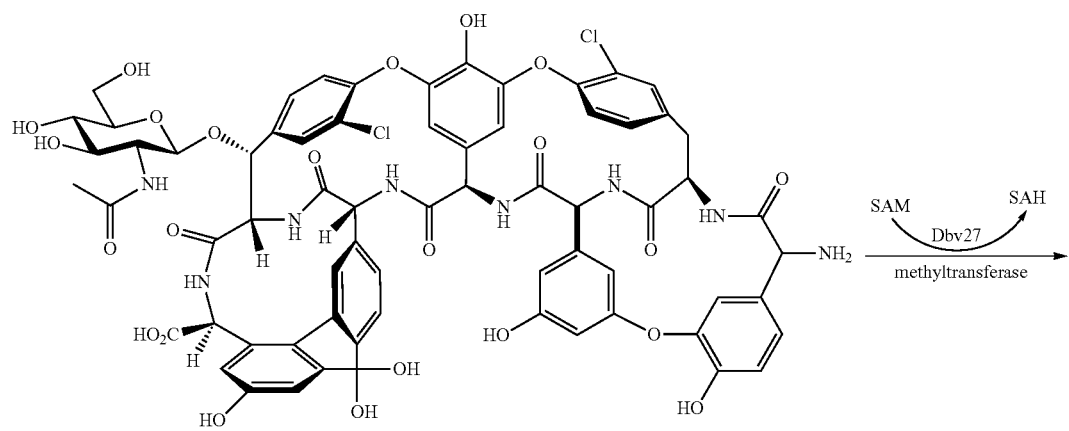

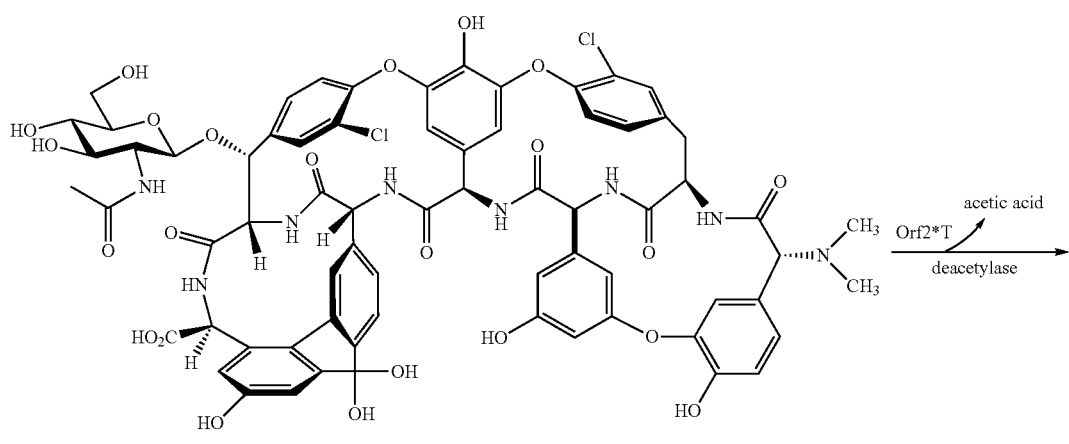

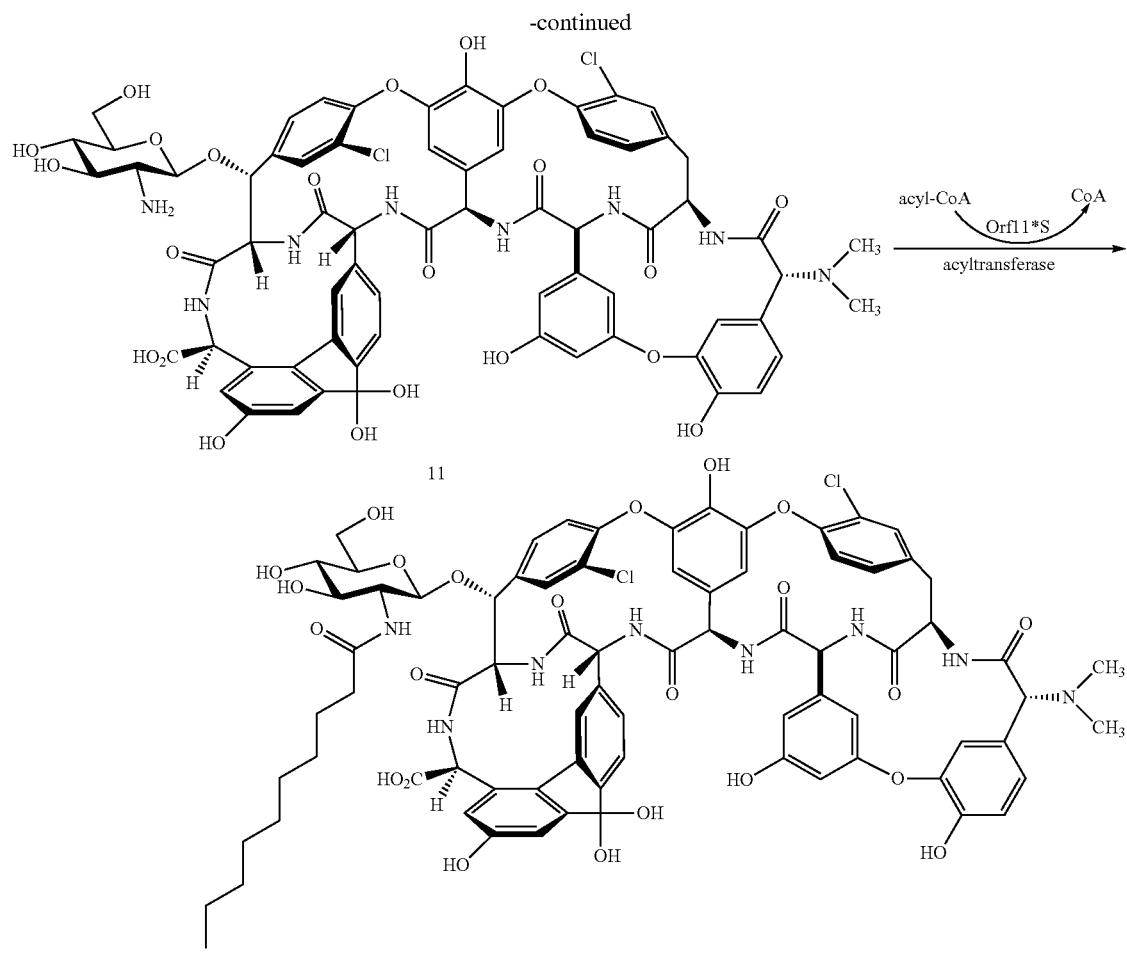

3

Specifically, the method depicted in scheme 2 includes the steps of, (b-1) glycosylating compound 4 with the aid of a glycosyltransferase in the presence of an acylated glycan to produce compound 9;
(b-2) methylating compound 9 with the aid of a methyltransferase to produce compound 10;
(b-3) deacylating compound 10 with the aid of a deacylase to produce compound 11; and
(b-4) acylating compound 11 with the aid of an acyltransferase in the presence of an acyl donor thereby producing compound 3.

The process for preparing compound 3 is quite similar to those for compounds 7 and 8; hence, detailed description thereof is omitted herein for the sake of brevity. According to certain preferred embodiments of the present disclosure, the glycosyltransferase in the step (b-1) comprises the amino acid sequence of SEQ ID NO: 5; the methyltransferase in the step (b-2) comprises the amino acid sequence of SEQ ID NO: 4; the deacylase in the step (b-3) comprises the amino acid sequence of SEQ ID NO: 6; and the acyltransferase in the step (b-4) comprises the amino acid sequence of SEQ ID NO: 7.

As defined/described above, the acyl donor is a molecule capable of donating an acyl group to a chemical substrate (i.e., acyl acceptor), in which the acyl group may be unsubstituted (an "unsubstituted acyl") or substituted (a "substituted acyl") with one or more substituents. Preferably, the acyl donor in the instant method is a compound comprising a function group of —C(O)CR$_5$, wherein R$_5$ is as defined above. The identity of the acyl donor in the step (b-4) may vary with the desired purpose. In general, compounds 20-25 may be prepared by similar manner via replacing acyl-CoA of the step (b-4) with other suitable acyl donors. For example, in the preparation of compound 22, the compound of formula (II) is employed as the acyl donor to donate the acyl group to compound 11; while the compound of formula (III) may serves as the acyl donor for the preparation of compound 23:

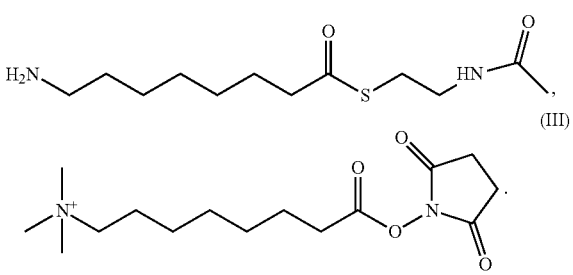

In addition to the process described above, compounds 24 and 25 may alternatively be prepared via guanylating the lipid side chain (i.e., adding a guanidine or di-guanidine to the lipid side chain) at residue 6 (r6) position of compound 22 as depicted in scheme 3.

Scheme 3 Synthesis of compounds 24 and 25 via guanylation reaction

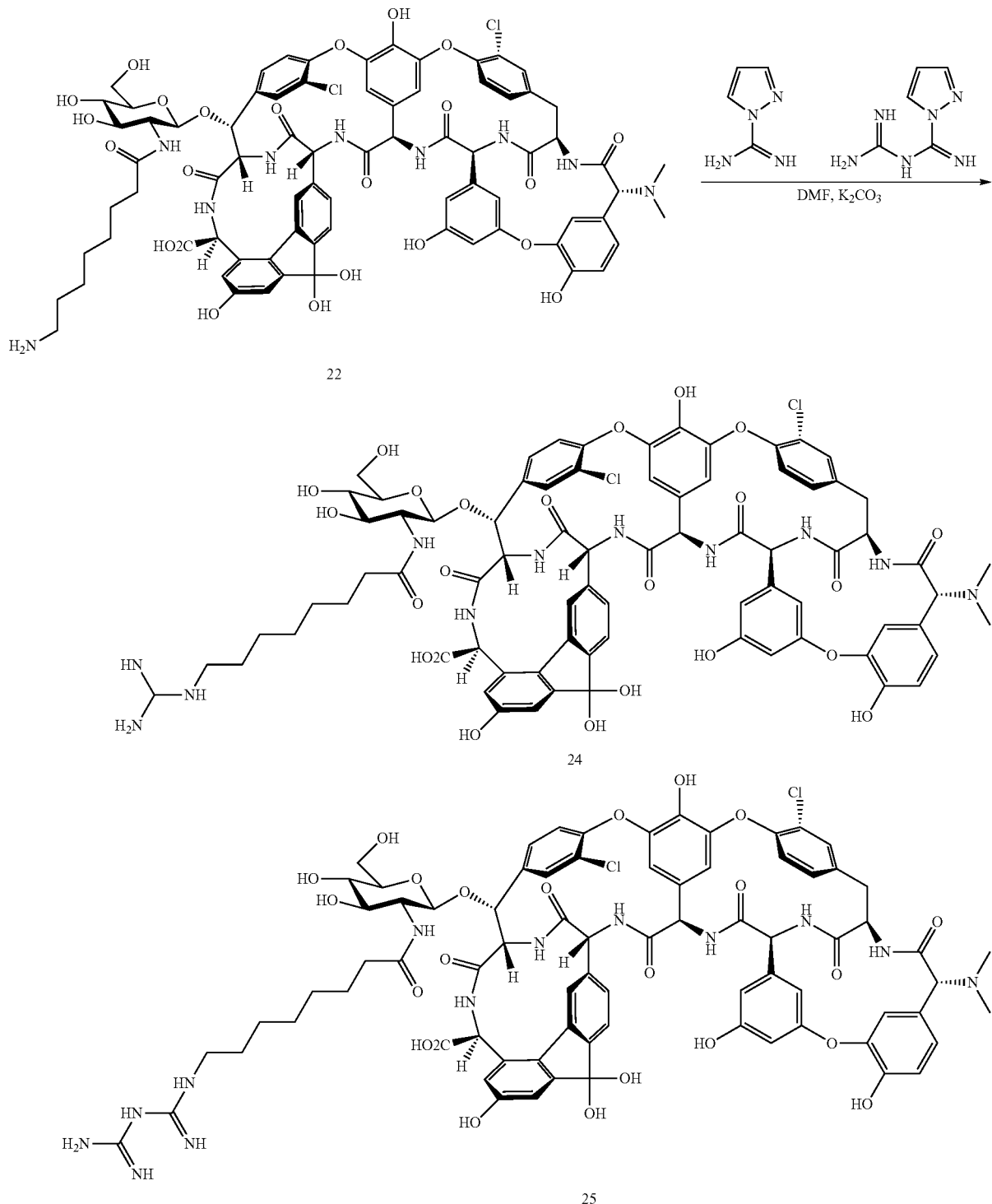

Compounds 13-19

The method for producing compounds 13-19 comprises the steps of, (c-1) glycosylating compound 4 with the aid of a glycosyltransferase in the presence of an acylated glycan to produce compound 9;

(c-2) deacylating compound 9 with the aid of a deacylase to produce compound 12; and (c-3) acylating compound 12 with the aid of an acyltransferase in the presence of an acyl donor thereby producing compounds 13-19.

According to some working examples of the present disclosure, the glycosyltransferase in the step (c-1) comprises the amino acid sequence of SEQ ID NO: 5; the deacylase in the step (c-2) comprises the amino acid sequence of SEQ ID NO: 6; and the acyltransferase in the step (c-3) comprises the amino acid sequence of SEQ ID NO: 7. Other than the features mentioned above, the process for preparing compounds 13-19 is quite similar with that of compound 7; hence, detailed description thereof is omitted herein for the sake of brevity.

II-(3) Pharmaceutical Compositions or Medicaments Comprising the Compound of Formula (I)

According to some embodiments of the present disclosure, the compound of formula (I) exhibits an inhibitory effect on bacteria, including gram-negative and gram-positive bacteria. The third aspect of the present invention thus pertains to a pharmaceutical composition or medicament for treating infectious diseases. The present pharmaceutical composition or medicament comprises at least one of the compound of formula (I), or its pharmaceutically acceptable salt, solvate, stereoisomer, derivative or prodrug, and a pharmaceutically acceptable excipient.

The compound of formula (I)/pharmaceutically acceptable salt, solvate, stereoisomer, derivative or prodrug of the compound of formula (I) is present at a level of about 0.1% to 99% by weight, based on the total weight of the pharmaceutical composition or medicament. In some embodiments, the compound of formula (I)/pharmaceutically acceptable salt, solvate, stereoisomer, derivative or prodrug of the compound of formula (I) is present at a level of at least 1% by weight, based on the total weight of the pharmaceutical composition or medicament. In certain embodiments, the compound of formula (I)/pharmaceutically acceptable salt, solvate, stereoisomer, derivative or prodrug of the compound of formula (I) is present at a level of at least 5% by weight, based on the total weight of the pharmaceutical composition or medicament. In still other embodiments, the compound of formula (I)/pharmaceutically acceptable salt, solvate, stereoisomer, derivative or prodrug of the compound of formula (I) is present at a level of at least 10% by weight, based on the total weight of the pharmaceutical composition or medicament. In still yet other embodiments, the compound of formula (I)/pharmaceutically acceptable salt, solvate, stereoisomer, derivative or prodrug of the compound of formula (I) is present at a level of at least 25% by weight, based on the total weight of the pharmaceutical composition or medicament.

Certain pharmaceutical compositions or medicaments are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of single unit dosage forms include, but are not limited to: tablet, caplet, capsule (such as soft elastic gelatin capsule), cachet, troche, lozenge, dispersion, suppository, ointment, cataplasm (poultice), paste, powder, dressing, cream, plaster, solution, patch, aerosol (e.g., nasal spray or inhaler), and gel.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin or β-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil), lipids such as egg york phosphatidylcoline (EPC), soybean phosphatidylcholine (SPC), 1,2-dioleoyl-sn-glycero-3-phosphocholine (DOPC), 1,2-distearoyl-sn-glycero-3-phosphocholine (DSPC), cholesterol (CHO), dipalmitoylphosphatidylcholine (DPPC) and PEG-2000. According to one preferred embodiment, the compound of formula (I) (i.e., BO-2590) is incorporated into lipids to form liposomes suitable for oral or parenteral administration.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Pharmaceutically acceptable excipients used in the manufacture of provided pharmaceutical composition include inert diluent, dispersing and/or granulating agent, surface active agent and/or emulsifier, disintegrating agent, binding agent, preservative, buffering agent, lubricating agent, and/or oil. Excipients such as cocoa butter and suppository wax, coloring agent, coating agent, sweetening, flavoring, and perfuming agents may also be present in the composition.

II-(4) Medical Uses of the Present Compound, Pharmaceutical Composition and Medicament Also disclosed herein are methods of treating infectious diseases by use of the compound, pharmaceutical composition or medicament in accordance with any aspect or embodiment of the present disclosure. The method comprises administering to a subject in need thereof an effective amount of the present compound, pharmaceutical composition or medicament so as to alleviate or ameliorate the symptoms associated with bacterial infection.

In general, the infectious disease may be caused by and/or associated with a gram-positive bacterium (e.g., *Staphylococcus, Streptococcus, Bacillus, Clostridium, Corynebacterium* or *Listeria*) or a gram-negative bacterium (e.g., Enterobacteriaceae, *Pseudomonas, Moraxella, Helicobacter, Stenotrophomonas, Bdellovibrio,* acetic acid bacteria or *Legionella*). According to one embodiment of the present disclosure, the infectious disease is caused by/associated with *Staphylococcus aureus*. According to another embodiment of the present disclosure, the infectious disease is caused by/associated with Enterococci. According to still another embodiment of the present disclosure, the infectious disease is caused by *Acinetobacter baumannii.*

The bacterium may be an antibiotic-sensitive bacterium or an antibiotic-resistant bacterium. According to some working examples, the bacterium is resistant to methicillin or vancomycin.

According to some embodiments of the present disclosure, the present compounds may be used in combination with each other or with other anti-bacterial agents (for example, antibiotic or corticosteroid) so as to produce an additive or a synergistic effect on inhibiting the replication/activity/function of bacteria. Accordingly, the present compound, pharmaceutical composition or medicament can be used as the sole anti-bacterial agent, or in combination with another anti-bacterial treatment, e.g., kanamycin.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

Materials and Methods
Protein Expression and Purification

The genes orf1, orf10*, orf2* and orf11* were amplified from *Actinoplanes teichomyceticus* genomic DNAs (the teicoplanin producing strain) by polymerase chain reaction (PCR). The gene dbv27 was amplified from *Nonomuraea gerenzanensis* sp. nov. ATCC 39727 genomic DNAs (the A40926 producing strain) by PCR. The gene glmU was amplified from *Escherichia coli* K12 genomic DNAs by PCR. The gene nahK (lnpB) was amplified from the genomic DNAs of *Bifidobacterium longum* (JCM1217) by PCR. These amplified genes were respectively sub-cloned into the expression vector pET-28a (+) to provide an N-terminal His 6-tagged protein. In brief, the expression plasmids pET-28a and PCR products were respectively digested with restriction enzymes NdeI and XhoI at 37° C. for 5 hours. The digested plasmid and DNA were then ligated. The inserted genes of clones were checked by restriction-enzyme analysis and justified by agarose electrophoresis and DNA sequencing. Each gene product was expressed in *E. coli*, in which the expression was induced by addition of isopropyl-δ-d-1-thiogalactoside (IPTG) with a final concentration of 0.2 mM at 16° C. for 18 hours. The cells were harvested, disrupted, and centrifuged sequentially to remove cell debris. Each supernatant was loaded onto an $Ni^+$-NTA agarose resin column that was pre-equilibrated with a buffer solution (20 mM Tris at pH 8.0, 500 mM NaCl, 10% glycerol, 10 mM imidazole). Eluted protein was further purified by size exclusion chromatography. Protein purity was examined by SDS-PAGE and protein concentration was determined with BSA as a standard. The glycosyltransferases encoded by genes orf1 and orf10* respectively have the amino acid sequences of SEQ ID NOs: 5 and 1; the deacylase encoded by gene orf2* has the amino acid sequence of SEQ ID NO: 2; the acyltransferase encoded by gene orf11* has the amino acid sequence of SEQ ID NO: 3; and the methyltransferase encoded by gene dbv27 has the amino acid sequence of SEQ ID NO: 4.

Mutagenesis of Orf2* and Orf11*

Since the wild-type Orf2* in complex with Tei is available, the iterative saturation mutagenesis (ISM) would allow given sites to be substituted. On the basis of the solved crystal Orf2* complex, a number of positions in the binding site were targeted, including (1) R75; (2) D97/S98; (3) R116/Q117; (4) A120/V121; (5) H161/D163/H164; (6) Y190/F193. Six primer sets with NNK degeneracy were used to generate saturation mutagenesis libraries. Each lysate was screened for r6-deacetylation activity using LC/MS. Positive hits were further cross-pollinated with positive hits of other mutants to generate additive combinations. Each lysate from the combinations was screened by LC/MS for better r6-deacetylation activity.

For the acyltransferase Orf11*, the mutations were made through rational design. The residues W163, S182, A184 and G194 were respectively mutated to W163A, S182R, A184R and G194R. These mutants were then subjected to biochemical examination for mutants capable of acylating r6 position of Tei-pseudoaglycone. Mutagenesis was carried out by site-directed mutagenesis kit. The wild-type orf1, orf2* and orf11* were used as templates for site-directed mutagenesis, where corresponding primers were listed in Table 1. All mutations were confirmed by DNA sequencing. Mutated proteins were expressed and purified with the same protocol as described above.

TABLE 1

Primers for preparing Orf2* and Orf11* mutants

| Mutants | Sequence | SEQ ID NO |
|---|---|---|
| Orf2* | | |
| S98A | F5'-CCGGTTCCTCGACGCCATCTACCGTAAG | 8 |
| F193Y | F5'-CCGTATGCGGTCTACAAATCAGGTGCG | 9 |
| V121A | F5'-GGCAGAAGCTGGCCGCCAACGATCACTCGC | 10 |
| Orf11* | | |
| W163A | F5'-CGGCATGAACATGCAGGCCTGGACCACCTACCACC | 11 |
| S182R | F5'-CGGCCGCCTGCAATTCAGACTGGCCACCGGAAAGG | 12 |
| A184R | F5'-CCTGCAATTCAGTCTGCGCACCGGAAAGGACGGCA | 13 |
| G194R | F5'-CGGCACGCCGCACCTCCGCCTGCACGTTCCCGAGT | 14 |

The deacylase encoded by gene Orf2*T (a mutant having three-point mutations of S98A/V121A/F193Y) has the amino acid sequence of SEQ ID NO: 6, and the acyltransferase encoded by Orf11*S (a mutant having one point-mutation of W163A) has the amino acid sequence of SEQ ID NO: 7.

Compounds Characterization and Synthesis (1) Synthesis of Acyl-NAC and Coenzyme a Derivatives For the synthesis of compounds 13-21, acyl-NAC was first synthesized for subsequent enzymatic reactions. The reaction mixture containing N-acetylcysteamine (NAC) (1.0 mmol) and trimethylamine (TEA) (2.0 mmol) in dimethylformamide (DMF) was started with dropwise addition of acyl chloride (1.2 mmol) in stirring at room temperature. The reaction was quenched by adding aqueous $NH_4Cl$ and extracted twice with 5 mL ethyl acetate. The organic layer was dried and evaporated to give a white solid. The white residues were purified by silica gel chromatography (EA: hexane, 20:80) to yield pure acyl-NAC.

For compound 22, the Boc-protected amine of 8-aminooctanoic acid (LC-MS: m/z 258 [M−H]⁻) was first prepared: di-tert-butyl dicarbonate (152.6 mg, 0.7 mmol) was added dropwise to a solution of 8-aminooctanoic acid (100.2 mg, 0.63 mmol) in 1 N NaOH with stirring at room temperature overnight. The reactant was concentrated in vacuo and dried to white solid powders. The solid powders were resuspended in DCM for the 1-ethyl-3-(3-dimethylaminopropyl) carbodiimide (EDC)/N-hydroxysuccinimide (NETS) coupling reaction. EDC (12 mg, 0.06 mmol) and NETS (9.2 mg, 0.08 mmol) were mixed in DCM, followed by addition of Boc-protected 8-aminooctanoic acid (10 mg, 0.04 mmol) with stirring overnight to form N-Boc protected S-acyl-NAC. The product was purified by column chromatography and dried by lyophilization (LC-MS: m/z 361 [M+H]$^+$). The N-Boc deprotection was performed with addition of TFA/DCM (1:1) (Scheme 4) (LC-MS: m/z 261 [M+H]$^+$). Thioester exchange between acyl-NAC and CoA were performed to form acyl-CoA derivatives, which were stored for acyl-CoA-dependent acyltransferase (Orf11*) reactions.

Scheme 5 Synthesis of 7-carboxy-N,N,N-trimethylheptan-1-aminium

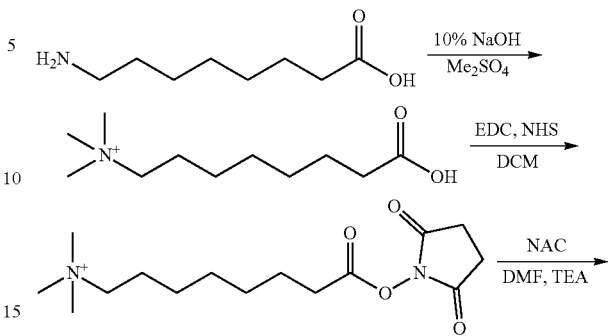

Scheme 4 Synthesis of acyl-NAC derivatives

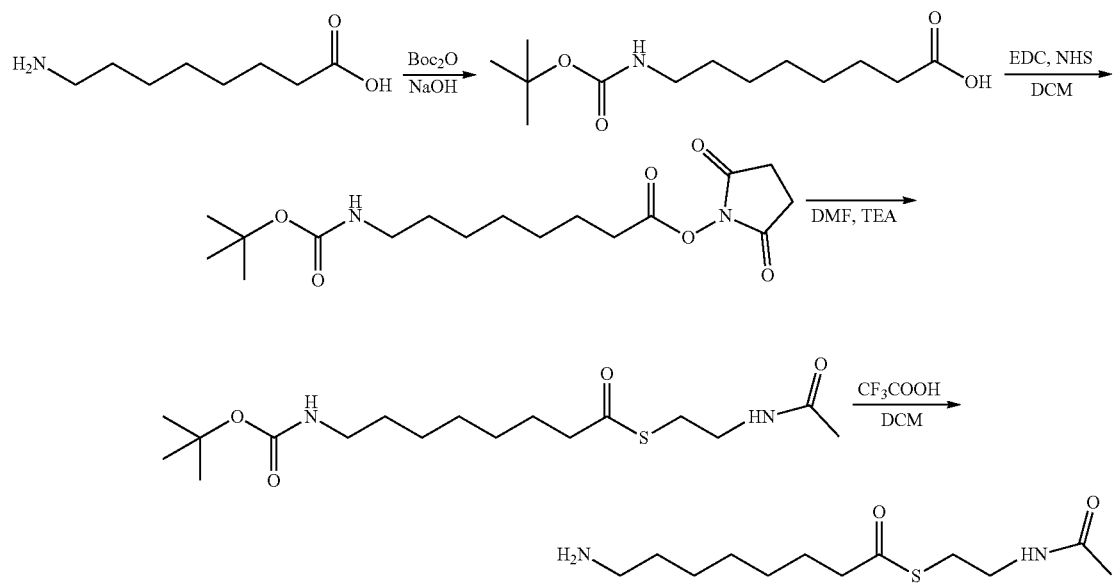

(2) Synthesis of 7-carboxy-N,N,N-trimethylheptan-1-aminium

For compound 23, 7-carboxy-N,N,N-trimethylheptan-1-aminium (LC-MS: m/z 202 [M]$^+$) was used as a starting material for acyl-NAC synthesis. The commercially available 8-aminooctanoic acid (70 mg, 0.43 mmol) was dissolved in 10% NaOH (4 mL), in which Me$_2$SO$_4$ (0.4 mL) was added and stirred at room temperature. The mixture was then neutralized by dropwise addition of HCl. The solvents were distilled off in vacuo and solid products left were washed with ether and dried sequentially. The white solids were resuspended in DCM. The EDC (12 mg, 0.06 mmol) and NHS (9.2 mg, 0.08 mmol) were mixed and immediately added with 7-carboxy-N,N,N-trimethylheptan-1-aminium (8 mg, 0.04 mmol) in stirring overnight. The product (LC-MS: m/z 299 [M]$^+$) was purified by column chromatography and dried by lyophilization (Scheme 5), where the synthetic protocol for the given NAC derivative was the same as the procedure described above (LC-MS: m/z 303 [M]$^+$).

-continued

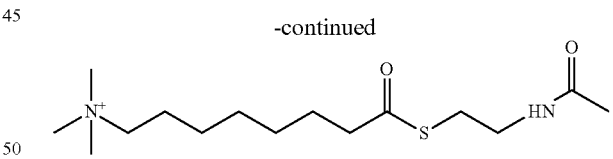

(3) Synthesis of N-carbamimidoyl-1H-pyrazole-1-carboximidamide hydrochloride

For compound 25, self-condensation of 1-guanyl-pyrazole hydrochloride was firstly prepared. Commercially available 1-guanyl-pyrazole hydrochloride (293 mg, 2.0 mmol) was dissolved in 0.5 mL DMF and followed by addition of DIPEA (0.348 mL, 2.0 mmol) as shown in Scheme 6. The mixture was stirred at room temperature for 64 hours. The solid products (LC-MS: m/z 153 [M+H]$^+$) formed were washed by ether. The products (yield: about 30%) were collected and dried for use.

Scheme 6
Synthesis of N-carbamimidoyl-1H-pyrazole-1-carboximidamide hydrochloride

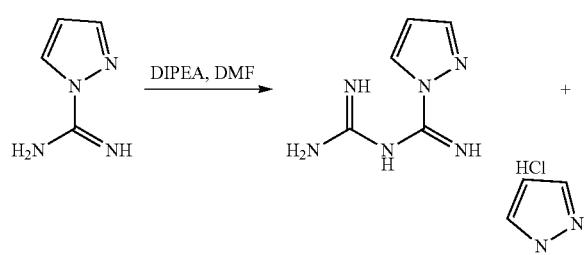

(4) Synthesis of r1,Me$_2$-r6,C$_8$-guanidino-Tei (24) and r1,Me$_2$-r6,C$_8$-diguanidino-Tei (25)

For guanylation, compound 22 (15 mg, 0.01 mmol) was dissolved in 0.1 mL DMF and reacted with 1-guanyl-pyrazole hydrochloride (1.5 mg, 0.01 mmol) or N-carbamimidoyl-1H-pyrazole-1-carboximidamide (1.6 mg, 0.01 mmol). The synthetic procedure was outlined in Scheme 3. The mixtures were stirred at room temperature for 24 hours (yield: about 50% for 24 and about 10% for 25) and purified by column chromatography. Corresponding products were identified by LC-MS. For compound 27, r1,Me$_2$-r4,C$_8$-amine-Tei (22) was replaced by deacyl teicoplanin following the same procedures described above.

(5) Synthesis of r4/r4, r6/r6 and r4/r6-Tei Analogs Coupling Compounds

For formation of the r4-diacylated-Tei dimer (29), r6-acylated-Tei dimer (30) and r4,diacylated-r6,acylated-Tei dimer (31), sebacoyl chloride was used to link two individual compounds through an r1-r1 linkage. Compound 14 and/or 28 (0.005 mmol), TEA (0.01 mmol), DMF (2 mL), and sebacoyl chloride (0.0025 mmol) were added at the same time. The reaction mixture was then stirred at room temperature overnight. All products were purified by HPLC.

(6) Synthesis of 8-guanidino-octanoic acid

8-Aminooctanoic acid (159 mg, 1 mmol) and 1-guanyl-pyrazole hydrochloride (146.5 mg, 1 mmol) were dissolved in 2 mL of 1 M Na$_2$CO$_3$ and stirred at room temperature as shown in Scheme 7. The white solid product was confirmed by mass spectrometry (LC-MS: m/z 202 [M+H]$^+$), which was washed with several small portions of MeOH/H$_2$O (1:1). The product was collected and dried for use.

Scheme 7 Synthesis of 8-quanidino-octanoic acid

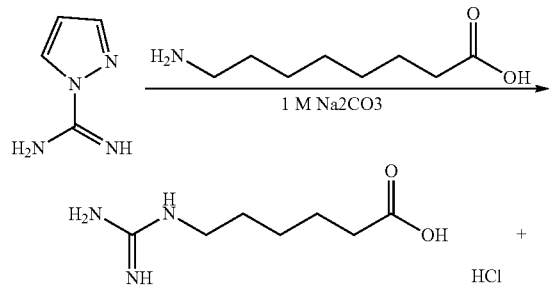

Enzymatic Synthesis of r6,N-acyl Glc Tei Analogs

(1) Biochemical Synthesis of UDP-Glm Using NahK-Glm U Chimeric Protein

A typical enzymatic reaction was performed in a 100 μL reaction solution containing 100 mM Tris pH 8.0, 5 mM glucosamine, 5 mM ATP, 5 mM UTP, 5 mM MgCl$_2$ and 0.2 mg NahK+GlmU at 37° C. overnight. Reactions were quenched by boiling the mixture for 10 minutes, followed by centrifugation at 15,000 rpm for 20 minutes. The supernatants were subjected to ion-exchange chromatography, where a linear gradient of 0.3% to 60% of 1 M ammonium formate against H$_2$O for 40 minutes was set.

(2) Double Methylation of N-Terminal Amino Group Using Dbv27

A typical enzymatic reaction contained 20 μg purified enzyme, substrates (compound 9 or 12) and S-adenosylmethionine (SAM) in a buffer solution of 50 mM HEPES at pH 8.0 with 10% DMSO. The reaction was incubated at 25° C. overnight. The mixture was quenched by addition of 10% 6N HCl in due course. Altering the molar ratio of SAM to Tei-pseudoaglycone 2:1 (pH 8), the N-terminal amino group can be doubly methylated to form r1,Me$_2$-r6,Glm-Tei-pseudoaglycone under the same condition.

(3) Glycosylation of Tei-pseudoaglycone Using Orf1 and Orf10*

The heptapeptide aglycone (4) was obtained through acid hydrolysis of teicoplanin (1) with 70% trifluoroacetic acid (TFA). Compound 4 was purified from the reactions by column chromatography. The enzymatic reactions for glycosyltransferase Orf1 or Orf10* were carried out in a 50 mM Tris buffer solution (pH 8.0) containing 0.5 mM UDP-GlcNAc, 0.5 mM compound 4, 5 mM MgCl$_2$, 1 mM DTT, 1 mgmL$^{-1}$ BSA and 10% DMSO. The reaction was triggered with addition of 10 μg of the enzyme and incubated at 37° C. overnight. The reaction was quenched by the heat treatment at 95° C. for 5 minutes in due course.

(4) r6,Glm Pseudoaglycone (12) Transformation Using Orf2*T (a Triple-Mutation Mutant S98A/V121A/F193Y)

For the deacetylation, the reaction mixture contained 0.5 mM r6,GlcNAc pseudoaglycone (9) in 10% DMSO in 50 mM HEPES (pH 8.0). The reaction was started with addition of 20 μg Orf2*T and incubated at 37° C. overnight. The reaction was quenched by addition of 10% 6N HCl in due course (the yield was about 100% as no observable substrate left after reaction).

(5) r6,N-Acyl-Glc Tei Analogs Transformation Using Orf11*S (a Single-Mutation Mutant W163A)

The reaction mixture contained 1 mM of substrates (a given acyl-NAC), 1.2 mM of coenzyme A and 1 mM of r6,Glm pseudoaglycone (12) dissolved in a buffer solution (50 mM HEPES, pH 8.0, 10% DMSO). The reaction mixture was started with addition of 50 μg Orf11*S and incubated at 25° C. overnight (the yield was about 100% as no observable substrate left after reaction). The reaction was quenched by addition of 10% 6N HCl in due course, which was centrifuged at 15,000 rpm for 5 minutes and filtered on an ultracentrifugal filter unit (5 kDa cut-off membrane). The filtrate was subjected to HPLC for analysis and collection with a gradient solvent system of increasing acentonitrile (with 0.1% FA) versus water (with 0.1% FA). The collected fractions were lyophilized and confirmed by LC-MS.

Electrospray Ionization Mass Spectrometry (ESI/MS)

Figure 1U:
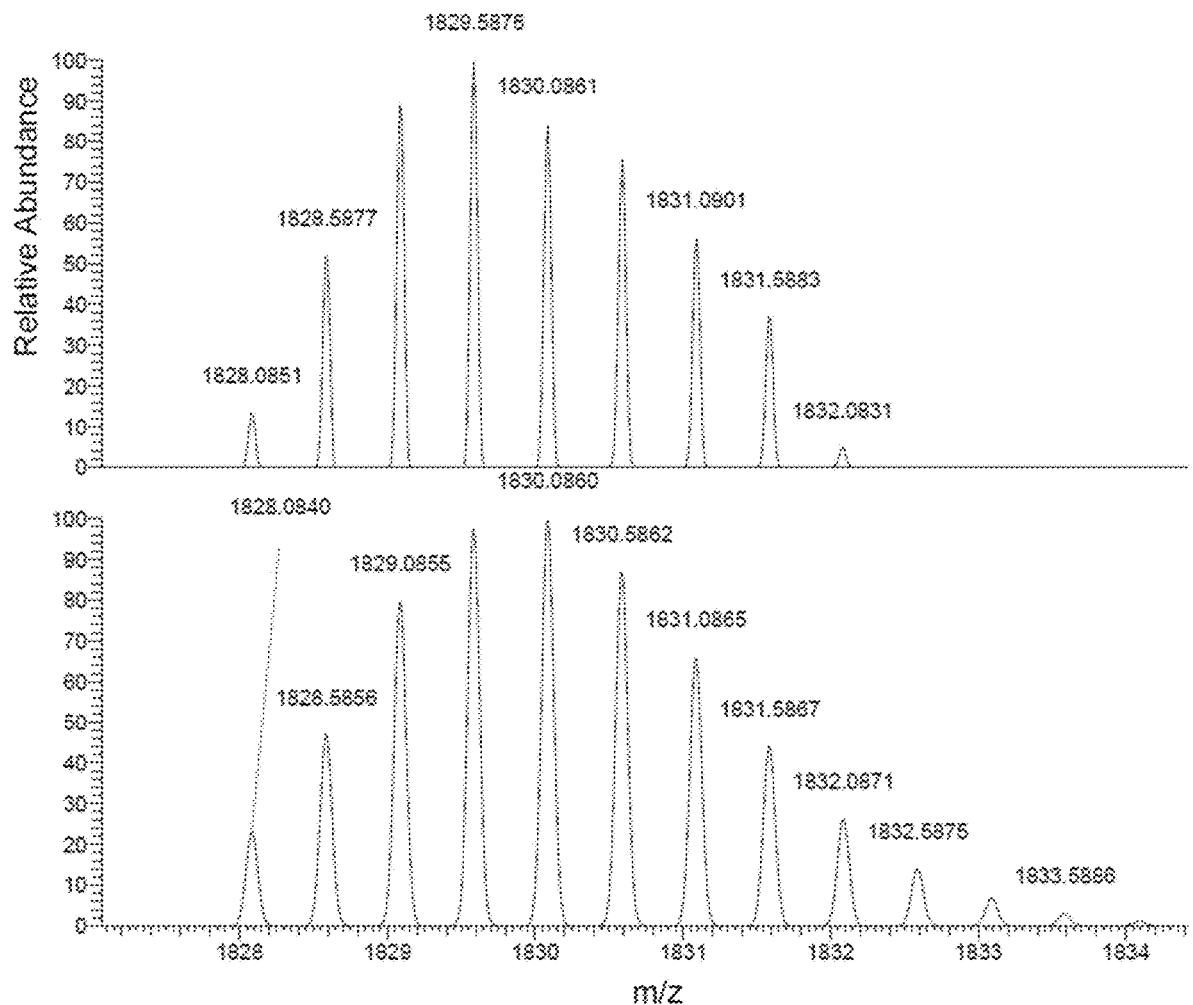

The ESI/MS spectra for compounds 9, 10, 12-27 and 29-31 were depicted in FIGS. 1A-1U. Compounds 9, 10, 12-27 were protonated as a singly charged molecular ion ([M+H]$^+$) in the spectra, which are in agreement with individual predicted monoisotopic mass (exact mass, M). Compounds 29-31 were protonated as a doubly charged molecular ion ([M+2H]$2^+$) in the spectra, where the top spectrum is experimental mass and the bottom spectrum is predicted/simulated mass. Multiple isotopic peaks account for two chlorine atoms attached on the aglycone (which carries two dominant isotopes 35Cl and 37Cl in a natural abundance ratio of 1:3).

Isothermal Titration Calorimetry (ITC) Analysis

A stock solution (50 mM) was prepared by dissolving r6,GlcNAc pseudoaglycone (9) in 50% DMSO. The 1 mM protein solutions of Orf2*, Orf2*T and Dbv27 were prepared in a 50 mM HEPES buffer solution at pH 8.0. The solution (50 mM HEPES, pH8.0 and 10% DMSO) that contained compound 9 (1 mM) or S-adenosylmethionine (SAM) (1 mM) in a 40 μL injection syringe was titrated into the Orf2*, Orf2*T or Dbv27 (0.1 mM) protein solution, which was placed in the sample cell of a 200 μL volume. Each titration consisted of 16 injections of a 2 μL4 s$^{-1}$ duration in an interval of 150 seconds. Data analysis was performed by software.

Kinetics of Orf11*S (Acyl Transfer to r6,Glm Pesudoaglycone (12) and r4,Glm Pseudoaglycone (6))

The kinetics of Orf11*S for the formation of r4/r6,Glm-Tei analogs was determined, where a reaction solution (50 mM HEPES at pH 8.0, 10% DMSO) contained compound 6 or 12 (acceptor, 0-500 μM) and decanoyl-CoA (donor, 1000 μM decanoyl-CoA). The reaction was started with addition of 5 μM Orf11*S and incubated at 25° C. The reaction mixture was quenched at 0, 1, 3, 8, 15, 30 and 60 minutes by addition of 10% 6 N HCl and subjected to HPLC analysis (with a flow rate of 1 mLmin$^{-1}$ and a linear gradient solvent system of increasing acentonitrile (0.1% FA) versus water (0.1% FA) over 40 minutes; UV was set at 280 nm). Data analysis and curve fitting were performed by software.

Determination of Minimal Inhibitory Concentration (MIC) for Vancomycin, Teicoplanin and Tei-Analogs Versus Selected Strains MICs were determined by the broth microdilution method. Specifically, 12 Colonies of the test strain were picked up from 18-24 hour agar cultures and freshly inoculated into broth mediums until reaching the turbidity of a 0.5 McFarland standard. The broth culture was adjusted with broth medium to approximately 1×10$^8$ CFUmL$^{-1}$. Each MIC panel contained a series of 2-fold dilutions for a given test compound that was freshly prepared in 50% DMSO and added in the cell suspensions (5×10$^5$ CFUmL$^{-1}$), giving final concentrations of 0.016-32 μgmL$^{-1}$. The plates were incubated in 37° C. for 18-24 hours and monitored for the wells of the positive control, where cells grew, and the wells of the negative control, where wells should not grow. The MIC value was determined for the concentration of a test compound, at which there was no visible growth in the well.

Minimal Bactericidal Concentration (MBC) Determination

The MBC test is an extension of the MIC examination. MBC was determined by performing subcultures on antibiotic-free agar from both the well where there was no visible growth at the MIC of a tested antibiotic and from the positive control well (with inoculum but without compounds). The plates were incubated at 37° C. for 18-24 hours. The MBC was taken as the lowest concentration of the test compound that results in more than 99.9% reduction of viable bacteria. If MBC was one or two dilutions above a given MIC value (MBC/MIC ratio was less than or equal to four), the antibiotic was considered bactericidal against the test organism.

Thin-Section Transmission Electron Microscopy (TEM)

An overnight cultured MRSA ATCC 700787, VRE ATCC 700221 or A. baumannii ATCC 19606 was individually sub-cultured into a fresh medium. Bacteria at the exponential phase were treated with a given test compound at a concentration of 4×MIC for 1-4 hour at 37° C. and followed by wash and resuspension in PBS. Bacteria cells for the TEM analysis were prepared as follows: Cells were fixed with 2.5% glutaraldehyde for 30 minutes. After the fixation, cells were washed twice with PBS and fixed with 1% osmium tetraoxide for another 30 minutes. All the buffer was removed with distilled water. The cells were then stained with 1% uranyl acetate and dehydrated with a graded ethanol solution. Cells were embedded in resin. Finally, each sample was cut into thin slices of approximately 90 nm with a glass knife and stained with uranyl acetate. The images of bacterial morphological were recorded.

Cell Viability Assays

The Alamar Blue (AB) assay, which includes a redox indicator that changes color or emits fluorescence in response to a metabolic activity, was used to assess in vitro mammalian cell cytotoxicity (human embryonic kidney cells (HEK293T)) upon an antibiotic treatment. 2×10$^5$ cellsmL$^{-1}$ were allowed to adhere on 96-well plates overnight at 37° C. in a humidified incubator (5% CO$_2$ atmosphere). Tested compounds were dissolved in 50% DMSO to make 1 mgmL$^{-1}$ of a stock solution. Cells were separately aliquoted with 5 μL of a test compound (final concentration: 100 μgmL$^{-1}$) and incubated. PBS and 50% DMSO, which was used to dissolve compounds, served as a control. Cell viability was triplicated and assessed at 2 and 24 hour time points for each test compound, on which the measurements followed the manufacturer protocol.

Hemolysis Assay

Human erythrocytes were centrifuged down from the fresh heparinised blood and resuspended in 5% PBS at pH 7.4. The erythrocyte suspension (150 μL) was added with 50 μL of a given test compound (1000 μM). Two controls were prepared, one without addition of the test compound as a negative control, and the other with addition of 1% TRITON X-100 as a positive control. After incubation (at 37° C. for 1 hour), 96-well plates were centrifuged at 3,500 rpm for 5 minutes, of which 100 μL of the supernatant of each well was transferred to a second 96-well plate to measure the absorbance at 540 nm (A$_{540}$). For the percentage of hemolysis, the formula [(A−A$_0$)/(A$_{total}$−A$_0$)]×100 was applied, where A is the absorbance of the compound-containing well, A$_0$ is the absorbance of the negative control (without compound), and A$_{total}$ is the absorbance of the TRITON X-100 containing well. Each assay was triplicated.

In Vivo Efficacy of r6,N-Acyl-Glc Tei Analogs

Female C57BL/6 mice (6 weeks of age; about 16-19 g, 3-5 mice per group) were intraperitoneally inoculated with 300 µL of MRSA ATCC 700787 suspension (about $10^7$ CFUmL$^{-1}$). For intranasal *A. baumannii* (ATCC 19606) inoculation, mice were anesthetized, and inoculated intranasally with about $10^7$-$10^8$ CFUmL$^{-1}$ *A. baumannii* in 50 µL of PBS. Treatments were started 1 hour after the bacterial challenge. The dose administration to mice was set as follows: teicoplanin (1) or r6,C8-Tei analog (14) 20 mgkg$^{-1}$ was intraperitoneally injected to MRSA-infected mice; amikacin (15 mgkg$^{-1}$), teicoplanin (1) (30 mgkg$^{-1}$), kanamycin (30 mgkg$^{-1}$) or r1,Me$_2$-r6,guanidino-C$_8$ analog (24) (30 mgkg$^{-1}$) was intraperitoneally injected to AB-infected mice. To assess bacteraemia, the test animals were sacrificed to collect 1 mL of peritoneal fluid (PF) for MRSA counting or the lungs were lavaged to collect 0.6 mL bronchoalveolar lavage (BAL) fluid for *A. baumannii* counting.

Membrane Permeabilization Assay

The inner membrane and outer membrane permeabilization was determined by propidium iodide (PI) and 1-N-Phenylnaphthylamine (NPN), respectively. MRSA (ATCC 700787) and *A. baumannii* (ATCC 19606) at mid-log phase were harvested, washed and resuspended in a solution containing 5 mM glucose and 5 mM HEPES at pH 7.2. For the inner membrane permeabilization, 150 µL cell suspension and 50 µL PI (10 µM) were added together and preincubated for 30 minutes or 60 minutes for MRSA or *A. baumannii*, respectively. For outer membrane permeabilization activity, 150 µL cell suspension and 50 µL NPN (10 µM) were added together and preincubated for 60 minutes. The change of fluorescence intensity was recorded for 8 minutes at 2 minute intervals with excitation and emission wavelength set at 535 nm and 617 nm, respectively for PI and with excitation and emission wavelength set at 350 nm of 420 nm, respectively, for NPN. When 5 µL of a given test compound was added in the solution, the fluorescence intensity was recorded for another 12 minutes.

Figure 2A:
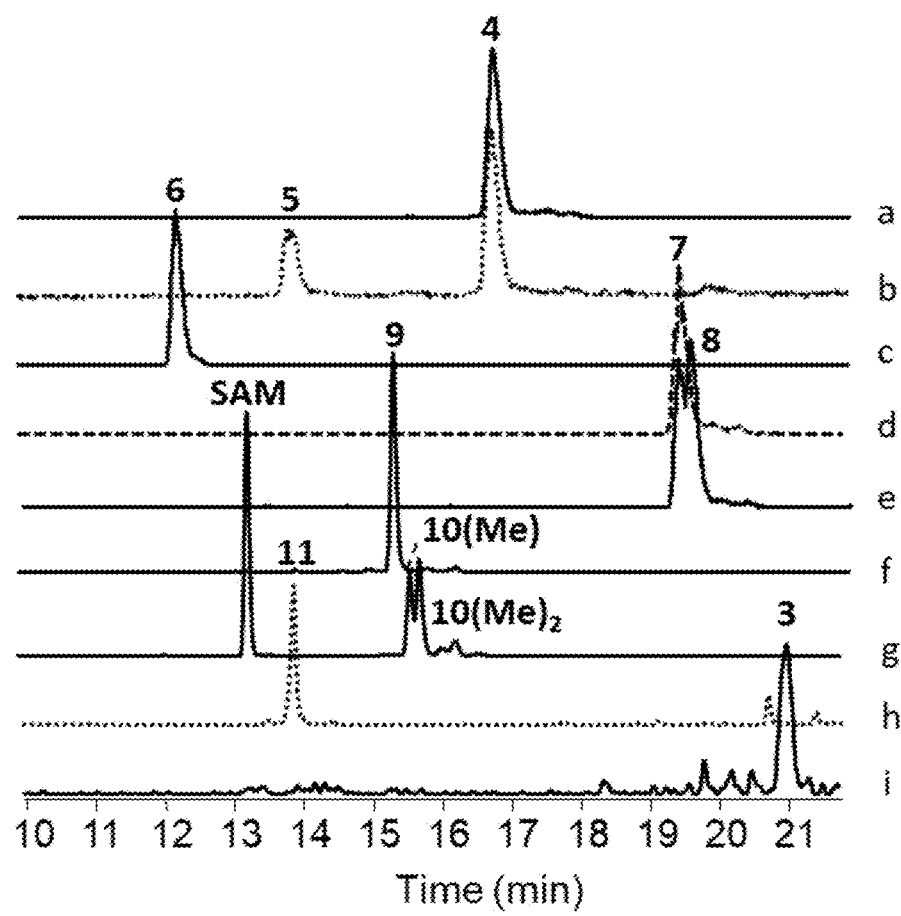
FIGS. 2A-2E are results of liquid chromatography (LC) traces and isothermal titration calorimetry (ITC) thermographs according to one embodiment of the present disclosure.

Example 1 Synthesis of the Present Compounds 1.1 Synthesis of r4,N-acyl Glc Tei Analogs Three genes orf10*, orf2* and orf11* in the tei biosynthetic gene cluster respectively code for a glycosyltransferase, a deacetylase and an acyltransferase in a row to decorate Tei aglycone with the N-acyl Glc pharmacophore at r4 (Scheme 1, lines a-d of FIG. 2A). These enzymes in conjunction with three other enzymes Orf1*, Dbv27 and NahK (see below) in their cognate or engineered states lend an opportunity to form new Tei analogs (line e of FIG. 2A), wherein more efficacious analogs ought to exist.

1.2 Synthesis of r6,N-acyl Glc Tei Analogs

To achieve the goal set, we first took advantage of Orf1 because it was straightforward given that glucosamine (Glm) in lieu of GlcNAc can be added on Tei aglycone. While UDP-Glm can be biochemically synthesized in quantity using NahK (to form Glm-1-phosphate) in conjunction with GlmU (to form UDP-Glm), this attempt failed because the substrate of Orf1 was limited strictly to UDP-GlcNAc (line f of FIG. 2A). A structure-based protein engineering for Orf1 was pursued. Such an attempt was un-succeeded, as neither native nor ligand-bound Orf1 was crystalized under myriad screening conditions. Orf1 was subsequently subjected to homology modeling using the solved crystal structures GtfA, GtfB or chimerical GtfAH1 as the model templates. Dozens of site-directed mutants were made on the basis of the model and a handful of chimeras were also made through swapping the sugar recognition domain of Orf1 with that of Orf10*/GtfA/B. Unfortunately, these attempts remained un-succeeded because of short of the anticipated activity (wherein many mutants/chimeras turned out to be insoluble). We then exploited the reversible glycosyltransferase-catalyzed reactions to transfer epi-vancosamine from chloroeremomycin to Tei aglycone. This approach still did not work here. We finally took a stepwise approach outlined in Scheme 2: Orf1 adds GlcNAc to r6 of Tei aglycone. The N-acetyl group at r6 was then removed using an engineered Orf2* prior to lipidation of a long aliphatic chain by an engineered Orf11*to form the wanted representative 3.

Figure 2B:
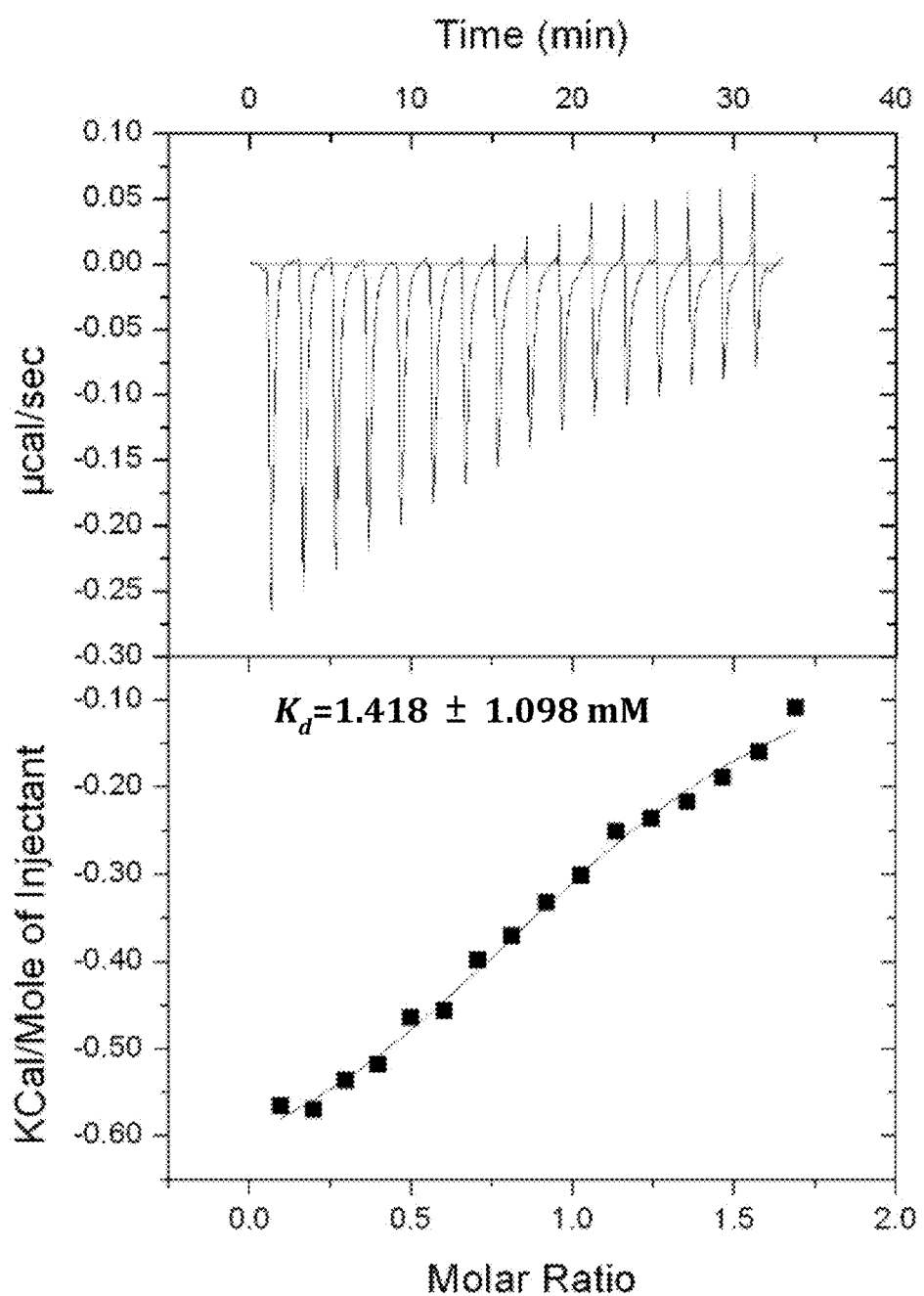
Figure 2C:
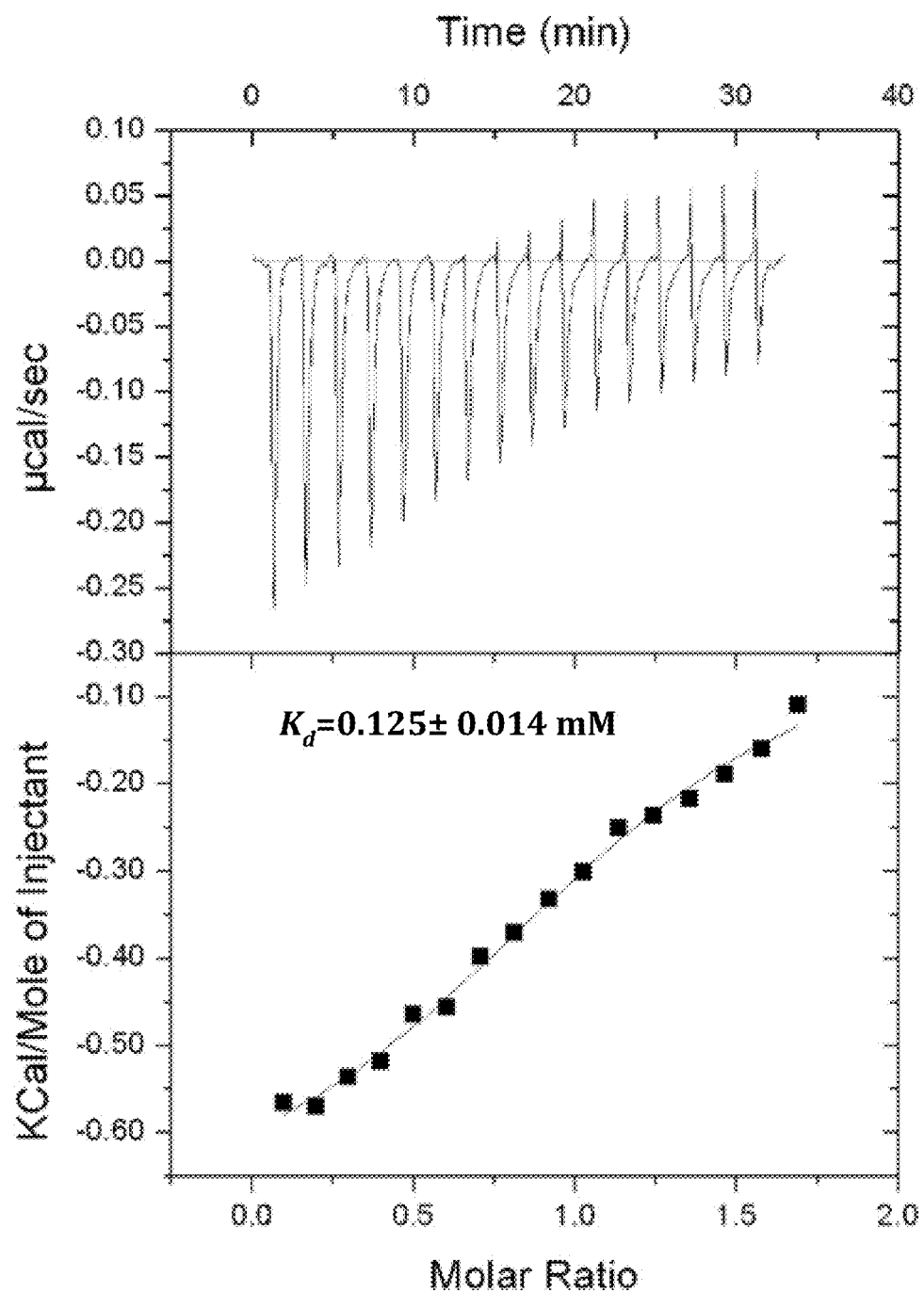

Orf2* is a deacetylase that hydrolyzes the N-acetyl group off GlcNAc specifically at r4 of Tei-pseudoaglycone. On the basis of the solved crystal Orf2* complex, a limited scale of directed evolution (for residues in the substrate binding site) was practiced and thereby generated a triple mutant (Orf2*T: S98A/V121A/F193Y). Orf2*T was examined capable of unleashing the amine group at r6 GlcNAc of Tei-pseudoaglycone (line h of FIG. 2A). ITC analysis revealed that the binding affinity of r6,GlcNAc-Tei-pseudoaglycone versus Orf2*T ($K_d$=0.125±0.014 mM) is higher than that of r6,GlcNAc-Tei-pseudoaglycone versus Orf2* ($K_d$=1.418±1.098 mM) (FIGS. 2B and 2C). The overall catalytic specificity Orf2*T versus r6,GlcNAc-Tei-pseudoaglycone was assessed to be $k_{cat}K_m^{-1}$=45.28 s$^{-1}$ mM$^{-1}$ well in a typical enzymatic scop (data not shown), albeit it was about 8-fold less specific than Orf2* versus the original r4 counterpart ($k_{cat}K_m^{-1}$=377.3 s$^{-1}$ mM$^{-1}$). The crystal structure of Orf2*T was solved (data not shown), while the r6,Glm-Tei-pseudoaglycone-complexed structure was not achieved due to undefined electron density under a higher molecular oscillation. The capping loop region (residues 110-120), which acts as a lid in governing substrate entry, cannot be built likely due to the r6,Tei-pseudoaglycone-induced conformational disorder. The low root-mean-square deviation (RMSD) of 0.44 Å for 207 Cα atoms upon structural superposition for both Orf2* and Orf2*T suggested that there were no significant conformational changes except the side chains of the residues that were subjected to site-directed mutagenesis in Orf2*T. In brief, S98 may assist r4,GlcNAc of Tei-pseudoaglycone in alignment toward the reaction center through interacting with C6-OH; V121 may help anchor the aglycone scaffold through hydrophobic interactions with the backbone amide bonds of r1 and r2; the phenyl ring of F193 is also hydrophobically interacting with the m-chlorine substituted phenyl ring of r4. Given the triple mutant S98A/V121A/F193Y, r6,Tei-pseudoaglycone is allowed to rotate about 90° in a trajectory suitable for the deacetylation reaction to proceed by one order of magnitude less efficient than that of r4,Tei-pseudoaglycone versus WT ($k_{cat}/K_m^{-1}$=377.3 s$^{-1}$ mM$^{-1}$) (data not shown). Provided Tei pseudoaglycone that contains two GlcNAc moieties at both r4 and r6, the one at r4 is still dominant, likely because of a better overall fitness of the original conformation to the binding site.

Figure 2D:
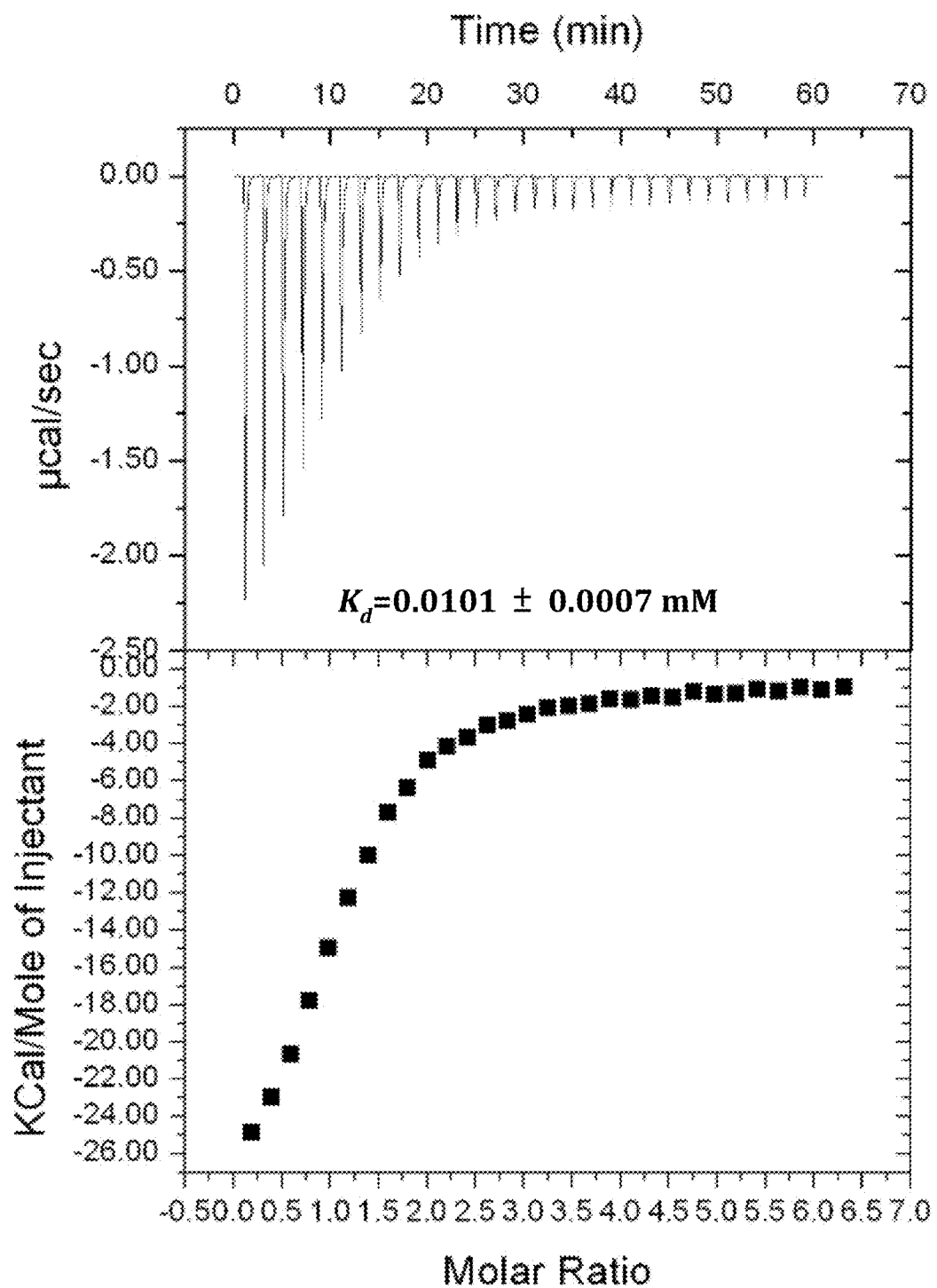
Figure 2E:
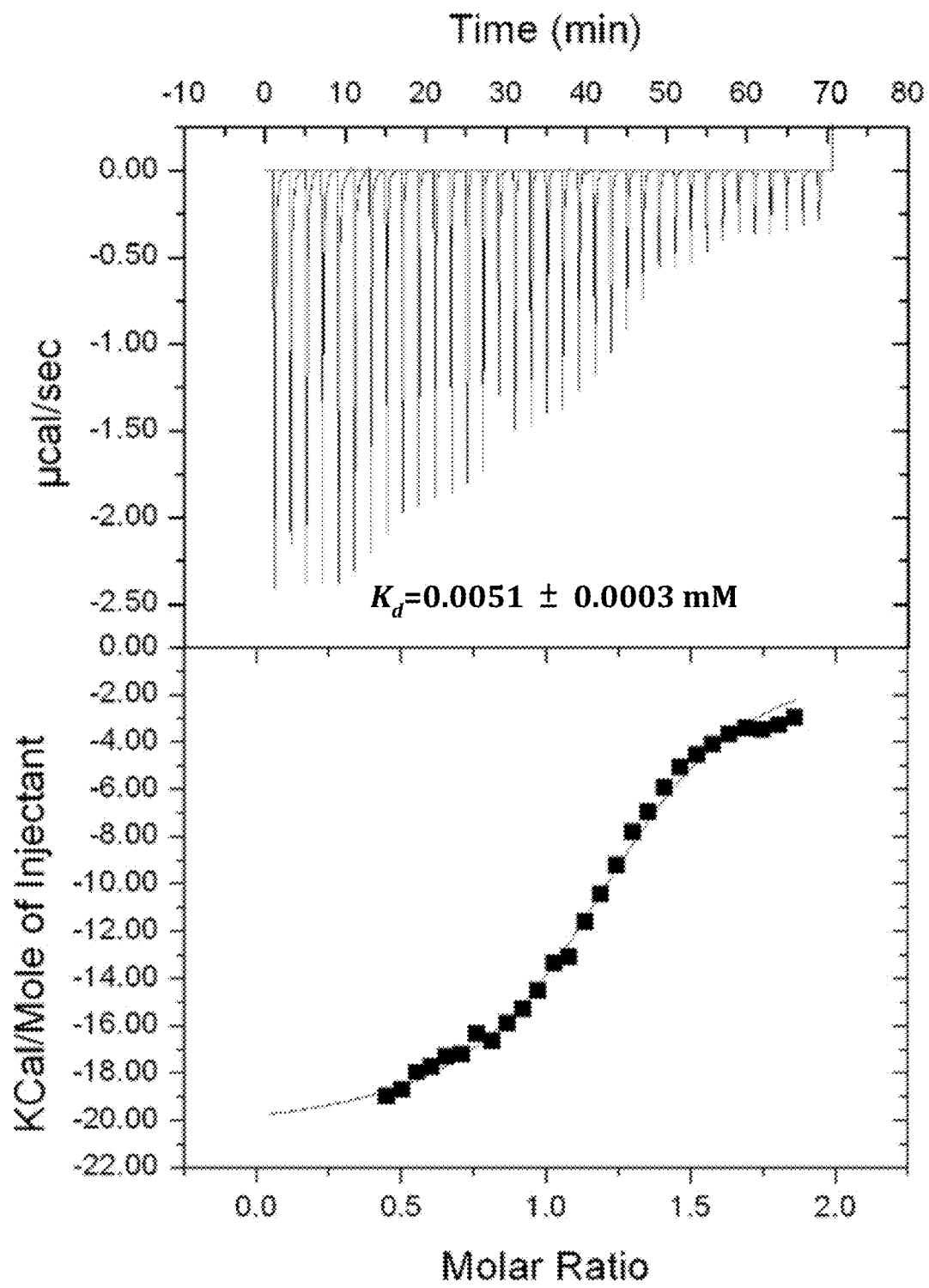

Having deacetylated, the primary amine group of r6,Tei-pseudoaglycone is readily subjected to lipidation by handy chemical reactions, such as acylation or alkylamination. One, however, should be aware that there is another primary amine group at the N-terminus (r1). Protection chemistry therefore needs to be exercised in order for the regioselective lipidation at r6 of Tei-pseudoaglycone. Dbv27, predicted to be an S-adenosylmethionine (SAM)-dependent methyltransferase at the N-terminus in the maturation of A40926 (data not shown), may lend an opportunity to selectively protect the amino group at r1. While A40926 contains no sugar moiety at r6, r6,GlcNAc-/r6,Glm-Tei-pseudoaglycone can still be taken by Dbv27 allowing methylation at the N-terminal amino group (line g of FIG. 2A). ITC analysis revealed that Dbv27 binds strongly with SAM ($K_d$=10 µM) or r6,Glm-Tei-pseudoaglycone ($K_d$=5 µM) (FIGS. 2D and 2E). Interestingly, increasing the molar ratio of SAM to Tei-pseudoaglycone (2:1, pH 8) the N-terminal amino group can be doubly methylated to form r1,Me$_2$-r6, Glm-Tei-pseudoaglycone in a fully protected manner (line g of FIG. 2A).

Despite that r1,Me$_2$-r6,N-acyl-Glc-Tei analogs can now be implemented by chemical acylation or alkylamination, an integrated biochemical approach, nonetheless, was attempted on account of future large-scale production through synthetic biology. Orf11* that catalyzes acylation of r4,Glm-Tei-pseudoaglycone was opted and subjected to protein engineering to assume this task. The advantage of using Orf11* was that the substrate r6,Glm-Tei-pseudoaglycone was a close regioisomer to its cognate substrate r4,Glm-Tei-pseudoaglycone, and the ternary structures of Orf11* in complex with the r4,Glm-Tei-pseudoaglycone acceptor and the acyl-CoA donor were available. The Tei-pseudoaglycone binding site was located at the colossal junction between the N- and C-terminal domains, where W163 in the N-terminal domain served as the anchoring base with its bulky indole moiety fitting well into the concave of the aglycone core to align r4,Glm toward the reaction center (data not shown). Given the anchoring role, W163 was mutated to W163A, whereby disruption of the binding fidelity may instead allow r6,Glm to head to the reaction center for the acyl-transfer reaction to take place at r6. As expected, this single mutant W163A was capable of transferring an acyl side chain from a corresponding Co-A derivative to r6,Glm forming r1,Me$_2$-r6,N-acyl-Glc-Tei-pseudoaglycone in a reasonable enzymatic scope ($k_{cat}$=3.85±0.23 min$^{-1}$, $K_m$=0.3±0.03 mM, $k_{cat}K_m^{-1}$=12.92 min$^{-1}$ mM$^{-1}$) (line i of FIG. 2A). The binding affinity of r6,Glm-Tei-pseudoaglycone ($K_m$=0.3 mM) was about 5-fold less than that of r4,Glm-Tei-pseudoaglycone ($K_m$=0.07 mM) in consistence with catalytic specificity ($k_{cat}K_m^{-1}$=12.92 and 87.49 min$^{-1}$ mM$^{-1}$ for r6,Glm-Tei-pseudoaglycone and r4,Glm-Tei-pseudoaglycone, respectively). In analogy to Orf2*T, r4,Glm still outruns r6,Glm, as r4,Glm-Tei-pseudoaglycone as a whole was more fit to the substrate binding-site. The crystal structure of W163A was solved (data not shown), while the ternary complex soaked with r1,Me$_2$-r6,Glm-Tei-pseudoaglycone remained unachievable because of an unclear electron density map for the aglycone core due to a larger extent of molecular oscillation (data not shown). Structural superposition of Orf11* over W163A shows a low root-mean-square deviation (RMSD) of 0.286 Å for 295 Cα atoms, suggesting there was no significant conformational changes between Orf11* and W163A except the designated mutation (data not shown). The removal of the anchoring indole is, however, enough to enable Tei-pseudoaglycone rotating 90° for the primary amino at r6,Glm in alignment with the reaction center to proceed the acyltransfer reaction (data not shown).

Though there is still room for further improvement for both Orf2*T and W163A (now termed as Orf11*S) in terms of reaction efficiency/overall yield, the current lineup, nevertheless, has enabled us to synthesize a cohort of r6,N-acyl-Glc Tei analogs in quantity (at the level of >20 mg for each). Two representative compounds 12 and 14 were further subjected to 1D and 2D NMR analysis for structural validation (data not shown).

Example 2 Antimicrobial Activity of r6,N-acyl-Glc Tei Analogs

Having synthesized r6,N-acyl-Glc-Tei analogs, the minima inhibition concentrations (MICs) for compounds 13-27 alongside r4,di-acyl-Glm-Tei (28) (effective in killing VREs) were assessed against a collection of drug-sensitive Enterococci/*Staphylococcus aureus* (VSE/MSSA) and drug-resistant VRE/MRSA/VISA/VRSA pathogens in comparison with teicoplanin and vancomycin.

As shown in Table 2, compound 1 was marginally more potent than compound 2 against the selected MRSA strains, in which ATCC 700698 and ATCC 700789/ATCC 700787 were vancomycin intermediate (VISA) and resistant (VRSA) strains, respectively. While r4,N-acyl-Glm-Tei analogs (particularly compound 28) were relatively more potent than r6,N-acyl-Glc counterparts (compounds 13-19) versus VREs, the r6,N-acyl-Glc Tei analogs, strikingly, outperforms 1, 2, or 28 by 1-3 orders of magnitude (as low as 0.01 µgmL$^{-1}$) versus VISA/VRSA (ATCC 700698/ATCC 700789 and ATCC 700787). It is clear that each of r4,N-acyl-Glc (compound 28) and r6,N-acyl-Glc analogs (compounds 13-19) exhibited a distinctive pharmaceutic effect, respectively, on VRE or MRSA. In brief, the r6,N-acyl-Glc-Tei analogs with or without methyl groups at r1 made no apparent difference on MIC, suggesting the N-terminal methyl groups (compounds 10, 20) had little or no role on the killing effect. Similarly, an extra mannose at r7 (compound 26) made not much improvement. These modifications, however, may be crucial in vivo in view of pharmacokinetics/pharmacodynamics (e.g., methylation at r1 may resist hydrolysis from endogenous proteases; an extra sugar may enhance drug solubility). In general, a better potency can be expected given an analog with a longer lipid chain. A phenyl ring (compounds 15, 16, 18), a substituent on the phenyl ring (compound 18), a hydroxyl group (compounds 19, 21), or an amino group (compound 22) at the terminus of the lipid chain exhibited no better activity than the linear fatty acid one, concluding that lipidation on r6,Glm is the most critical factor in reference to the pathogen killing effect on both drug-sensitive and -resistant *S. aureus*.

TABLE 2

The minima inhibition concentrations (MICs, µgmL$^{-1}$) for compounds 13-27 and r4,di-acyl-Glm-Tei 28 against specified pathogens

| Compound | SA ATCC 29213 | MRSA ATCC 43300 | MRSA ATCC BAA-44 | MRSA ATCC BAA-38 | MRSA ATCC BAA-39 | MRSA ATCC 700789 VRSA[a] |
|---|---|---|---|---|---|---|
| 1 | 0.25 | 0.25 | 0.5 | 0.25 | 0.5 | 4 |
| 2 | 1 | 1 | 2 | 1 | 1 | 16 |
| 9 | 0.25 | 0.25 | 0.125 | 0.25 | 0.125 | 2 |
| 10 | 0.25 | 0.25 | 0.125 | 0.25 | 0.125 | 2 |
| 13 | 0.063 | 0.125 | 0.031 | 0.063 | 0.063 | 1 |

TABLE 2-continued

The minima inhibition concentrations (MICs, μgmL$^{-1}$) for compounds 13-27
and r4,di-acyl-Glm-Tei 28 against specified pathogens

| | | | | | | |
|---|---|---|---|---|---|---|
| 14 | 0.016 | 0.063 | 0.016 | 0.016 | 0.016 | 0.5 |
| 15 | 0.031 | 0.031 | 0.016 | 0.016 | 0.016 | 0.5 |
| 16 | 0.125 | 0.063 | 0.016 | 0.031 | 0.063 | 0.5 |
| 18 | 0.063 | 0.031 | 0.016 | 0.016 | 0.063 | 0.5 |
| 19 | 0.016 | 0.063 | 0.016 | 0.031 | 0.016 | 0.25 |
| 20 | 0.016 | 0.063 | 0.016 | 0.016 | 0.016 | 0.5 |
| 21 | 0.125 | ND | ND | ND | ND | ND |
| 22 | 0.031 | ND | ND | ND | ND | ND |
| 23 | 0.031 | ND | ND | ND | ND | ND |
| 24 | 0.5 | ND | ND | ND | ND | ND |
| 26 | 0.016 | 0.125 | 0.016 | 0.125 | 0.016 | 0.5 |
| 28 | 0.25 | 0.25 | 0.25 | 0.25 | 0.25 | 0.5 |
| 29 | >16 | >16 | >16 | >16 | >16 | >16 |
| 30 | 0.25 | 0.5 | 0.125 | 0.5 | 0.25 | 4 |
| 31 | 4 | 4 | 2 | 4 | 4 | 4 |
| 14 + 28 | 0.016 | 0.16 | 0.016 | 0.016 | 0.016 | 0.0625 |

| Compound | MRSA ATCC 700698 hVISA[b] | MRSA ATCC 700787 VRSA[c] | EF ATCC 29302 | VRE ATCC 700221 (vanA) | VRE ATCC 700802 (vanB) | VRE ATCC 700425 (vanC) |
|---|---|---|---|---|---|---|
| 1 | 4 | 8 | 0.125 | >128 | 0.5 | 1 |
| 2 | 4 | 16 | 2 | >128 | 64 | 16 |
| 9 | 1 | 0.5 | 2 | >128 | 4 | 4 |
| 10 | 1 | 0.5 | 2 | >128 | 4 | 4 |
| 13 | 0.063 | 0.063 | 0.5 | >16 | 4 | 4 |
| 14 | 0.016 | 0.016 | 0.25 | >16 | 0.5 | 1 |
| 15 | 0.016 | 0.031 | 0.25 | >16 | 0.5 | 1 |
| 16 | 0.016 | 0.125 | 0.25 | >16 | 0.25 | 1 |
| 18 | 0.016 | 0.125 | 0.25 | >16 | 0.25 | 1 |
| 19 | 0.016 | 0.016 | 0.25 | >16 | 0.5 | 1 |
| 20 | 0.016 | 0.016 | 0.25 | >16 | 0.5 | 1 |
| 21 | 0.063 | 0.125 | 1 | >16 | 8 | 8 |
| 22 | 0.125 | 0.063 | 1 | >16 | 1 | 2 |
| 23 | 0.031 | 0.031 | 0.25 | >16 | 1 | 2 |
| 24 | 0.031 | 0.016 | 0.5 | >16 | 4 | 8 |
| 26 | 0.031 | 0.5 | 0.5 | >16 | 1 | 1 |
| 28 | 0.5 | 1 | 0.5 | 1 | 0.5 | 0.5 |
| 29 | 16 | >16 | >16 | >16 | >16 | >16 |
| 30 | 0.25 | 4 | 4 | >16 | 4 | 4 |
| 31 | 4 | >16 | 8 | >16 | 8 | 4 |
| 14 + 28 | 0.016 | 0.0625 | 0.0625 | 1 | 0.125 | 0.125 |

SA: *S. aureus*;
EF: *E. faecalis*
ND: not detected
VRSA[a]: ATCC 700789 was defined as a VISA strain but it exhibited high resistance to vancomycin in this study.
hVISA[b]: The strain has apparent vancomycin MICs in the susceptible range; only clinical failure with vancomycin despite susceptible-range MICs suggests the possibility of an hVISA infection.
VRSA[c]: vancomycin MIC ≥ 16 μgmL$^{-1}$ according to the document *2015 CLSIM100-S25*.

Example 3 Coupling r4 and r6,N-acyl-Glm Tei Analogs

Having learned that Tei analogs with lipidation at r4 or r6 embody each analogs a selective bactericidal effect respectively on VRE or MRSA/VISA/VRSA, we hence wondered whether such antimicrobial selectivity could be expanded by integrating these two features as a whole.

To test this idea, a bifunctional short chemical linker was used to latch r4,- and r6,N-acyl-Glm Tei-pseudoglycone together through a r1-r1 linkage. Three combinations include two r4, N-acyl-Glm Tei-pseudoglycone 29, two r6,N-acyl-Glm Tei-pseudoglycone 30, and one r4 and one r6 N-acyl-Glm Tei-pseudoglycone 31, which were then subjected to antimicrobial assessment (Table 2). On the basis of MIC values, the antimicrobial activity, however, was not as broad/sensitive as anticipated. The overall performance was no better than each standalone versus selected bacteria. The lack of an additive effect may be attributed to two bulky components, which limited their spatial freedom while exerting their individual antimicrobial effects. In contrast, both separate r4 and r6 analogs (compounds 14 and 28) added together did exhibit a superlative synergistic effect (low-dose inhibition, where the quantity of each analog is halved) on both drug-resistant *enterococcus* and *staphylococcus* (extended antimicrobial spectrum) particularly effective against VRSA (both ATCC 700787 and ATCC 700789) and vanA-type VRE (ATCC 700221) (Table 2).

Example 4 Antimicrobial Activity to Gram-(−) Bacteria

Given a cationic trimethyl moiety attached to the terminus of a lipid side chain at the r7 carboxyl group of A47934/Van (dalbavancin/the Van analogs), the specific Gram-(+) antimicrobial spectrum expanded to some selected Gram-(−) strains, such as *E. coli*. The effectiveness may be attributable to both disruption of cell membrane integrity and/or enhancement of cell membrane permeability in addition to mask the lipid II substrates during the cell wall biosynthesis.

We applied this seminal concept to r6,N-octyl-Glc Tei (compound 14) by adding a hydroxyl (compound 21), amine (compound 22), trimethylamine (compound 23), guanidine (compound 24), or di-guanidine (compound 25) functional group at the terminus of the lipid side chain at r6,Glm and assessed their antimicrobial activity against the notorious nosocomial strain *A. baumannii* (AB).

First, each terminal substituted octanoic acid was chemically converted to a corresponding N-acetylcysteamine thioester, which then underwent transesterification with CoA to form a given CoA derivative. Compounds 21, 22 and 23 were enzymatically synthesized using Orf11*S in the presence of a corresponding CoA derivative. For compounds 24 and 25, compound 22 was subjected to guanidination using 1-guanyl-pyrazole hydrochloride.

These modified analogs, in general, were effective against MRSA/VRE with antimicrobial activity comparable to compound 14 (Table 3). Specifically, compound 21 exhibited a marginal antimicrobial activity (152.84 $\mu gmL^{-1}$) on AB, while compound 23 slightly improved its MIC value by 2-fold reduction (78.52 $\mu gmL^{-1}$). The MIC can be further improved by another 2-fold reduction (39.24 $\mu gmL^{-1}$) with introduction of a terminal mono- (compound 24) or di-guanidino (compound 25) group (the latter is slightly better than the former). The terminal guanidino group at r4 (compound 27) was relatively less potent than that at r6, suggesting that the regio-location is somewhat related to the inhibition activity. On the basis of the MIC values, compound 24/25 was comparable to kanamycin (an aminoglycoside antibiotic). Compound 14/24 was further examined for its intrinsic bactericidal activity (MBC), where the MBC/MIC ratios were 4 and 1 for MRSA and AB, respectively (Table 4). The modes of action apparently are multifaceted, including increased binding affinity with phospholipid components of cell membrane, facilitation of cell-membrane permeation to interact lipid II precursors, as well as disruption of cell membrane integrity.

TABLE 3

The minimal inhibition concentrations (MICs) for selected compounds against *A. baumannii* ATCC 19606
*A. baumannii* ATCC 19606 (MICs, $\mu M/\mu gmL^{-1}$)

| | |
|---|---|
| 1 | 100/187.97 |
| 2 | 200/297.15 |
| 10 | >200/>285.67 |
| 14 | 50/74.22 |
| 21 | 100/152.84 |
| 22 | 25/38.19 |
| 23 | 50/78.52 |
| 24 | 25/39.24 |
| 25 | 25/40.29 |
| 27 | 50/96.73 |
| 28 | 50/100.18 |
| kanamycin sulfate | 25/14.56 |
| streptothricin F | 12.5/6.28 |
| colistin sulfate | 1.56/1.98 |

TABLE 4

The minimal inhibition concentrations (MICs, $\mu gmL^{-1}$) and the minimal bactericidal concentrations (MBCs, $\mu gmL^{-1}$) for 14 and 24 versus MRSA (ATCC 700787) and AB (ATCC 19606)

| | MRSA ATCC 700787 | | | AB ATCC 19606 | | |
|---|---|---|---|---|---|---|
| Compounds | MIC | MBC | MBC/MIC | MIC | MBC | MBC/MIC |
| 14 | 0.016 | 0.063 | 4 | 74.22 | 74.22 | 1 |
| 24 | 0.016 | 0.031 | 2 | 39.24 | 39.24 | 1 |

Example 5 Cell Wall Morphology by TEM

To assess what damages the r4, or r6,N-acyl-Glm Tei analogs imposed on MRSA, VRE or AB, the testing bacteria treated with a given analog were subjected to thin-section transmission electron microscopy (TEM) analysis (FIG. 3). The morphologies of VRE/MRSA and AB respectively displayed typical cocci and coccobacillus structures in the absence of compounds (untreated control), where stratificated structures of an intact cell envelop (cell wall and cell membrane) can be distinguished on TEM images. In contrast, the well-defined structures of VRE or MRSA treated with compound 1, 2, 14, or 28 morphed into rather distinct phenotypes, whereon shape deformations and abnormalities showed extensive alterations, particularly, when cells underwent division.

Figure 3A:
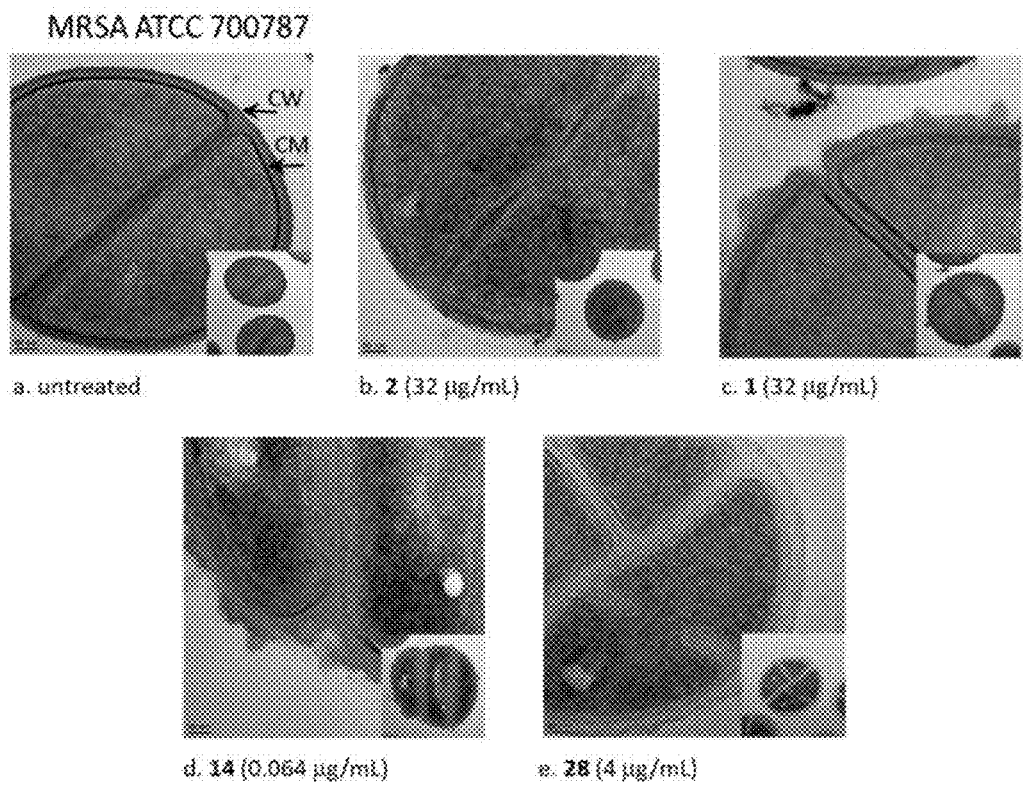
FIGS. 3A-3C are photographs depicting morphological changes of bacteria upon treatment with antibiotics according to one embodiment of the present disclosure.

Upon treatment with compound 2 (32 $\mu gmL^{-1}$), 1 (32 $\mu gmL^{-1}$), 28 (4 $\mu gmL^{-1}$) or 14 (0.064 $\mu gmL^{-1}$), the dense and well-defined cell wall structure of MRSA (ATCC 700787) underwent systemic swelling to various extents manifested respectively as floppy, loose, disintegrated, or cell wall damage toward full cell lysis in a progressive manner (FIG. 3A). The cell wall/membrane apparently is the targets, while the extent of damage depends on what compound imposes on the strain. Compound 14 displayed a lowest effective dosage. Cell wall thickening has been a common phenotype in clinical MRSA isolates, which may well be a phenotypic determinant for VRSA. The systemic cell-wall damage may account for the cell-wall biosynthesis crippled all over the cell surface in cell-wall thickening strains, thus leading cells to lysis as a result of the osmotic pressure of cytoplasm. The superlative antimicrobial activity of 14 was attributed to the r6,N-acyl-Glm pharmacophore effecting on lipid II or nascent peptidoglycan precursors with a higher binding affinity and/or a better inhibition trajectory.

Figure 3B:
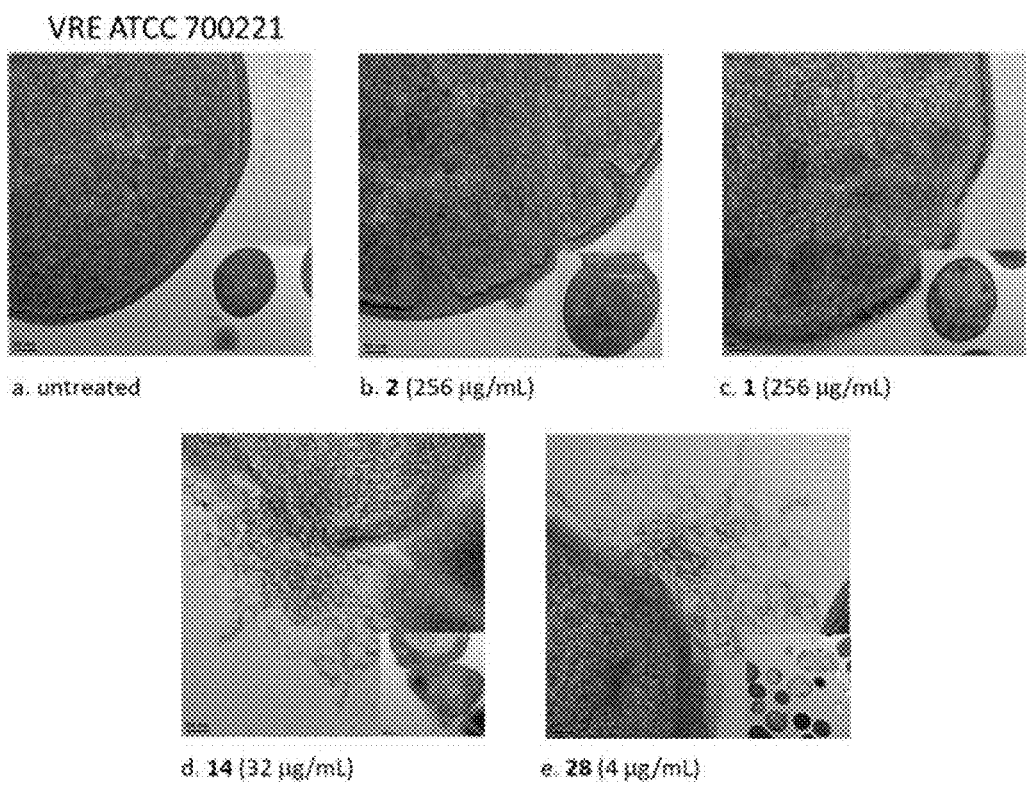

Upon treatment with the same analogs to VRE (ATCC700221, vanA type), a distinct phenotype was shown in FIG. 3B. The cell wall was almost intact but interspersed with holes, where cell fluids outflew leading cells to death. In general, VRE was immune to compound 1 or 2 (>256 $\mu gmL^{-1}$), median sensitive to compound 14 (32 $\mu gmL^{-1}$), but highly sensitive to compound 28 (4 $\mu gmL^{-1}$). The effectiveness of compound 28 may well be ascribed to new mode of action as manifested by the phenomenal bursting effect, where local cell membrane integrity and cell wall permeability are severely damaged as a causation of the r4,N-di-acyl-Glc pharmacophore wreaking on VRE at some specific foci on cell surface.

Figure 3C:
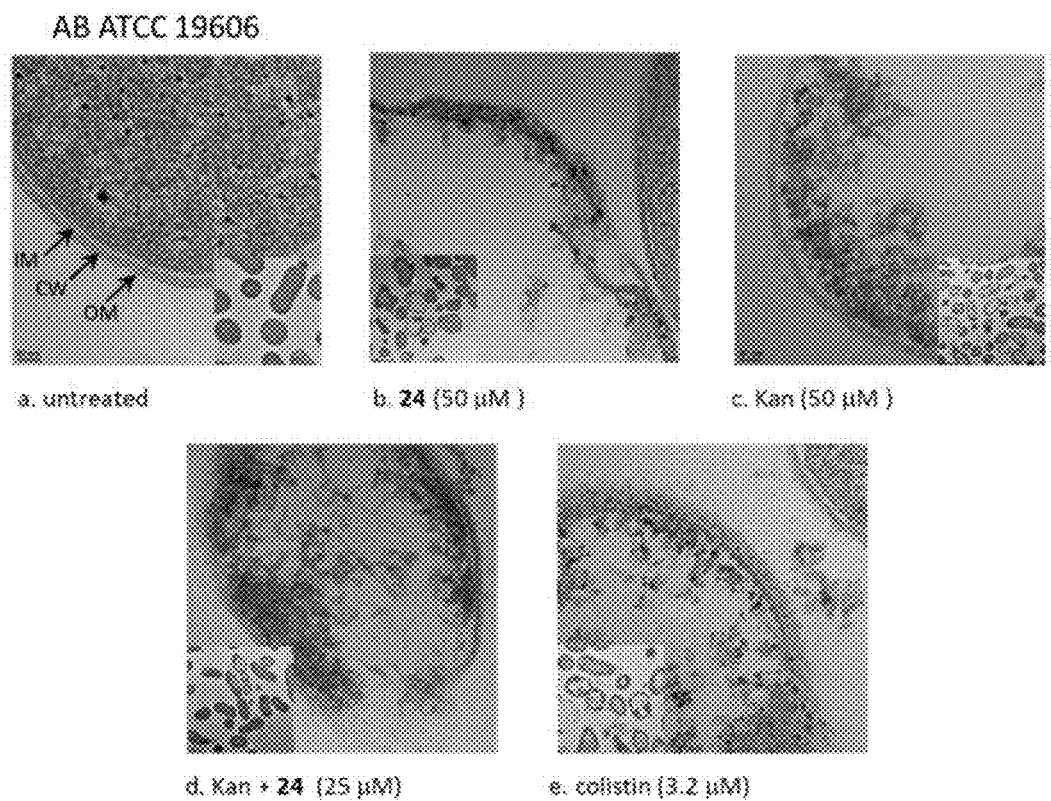

AB (ATCC 19606), a Gram-(−) bacterium, features a distinctive outer membrane visible on TEM images. This species was insensitive to glycopeptide antibiotics (compound 1 and 2, >189.97 $\mu gmL^{-1}$), medium sensitive to kanamycin (14.56 $\mu gmL^{-1}$), but highly sensitive to colistin (1.98 $\mu gmL^{-1}$) (FIG. 3C). Interestingly, AB is medium sensitivity to compound 24 or 25 in contrast to compound 1 and 2 (re-sensitization by >8 folds). As shown in the TEM images, the intactness of cell membrane/cell wall was severely damaged upon treatment with compound 24 (50 $\mu M$) or colistin (3.2 $\mu M$), resulting in outflow of cell fluids and thus leading cells to death. In contrast, AB treated with kanamycin remained enclosed by the roughly intact cell membrane/wall structures, while the area of cytoplasm was severely damaged. A phenomenal synergistic effect with the combination of a half dose of compound 24 (25 $\mu M$) and kanamycin (25 $\mu M$) was observed, where massive transudates gush out of the damaged cell membrane/wall of AB.

As a result, the effectiveness of compound 24 or 25 that outdoes the primary or quaternary amine counterparts may be ascribed to the conjugated positive charge on the guanidino group with a higher affinity to the membrane phospholipid. The lipid effector may simultaneously exploit its hydrophobicity to perturb cell membrane, wherefore Tei pesudoaglycone gains access to lipid II precursors and thus inhibits the cell-wall biosynthesis.

Example 6 Safety/Cytotoxicity and Cell-Membrane Permeability of r6,N-Acyl-Glc Tei Analogs The Alamar Blue (AB) assay, which contains a redox indicator in response to metabolic activity, was used to evaluate mammalian cell cytotoxicity in vitro.

Figure 4A:
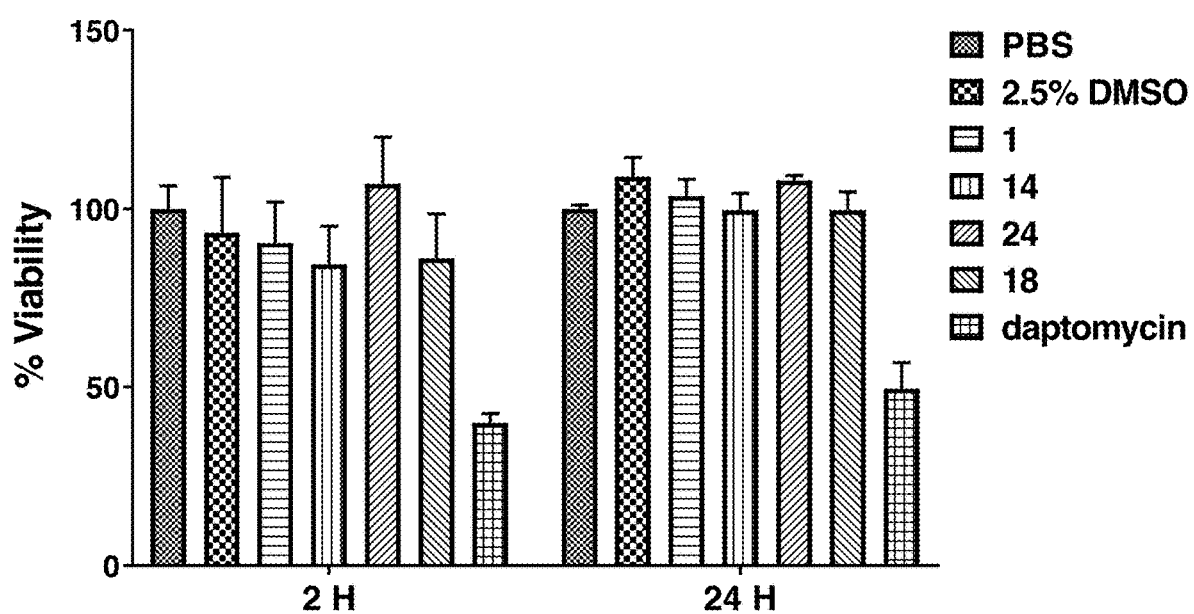
FIGS. 4A-4F are data depicting the safety/cytotoxicity and cell-membrane permeability of r6,N-acyl-Glc Tei analogs according to another embodiment of the present disclosure.
Figure 4B:
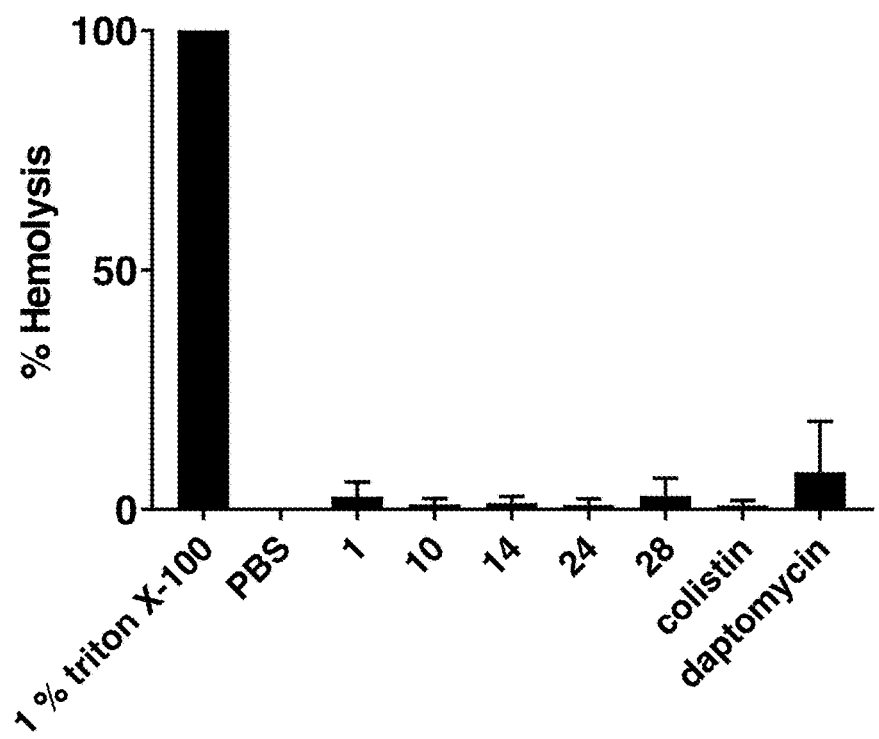

The cytotoxicity of compound 1, 14, 18, 24 alongside daptomycin was individually examined against a human embryonic kidney cells (HEK293T) cell line at two different time points 2 and 24 h (FIG. 4A). These selected compounds did not exhibit any observable toxicity to HEK293T cells up to 100 µgmL$^{-1}$ as opposed to daptomycin that exhibited a considerable extent of cell toxicity. The developed analogs were also subjected to drug-induced hemolysis examination, which is rare but a serious toxicity. Except for daptomycin, all the test compounds showed little or no hemolysis (FIG. 4B).

Figure 4C:
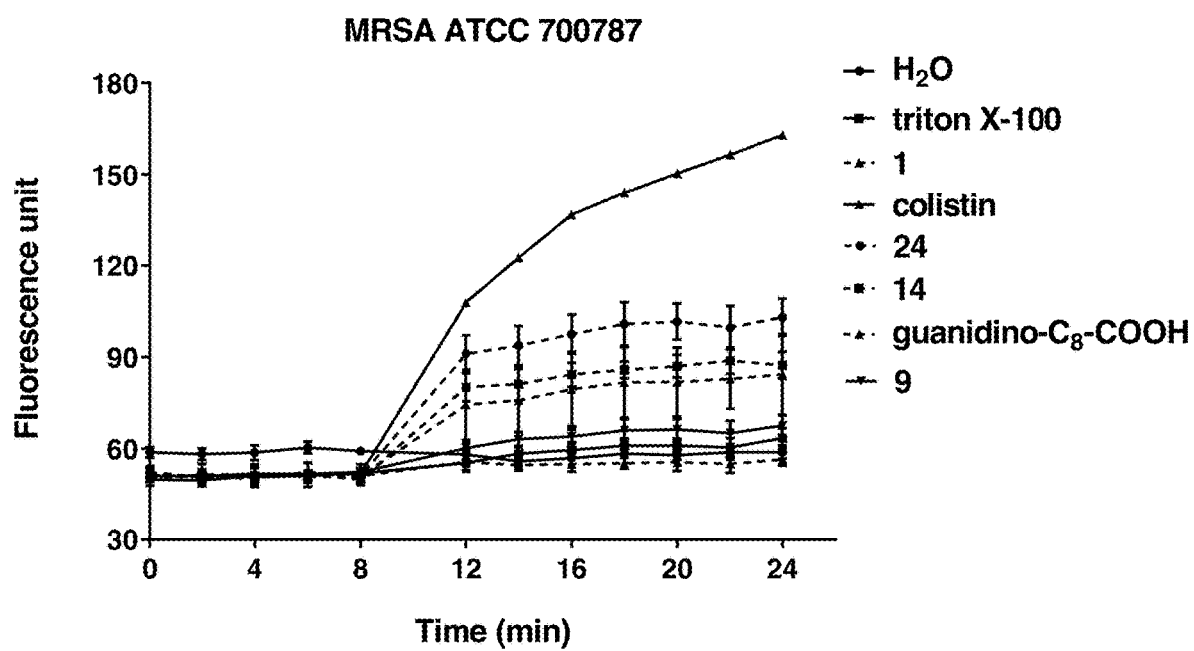
Figure 4D:
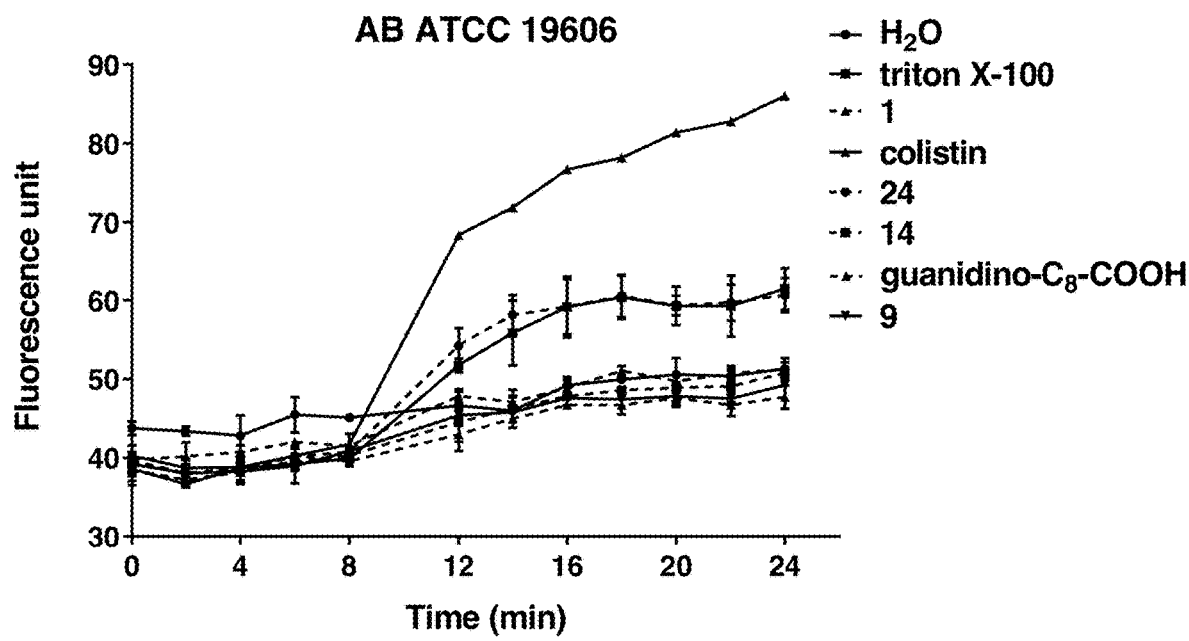
Figure 4E:
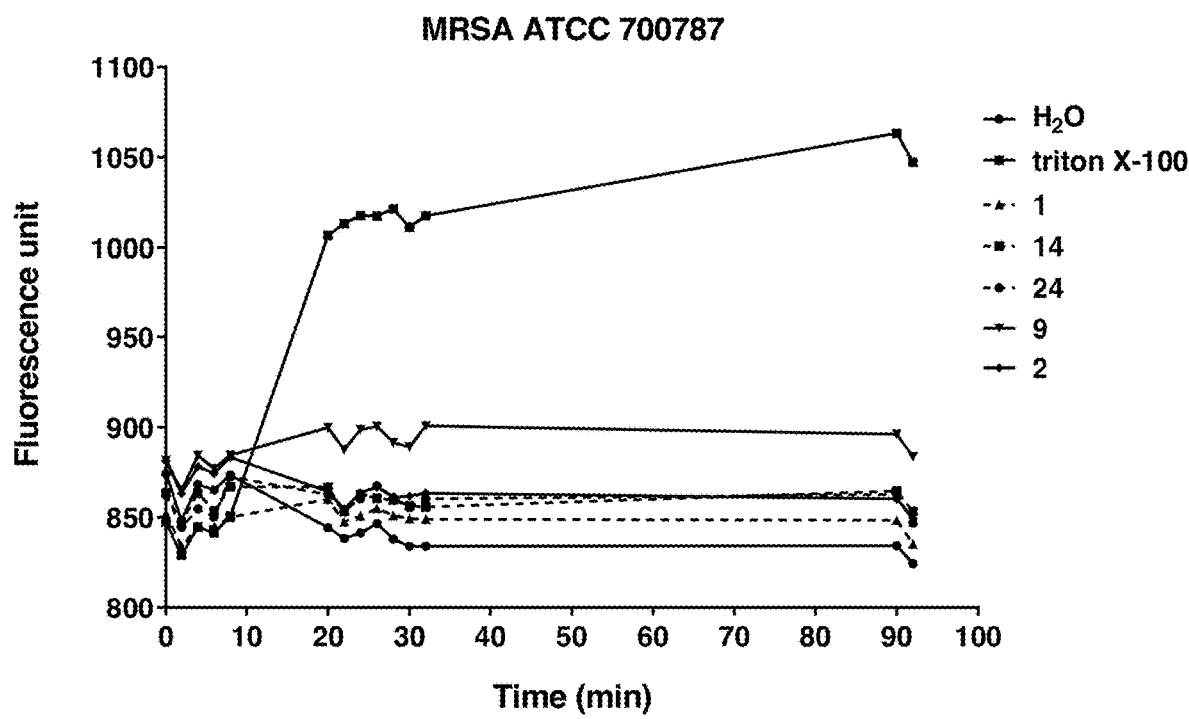
Figure 4F:
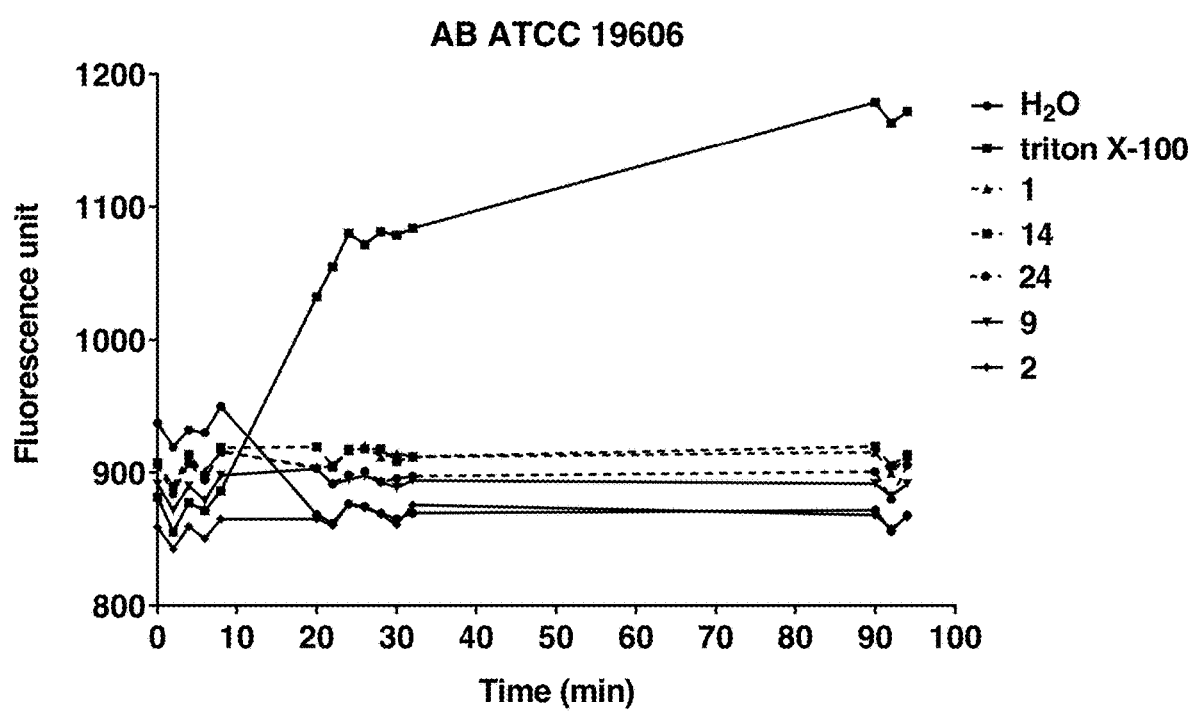

The capability of the developed compounds that permeabilize the cytoplasmic membrane of bacteria was examined using propidium iodide (PI) dye. In principle, PI should pass across the membrane of compromised bacterial cells and fluoresce upon binding to bacterial DNA. Compounds 14 and 24 possessed a median inner membrane permeability on MRSA when compared to colistin (a positive control) and water (a negative control) (FIG. 4C). These two compounds outperformed compound 1 in well correlation to their MIC values. Compound 24 was slightly more potent than compound 14, likely due to the terminal guanidino group in addition to the unique r6,N-acyl-Glc geometry. The same phenomenon was observed in AB, where compound 24 possessed a median inner membrane permeability (equivalent to TRITON X-100) in contrast to compound 14, which had no activity (FIG. 4D). In the 1-N-phenylnaphthylamine (NPN) permeabilization assay, compounds 14 and 24, however, did not show any outer membrane permeabilization on MRSA (without outer membrane) or AB (with outer membrane) (FIGS. 4E and 4F) in agreement with the inherent barrier of outer membrane for lipoglycopeptide antibiotics. Though compound 24 and 25 were effective against AB, there was no a clear-cut answer at the moment with respect to how these compounds reach the inner membrane.

Example 7 In Vivo Efficacy of r6,N-Acyl-Glc Tei Analogs

The sensitivity in vitro of MRSA and AB to r6,N-octyl-Glc-Tei analogs prompted us to examine their efficacy in vivo. Accordingly, the effectiveness on bacterial clearance by 14 and 24 was respectively evaluated against MRSA and AB in a sepsis infection model.

For MRSA, mice were inoculated intraperitoneally (IP) with 0.3 mL of MRSA ATCC 700787 suspension (about $10^7$ CFUmL$^{-1}$). The treatment started 1 hour post-challenge with a single dose of compound 14 (20 mgkg$^{-1}$), compound 1 (20 mgkg$^{-1}$) or saline through IP, where the latter two respectively served as positive and negative controls. To assess the density of bacteraemia, 1 mL peritoneal fluid (PF) was collected from each mouse at 24 hours post-inoculation. For the saline treated control, bacterial count was calculated (about 7.5 log CFUmL$^{-1}$, FIG. 4A). The bacterial load was reduced by 1.5 and 2 log CFUmL$^{-1}$ with the treatment of compound 1 and 14, respectively, where 14 outperformed 1 in agreement with in vitro assays (FIG. 4A).

For AB (ATCC 19606), female C57BL/6 mice were first anesthetized by intraperitoneal injection of zoletil and then intranasally inoculated with 50 µL of bacteria in a PBS solution (about $10^7$-$10^8$ CFUmL$^{-1}$). The treatment started 1 hour post-infection with a single dose of compound 24 (30 mgkg$^{-1}$), compound 1 (30 mgkg$^{-1}$), amikacin (15 mgkg$^{-1}$), or kanamycin (30 mgkg$^{-1}$), where saline/compound 1 and amikacin/kanamycin respectively served as negative and positive controls. To assess the density of bacteraemia, the lungs of mice were lavaged to collect 0.6 mL bronchoalveolar lavage (BAL) fluid from each mouse at 24 hours post-inoculation. For saline/compound 1 treated controls, the bacterial load was counted (about 4 log CFUmL$^{-1}$, FIG. 4B), where the bacterial load was reduced by 0.5 or 1 log CFUmL$^{-1}$ with the treatment of amikacin/kanamycin or compound 24, respectively. Given advantageous pharmacokinetics/pharmacodynamics in vivo, compound 24 that is more effective than amikacin/kanamycin in the animal study is well appreciated (FIG. 4B).

In conclusion, the present disclosure provides several novel compounds that are effective in treating infectious diseases caused by/associated with various bacteria, including gram-positive (e.g., *Staphylococcus aureus* or Enterococci) and gram-negative bacteria (e.g., *Acinetobacter baumannii*), in which the bacteria may be drug-sensitive or drug-resistant. According to the working examples of the present disclosure, the present compounds may be used in combination with each other or with other anti-bacterial agents (for example, kanamycin) so as to produce an additive or a synergistic effect on inhibiting the replication/activity/function of bacteria. Accordingly, the present compounds are potential candidates for the development of lead compounds for manufacturing a medicament or pharmaceutical composition for treating disease and/or disorders associated with bacterial infection.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A compound of formula (I),

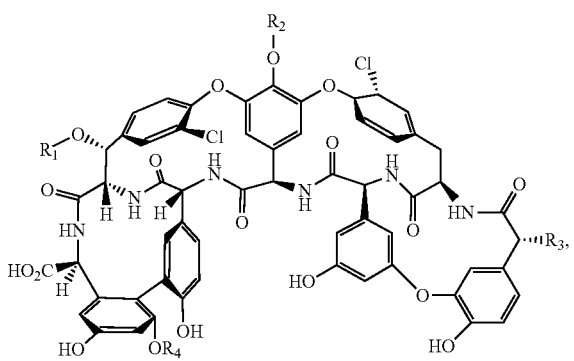

or the pharmaceutically acceptable salt, solvate, stereoisomer, derivative or prodrug thereof, wherein, $R_1$ is

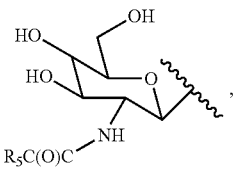

wherein $R_5$ is $C_1$-$C_{12}$ alkyl substituted by —$NH_2$ or

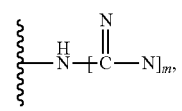

wherein m is an integer of 1 or 2;
$R_2$ is H;
$R_3$ is —$N(CH_3)_2$; and
$R_4$ is H.

2. A pharmaceutical composition comprising the compound of claim 1, or a pharmaceutically acceptable salt thereof, and a pharmaceutically acceptable excipient.

3. A method of treating a bacterial infection in a subject in need thereof, comprising administering to the subject an effective amount of the compound of claim 1, or the pharmaceutically acceptable salt thereof.

4. The method of claim 3, wherein the bacterial infection is caused by a gram-positive bacterium.

5. The method of claim 4, wherein the gram-positive bacterium is *Staphylococcus aureus* or Enterococci.

6. The method of claim 4, wherein the gram-positive bacterium is resistant to an antibiotic.

7. The method of claim 3, wherein the bacterial infection is caused by a gram-negative bacterium.

8. The method of claim 7, wherein the gram-negative bacterium is *Acinetobacter baumannii*.

9. The method of claim 7, wherein the gram-negative bacterium is resistant to an antibiotic.

10. A method of producing the compound of claim 1, comprising,
    (a) glycosylating a compound of formula (Ia) with the aid of a glycosyltransferase in the presence of an acylated glycan,

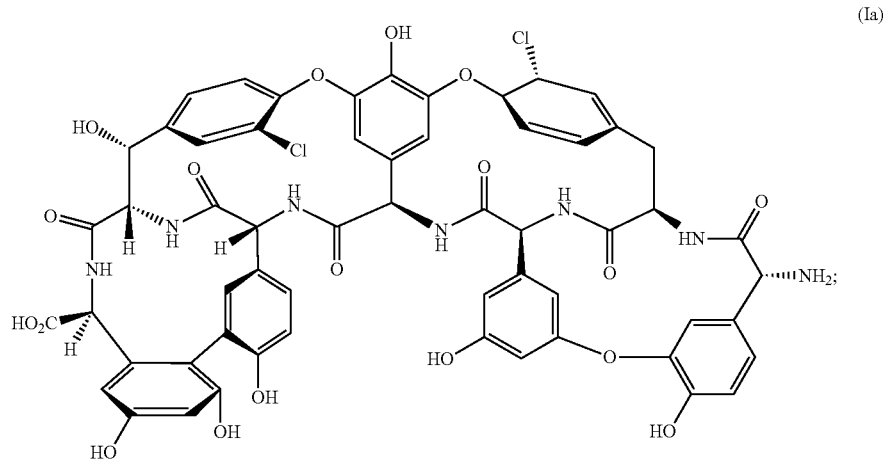

(Ia)

(b) methylating the product of the step (a) with the aid of a methyltransferase;
(c) deacylating the product of the step (b) with the aid of a deacylase; and
(d) acylating the product of the step (c) with the aid of an acyltransferase in the presence of an acyl donor thereby producing the compound of claim 1, wherein the acyl donor comprises a functional group of —C(O)CR$_5$, and R$_5$ is —NH$_2$.

11. The method of claim 10, wherein the acylated glycan is uridine diphosphate N-acetylglucosamine (UDP-GlcNAc).

12. The method of claim 10, wherein
the glycosyltransferase has the amino acid sequence of SEQ ID NO: 5;
the deacylase has the amino acid sequence of SEQ ID NO: 6;
the acyltransferase has the amino acid sequence of SEQ ID NO: 7; and
the methyltransferase has the amino acid sequence of SEQ ID NO: 4.

13. The method of claim 10, further comprising a step of guanylating the product of step (d).

* * * * *